United States Patent
Tamura et al.

(10) Patent No.: US 9,580,600 B2
(45) Date of Patent: *Feb. 28, 2017

(54) THICKENING OR GELLING AGENT FOR OILY RAW MATERIALS

(75) Inventors: Seiki Tamura, Ichihara (JP); Tomohiro Iimura, Sodegaura (JP); Tatsuo Souda, Ichihara (JP); Akito Hayashi, Ichihara (JP); Haruhiko Furukawa, Chiba (JP)

(73) Assignee: DOW CONRING TORAY CO., LTD., Chiyoda-ku, Tokyo (JP)

( * ) Notice: Subject to any disclaimer, the term of this patent is extended or adjusted under 35 U.S.C. 154(b) by 726 days.

This patent is subject to a terminal disclaimer.

(21) Appl. No.: 13/503,623

(22) PCT Filed: Oct. 25, 2010

(86) PCT No.: PCT/JP2010/069248
§ 371 (c)(1),
(2), (4) Date: Jul. 11, 2012

(87) PCT Pub. No.: WO2011/049247
PCT Pub. Date: Apr. 28, 2011

(65) Prior Publication Data
US 2012/0269748 A1    Oct. 25, 2012

(30) Foreign Application Priority Data
Oct. 23, 2009  (JP) ................................. 2009-244977

(51) Int. Cl.
| | | |
|---|---|---|
| *A61K 8/58* | (2006.01) | |
| *A61Q 17/04* | (2006.01) | |
| *A61Q 1/02* | (2006.01) | |
| *A61K 8/18* | (2006.01) | |
| *C08F 283/12* | (2006.01) | |
| *C08G 77/38* | (2006.01) | |
| *C08L 83/04* | (2006.01) | |
| *C08L 51/08* | (2006.01) | |
| *C08L 83/10* | (2006.01) | |
| *C07F 7/08* | (2006.01) | |
| *C08L 83/14* | (2006.01) | |
| *A61K 8/04* | (2006.01) | |
| *A61K 8/892* | (2006.01) | |
| *A61Q 19/00* | (2006.01) | |
| *C08L 83/16* | (2006.01) | |
| *C08L 91/00* | (2006.01) | |
| *A61Q 19/02* | (2006.01) | |
| *A61Q 1/04* | (2006.01) | |
| *A61Q 1/06* | (2006.01) | |
| *A61Q 5/00* | (2006.01) | |
| *A61Q 15/00* | (2006.01) | |
| *A61Q 1/10* | (2006.01) | |
| *C11D 3/37* | (2006.01) | |

(52) U.S. Cl.
CPC .............. *C08L 83/14* (2013.01); *A61K 8/042* (2013.01); *A61K 8/892* (2013.01); *A61Q 19/00* (2013.01); *C08G 77/38* (2013.01); *C08L 83/16* (2013.01); *C08L 91/00* (2013.01); *A61K 2800/48* (2013.01)

(58) Field of Classification Search
CPC .......... C08L 83/16; C08L 83/14; C08L 91/00; A61K 2800/48; A61K 8/04; A61K 8/892; A61K 8/042; A61Q 19/00; C08G 77/38
USPC ............. 424/59, 62, 63, 64, 65, 70.7, 70.12, 424/70.121; 510/466; 514/772, 772.1, 514/785; 525/478; 556/445
See application file for complete search history.

(56) References Cited

U.S. PATENT DOCUMENTS

| | | |
|---|---|---|
| 4,431,789 A | 2/1984 | Okazaki et al. |
| 4,616,076 A | 10/1986 | Ona et al. |
| 4,631,208 A | 12/1986 | Westall |
| 4,698,178 A | 10/1987 | Huttinger et al. |
| 5,144,054 A | 9/1992 | Shioya et al. |
| 5,466,849 A | 11/1995 | Shioya et al. |
| 5,472,686 A | 12/1995 | Tsubaki et al. |

(Continued)

FOREIGN PATENT DOCUMENTS

| | | |
|---|---|---|
| CA | 2291284 A1 | 5/2000 |
| EP | 1031592 A2 | 8/2000 |

(Continued)

OTHER PUBLICATIONS

MPEP Chapter 1800, Section 1850, Rev. 7, Jul. 2008, pp. 85-91 (7 pages).*
International Preliminary Report on Patentability, PCT/JP2010/069248 (May 15, 2012), 7 pages.*
Shin-Etsu, Shin-Etsu Silicone, Silicone Products for Personal Care, [Retrieved from internet <URL: http://www.shinetsusilicones.com/files/literature/Shin-Etsu%20Unique%20Materials%202010%2011_2.pdf >], dated Nov. 2010, 20 pages.*

(Continued)

*Primary Examiner* — Anna Pagonakis
*Assistant Examiner* — Miriam A Levin
(74) *Attorney, Agent, or Firm* — Howard and Howard Attorneys PLLC

(57) ABSTRACT

An excellent oil-thickening or -gelling agent is provided. The agent is compatible with various oils and can freely control the form or viscosity of oily raw materials or cosmetics by changing the quantity thereof added. The agent contains a novel co-modified organopolysiloxane that contains both a group having a siloxane dendron structure and a hydrophilic group and that preferably has a degree of polymerization of 200 or more. A gel composition containing the co-modified organopolysiloxane is also provided. The gel composition is useful as a base that permits stable and easy preparation of cosmetics having various viscoelasticities and forms. An oil is kept in the form of a gel that has a viscoelasticity falling within the intermediate range between the viscoelasticity of liquid and that of solid. Cosmetics containing the thickening or gelling agent are also provided.

15 Claims, No Drawings

(56) References Cited

U.S. PATENT DOCUMENTS

| | | | |
|---|---|---|---|
| 5,484,950 A | 1/1996 | Crivello | |
| 5,654,362 A | 8/1997 | Schulz, Jr. et al. | |
| 5,660,819 A | 8/1997 | Tsubaki et al. | |
| 5,874,069 A | 2/1999 | Mendolia et al. | |
| 5,889,108 A | 3/1999 | Zhang | |
| 5,919,441 A | 7/1999 | Mendolia et al. | |
| 5,929,163 A | 7/1999 | Harashima | |
| 5,981,680 A | 11/1999 | Petroff et al. | |
| 6,168,782 B1 | 1/2001 | Lin et al. | |
| 6,184,407 B1 | 2/2001 | Yoshitake et al. | |
| 6,534,072 B2 | 3/2003 | Mondet et al. | |
| 6,576,623 B1 | 6/2003 | Nakanishi et al. | |
| 6,660,281 B1 | 12/2003 | Nakanishi et al. | |
| 7,001,971 B2 | 2/2006 | Nakanishi | |
| 7,482,419 B2 | 1/2009 | Caprasse et al. | |
| 7,507,775 B2 | 3/2009 | Leatherman et al. | |
| 7,601,680 B2 | 10/2009 | Wang et al. | |
| 7,612,051 B2 | 11/2009 | Kamei et al. | |
| 7,655,744 B2 | 2/2010 | Miyanaga | |
| 7,771,709 B2 | 8/2010 | Nakanishi et al. | |
| 7,998,903 B2 | 8/2011 | Nakanishi et al. | |
| 8,034,891 B2 | 10/2011 | Okawa | |
| 8,080,239 B2 | 12/2011 | Matsuo et al. | |
| 8,513,174 B2 | 8/2013 | Araki et al. | |
| 8,597,619 B2 * | 12/2013 | Tamura | A61K 8/894 424/59 |
| 8,715,626 B2 * | 5/2014 | Tamura | A61K 8/894 424/59 |
| 8,784,787 B2 * | 7/2014 | Tamura | A61K 8/894 424/70.19 |
| 9,133,309 B2 * | 9/2015 | Iimura | A61Q 19/00 |
| 2005/0261133 A1 | 11/2005 | Nakanishi et al. | |
| 2006/0013843 A1 * | 1/2006 | Shimizu | A61K 8/37 424/401 |
| 2007/0207176 A1 * | 9/2007 | Kamei | A61K 8/19 424/401 |
| 2009/0203802 A1 * | 8/2009 | Kamei et al. | 514/769 |
| 2010/0190871 A1 | 7/2010 | Araki et al. | |
| 2011/0182846 A1 | 7/2011 | Ikeda et al. | |
| 2012/0269747 A1 | 10/2012 | Iimura et al. | |
| 2012/0269875 A1 | 10/2012 | Tamura et al. | |

FOREIGN PATENT DOCUMENTS

| | | |
|---|---|---|
| EP | 2014701 A2 | 1/2009 |
| EP | 2174985 A1 | 4/2010 |
| EP | 2180028 A1 | 4/2010 |
| JP | 50-004199 A | 1/1975 |
| JP | 57-139123 A | 8/1982 |
| JP | 57-149290 A | 9/1982 |
| JP | 61-090732 A | 5/1986 |
| JP | 61-123635 A | 6/1986 |
| JP | 61-127733 A | 6/1986 |
| JP | 61-293903 A | 12/1986 |
| JP | 61-293904 A | 12/1986 |
| JP | 62-034039 B | 7/1987 |
| JP | 62-187406 A | 8/1987 |
| JP | 62-195389 A | 8/1987 |
| JP | 62-215510 A | 9/1987 |
| JP | 62-216635 A | 9/1987 |
| JP | 4108795 A | 4/1992 |
| JP | H 04-108795 A | 4/1992 |
| JP | 4134013 A | 5/1992 |
| JP | 04-211605 A | 8/1992 |
| JP | 04-234307 A | 8/1992 |
| JP | 05-112424 A | 5/1993 |
| JP | 05-163436 A | 6/1993 |
| JP | 05-186596 A | 7/1993 |
| JP | 05-311076 A | 11/1993 |
| JP | 06-157236 A | 6/1994 |
| JP | 06-305933 A | 11/1994 |
| JP | 6089147 B | 11/1994 |
| JP | 07-025728 A | 1/1995 |
| JP | 07-033622 A | 2/1995 |
| JP | 07-100358 A | 4/1995 |
| JP | 07-187945 A | 7/1995 |
| JP | 08-217626 A | 8/1996 |
| JP | 08-268831 A | 10/1996 |
| JP | 08-268832 A | 10/1996 |
| JP | 02-583412 B2 | 2/1997 |
| JP | 09-071504 A | 3/1997 |
| JP | 09-194323 A | 7/1997 |
| JP | 09-194594 A | 7/1997 |
| JP | 02-719303 B2 | 2/1998 |
| JP | 10-167946 A | 6/1998 |
| JP | 10-245317 A | 9/1998 |
| JP | 10-310504 A | 11/1998 |
| JP | 10-310505 A | 11/1998 |
| JP | 10-310506 A | 11/1998 |
| JP | 10-310507 A | 11/1998 |
| JP | 10-310508 A | 11/1998 |
| JP | 10-310509 A | 11/1998 |
| JP | 10-316536 A | 12/1998 |
| JP | 11-049957 A | 2/1999 |
| JP | 2000-063225 A | 2/2000 |
| JP | 2000-072784 A | 3/2000 |
| JP | 2000-239390 A | 9/2000 |
| JP | 2001-011281 A | 1/2001 |
| JP | 2001-039819 A | 2/2001 |
| JP | 2001-072891 A | 3/2001 |
| JP | 2001-316473 A | 11/2001 |
| JP | 2002-038013 A | 2/2002 |
| JP | 2002-179797 A | 6/2002 |
| JP | 2002-179798 A | 6/2002 |
| JP | 2004-169015 A | 6/2004 |
| JP | 2004-182680 A | 7/2004 |
| JP | 2004-231608 A | 8/2004 |
| JP | 2004-339244 A | 12/2004 |
| JP | 2005-042097 A | 2/2005 |
| JP | 2005-089494 A | 4/2005 |
| JP | 2005-194523 A | 7/2005 |
| JP | 2005-344076 A | 12/2005 |
| JP | 2006-218472 A | 8/2006 |
| JP | 2007-532754 A | 11/2007 |
| JP | 2009-511710 A | 3/2009 |
| JP | 2009-511712 A | 3/2009 |
| WO | WO 03/041664 A1 | 5/2003 |
| WO | WO 03/075864 A1 | 9/2003 |
| WO | WO 2007/135771 A1 | 11/2007 |
| WO | WO 2009/022621 A1 | 2/2009 |
| WO | WO 2009/025146 A1 | 2/2009 |
| WO | WO 2011/049246 | 4/2011 |
| WO | WO 2011/049248 | 4/2011 |

OTHER PUBLICATIONS

Supplementary European Search Report for Application No. EP 10 82 5093 dated May 16, 2013; 2 pages.

English language abstract and machine-assisted English translation for JP 09-194594 extracted from the PAJ database on Nov. 26, 2012, 56 pages.

English language abstract for JP 02-583412 extracted from the espacenet.com and machine-assisted translation extracted from the PAJ database on Jul. 12, 2012, 22 pages.

English language abstract for JP 02-719303 extracted from the espacenet.com database and machine-assisted translation extracted from the PAJ database on Jul. 16, 2012, 24 pages.

English language abstract for JP 4134013 extracted from the espacenet.com database on Nov. 26, 2012, 19 pages.

English language abstract for JP 04-211605 extracted from the espacenet.com database on Jul. 26, 2012, 8 pages.

English language abstract for JP 04-234307 extracted from the espacenet.com database on Jul. 26, 2012, 9 pages.

English language abstract and machine-assisted translation for JP 05-112424 extracted from the PAJ database on Jul. 16, 2012, 80 pages.

English language abstract and machine-assisted translation for JP 05-163436 extracted from the PAJ database on Jul. 26, 2012, 26 pages.

English language abstract and machine-assisted translation for JP 05-186596 extracted from the PAJ database on Jul. 12, 2012, 52 pages.

(56) References Cited

OTHER PUBLICATIONS

English language abstract for JP 05-311076 extracted from the espacenet.com database on Jul. 26, 2012, 14 pages.
English language abstract for JP 62-034039 extracted from the espacenet.com database on Nov. 26, 2012, 14 pages.
English language abstract and machine-assisted translation for JP 06-157236 extracted from the PAJ database on Jul. 13, 2012, 26 pages.
English language abstract and machine-assisted translation for JP 06-305933 extracted from the PAJ database on Jul. 16, 2012, 36 pages.
English language abstract and machine-assisted translation for JP 07-025728 extracted from the PAJ database on Jul. 16, 2012, 39 pages.
English language abstract and machine-assisted translation for JP 07-033622 extracted from the PAJ database on Jul. 16, 2012, 40 pages.
English language abstract and machine-assisted translation for JP 07-100358 extracted from the PAJ database on Jul. 26, 2012, 29 pages.
English language abstract and machine-assisted translation for JP 07-187945 extracted from the PAJ database on Jul. 13, 2012, 56 pages.
English language abstract for JP 2006-218472 extracted from the espacenet.com database on Nov. 26, 2012, 14 pages.
English language abstract and machine-assisted translation for JP 08-217626 extracted from the PAJ database on Jul. 26, 2012, 53 pages.
English language abstract and machine-assisted translation for JP 08-268831 extracted from the PAJ database on Jul. 26, 2012, 35 pages.
English language abstract and machine-assisted translation for JP 08-268832 extracted from the PAJ database on Jul. 26, 2012, 47 pages.
English language abstract and machine-assisted translation for JP 09-071504 extracted from the PAJ database on Jul. 13, 2012, 29 pages.
English language abstract and machine-assisted translation for JP 09-194323 extracted from the PAJ database on Jul. 26, 2012, 31 pages.
English language abstract and machine-assisted translation for JP 10-245317 extracted from the PAJ database on Jul. 26, 2012, 39 pages.
English language abstract and machine-assisted translation for JP 10-310504 extracted from the PAJ database on Jul. 13, 2012, 33 pages.
English language abstract and machine-assisted translation for JP 10-310505 extracted from the PAJ database on Jul. 13, 2012, 28 pages.
English language abstract and machine-assisted translation for JP 10-310506 extracted from the PAJ database on Jul. 13, 2012, 29 pages.
English language abstract and machine-assisted translation for JP 10-310507 extracted from the PAJ database on Jul. 13, 2012, 30 pages.
English language abstract and machine-assisted translation for JP 10-310508 extracted from the PAJ database on Jul. 13, 2012, 33 pages.
English language abstract and machine-assisted translation for JP 10-310509 extracted from the PAJ database on Jul. 13, 2012, 33 pages.
English language abstract and machine-assisted translation for JP 10-316536 extracted from the PAJ database on Jul. 16, 2012, 29 pages.
English language abstract for JP 11-049957 extracted from the espacenet.com database on Jul. 16, 2012, 9 pages.
English language abstract for JP 57-149290 extracted from the espacenet.com database on Jul. 17, 2012, 12 pages.
English language abstract not available for JP 61-090732; however, see English language equivalent U.S. Pat. No. 4,698,178. Original Document extracted from the espacenet.com database on Jul. 13, 2012, 9 pages.
English language abstract not available for JP 61-123635; however, see English language equivalent U.S. Pat. No. 4,631,208. Original Document extracted from the espacenet.com database on Jul. 26, 2012, 7 pages.
English language abstract for JP 61-127733 extracted from the espacenet.com database on Jul. 26, 2012, 12 pages.
English language abstract for JP 61-293903 extracted from the espacenet.com database on Jul. 12, 2012, 13 pages.
English language abstract for JP 61-293904 extracted from the espacenet.com database on Jul. 12, 2012, 15 pages.
English language abstract and machine-assisted English translation for JP 6089147 extracted from the espacenet.com and PAJ databases on Nov. 26, 2012, 54 pages.
English language abstract for JP 62-187406 extracted from the espacenet.com database on Jul. 12, 2012, 11 pages.
English language abstract for JP 62-215510 extracted from the espacenet.com database on Jul. 12, 2012, 16 pages.
English language abstract for JP 62-216635 extracted from the espacenet.com database on Jul. 12, 2012, 13 pages.
English language abstract and machine-assisted translation for JP 2000-063225 extracted from the PAJ database on Jul. 16, 2012, 61 pages.
English language abstract for JP 2000-072784 extracted from the espacenet.com database on Jul. 17, 2012, 13 pages.
English language abstract for JP 2000-239390 extracted from the espacenet.com database on Jul. 17, 2012, 14 pages.
English language abstract for JP 2001-011281 extracted from the espacenet.com database on Jul. 16, 2012, 14 pages.
English language abstract for JP 4108795 extracted from the espacenet.com database on Nov. 26, 2012, 21 pages.
English language abstract for JP 2001-039819 extracted from the espacenet.com database on Jul. 17, 2012, 29 pages.
English language abstract for JP 2001-072891 extracted from the espacenet.com database on Jul. 17, 2012, 23 pages.
English language abstract and machine-assisted translation for JP 2001-316473 extracted from the PAJ database on Jul. 26, 2012, 45 pages.
English language abstract for JP 2002-038013 extracted from the espacenet.com database on Jul. 16, 2012, 19 pages.
English language abstract and machine-assisted translation for JP 2002-179797 extracted from PAJ database on Jul. 13, 2012, 67 pages.
English language abstract for JP 2002-179798 extracted from the espacenet.com database on Jul. 12, 2012, 27 pages.
English language abstract for JP 2004-169015 extracted from the espacenet.com database on Jul. 16, 2012, 43 pages.
English language abstract and machine-assisted translation for JP 2004-182680 extracted from the PAJ database on Jul. 26, 2012, 96 pages.
English language abstract and machine-assisted translation for JP 2004-231608 extracted from the PAJ database on Jul. 26, 2012, 75 pages.
English language abstract for JP 2004-339244 extracted from the espacenet.com database on Jul. 12, 2012, 45 pages.
English language abstract for JP 2005-042097 extracted from the espacenet.com database on Jul. 12, 2012, 59 pages.
English language abstract and machine-assisted translation for JP 2005-089494 extracted from the PAJ database on Jul. 12, 2012, 47 pages.
English language abstract and machine-assisted translation for JP 2005-194523 extracted from the PAJ database on Jul. 26, 2012, 53 pages.
English language abstract for JP 2005-344076 extracted from the espacenet.com database on Jul. 26, 2012, 18 pages.
English language abstract not available for JP 2007-532754; however, see English equivalent U.S. Pat. No. 7,482,419. Original document extracted from espacenet.com database on Jul. 16, 2012, 39 pages.

(56) References Cited

OTHER PUBLICATIONS

English language abstract not available for JP 2009-511710; however, see English equivalent U.S. Pat. No. 7,507,775. Orginal document extracted from the espacenet.com database on Jul. 26, 2012, 29 pages.
English language abstract not available for JP 2009-511712; however, see English equivalent U.S. Pat. No. 7,601,680, Original document extracted from the espacenet.com database on Jul. 26, 2012, 29 pages.
English language abstract for WO 03/041664 extracted from the espacenet.com database on Jul. 26, 2012, 71 pages.
English language abstract for WO 03/075864 extracted from the espacenet.com database on Jul. 16, 2012, 38 pages.
English language abstract for WO 2007/135771 extracted from the espacenet.com database on Jul. 17, 2012, 160 pages.
English language abstract for WO 2009/022621 extracted from the espacenet.com database on Jul. 26, 2012, 53 pages.
English language abstract for WO 2009/025146 extracted from the espacenet.com database on Jul. 26, 2012, 48 pages.
English language abstract for JP 62-195389 extracted from the PAJ database on Nov. 26, 2012, 5 pages.
English language abstract and machine-assisted English translation for JP 10-167946 extracted from the PAJ database on Nov. 26, 2012, 27 pages.
International Search Report for Application No. PCT/JP2010/069237 dated Jan. 11, 2011, 6 pages.
International Search Report for Application No. PCT/JP2010/069249 dated Jan. 11, 2011, 6 pages.
International Search Report for Application No. PCT/JP2010/069248 dated Jan. 11, 2011, 4 pages.
Supplementary European Search Report for Application No. EP 10 82 5094 completed on Dec. 11, 2013, 2 pages.
Murthy, Ranjini et al., "Protein-Resistant Silicones: Incorporation of Poly(ethylene oxide) via Siloxane Tethers", Biomacromolecules 2007, 8, pp. 3244-3252.

\* cited by examiner

THICKENING OR GELLING AGENT FOR OILY RAW MATERIALS

RELATED APPLICATIONS

This application claims priority to and all the advantages of International Patent Application No. PCT/JP2010/069248, filed on Oct. 25, 2010, which claims priority to Japanese Patent Application No. JP2009-244977, filed on Oct. 23, 2009.

TECHNICAL FIELD

The present invention relates to a thickening agent or gelling agent for an oil-based raw material, wherein the thickening agent or gelling agent contains a novel hydrophilic silicone having a siloxane dendron structure, and also relates to a gel composition and a gel cosmetic composition or gel topical composition comprising the gel composition. In addition, the present invention relates to a thickening agent or gelling agent for an oil-based raw material, wherein the thickening agent or gelling agent contains a high molecular weight hydrophilic silicone having a siloxane dendron structure and a tetraglycerin structure, and also relates to a gel composition and a gel cosmetic composition or gel topical composition comprising the gel composition. The novel hydrophilic silicone having a siloxane dendron structure has a variety of functional aspects, suppresses oiliness when compounded in a cosmetic composition having an oil-based raw material as a base, and can produce a cosmetic composition which imparts a natural skin sensation with no discomfort and an excellent moisturizing feel following application.

In particular, the high molecular weight hydrophilic silicone having a tetraglycerin structure and a group having a siloxane dendron structure functions as an excellent oil thickening agent which has excellent compatibility with a variety of oil agent systems and in which it is possible to freely control the form, viscosity and the like of an oil agent or cosmetic composition by adjusting the added amount of the high molecular weight hydrophilic silicone. In addition, the high molecular weight hydrophilic silicone also functions as an excellent dispersing/solidifying agent which can uniformly and stably disperse/solidify a powder or colorant in a cosmetic composition having an oil-based raw material as a base and which can maintain an excellent cosmetic effect and a natural feeling on the skin with no discomfort for approximately one day after the high molecular weight hydrophilic silicone is applied to the skin.

Furthermore, by combining specified amounts of an oil-based raw material, an organic alcohol compound, and water, it is possible to obtain a stable gel composition that can maintain a variety of mixed silicone/organic oils in a gel form having an intermediate viscoelasticity between a liquid and a solid. By compounding a powder in this composition, or by further compounding a UV absorber, a film-forming agent, a salt, and the like, it is possible to easily obtain a stable gel composition. In addition, by diluting these gel compositions by further compounding water therein, it is possible to obtain a cosmetic composition in an arbitrary form having a lower viscosity than paste-form, cream-form, and milk-form forms, and the like. In addition, by further compounding water and a bioactive substance in these gel compositions, it is possible to obtain a topical composition also having an arbitrary form.

BACKGROUND ART

Looking at the conventional technology from the perspective of thickening or gelling oils, oil agent systems used in cosmetic compositions often contained silicone oils, but in such cases, the effect achieved by organic thickening/gelling agents was poor. Techniques for thickening or gelling oils can provide cosmetic composition manufacturers with a degree of freedom by which it is possible to arbitrarily control the form of a cosmetic composition from liquid to cream-form, paste-form, gel, solid, and the like, and are extremely important techniques. As a result, there has been an increase in the development of modified silicone-based thickening agents and gelling agents that are also advantageous in terms of feeling to touch and also an increase in research into using these thickening agents and gelling agents in cosmetic compositions.

The technique of solidifying oil agents by means of wax-form alkyl-modified silicones was known from the past, but this technique generally caused problems such as an increase in oiliness and a deterioration in spreadability and feeling to touch, the degree of freedom in controlling the form, viscosity and the like of a cosmetic composition being relatively low, and solidification readily occurring regardless of the added amount of the wax-form alkyl-modified silicone.

In addition, a gel silicone composition obtained by gelling a silicone oil using a polyether-modified silicone and water has been developed (see Patent Document 7), but this technique had the problem of the thickening/gelling effect being insufficient when an organic oil was contained in an oil agent system. In addition, this technique had problems in terms of feeling to touch, such as greasiness.

Meanwhile, there have been reports of techniques for gelling oils by means of amino acid derivative-modified silicones, straight chain polyamide-modified silicones, and the like, and the use of such techniques in cosmetic compositions. (Patent Documents 8 to 11 and so on) These gelling agents were excellent in terms of feeling to touch, but had a tendency to readily cause solidification regardless of the added amount of the gelling agent and involved the problem of difficulty in freely controlling the form, viscosity, and the like of a cosmetic composition. In addition, because of the gel being overly hard and solid, if the surface of the gel was scratched, the scratch remained on the surface and the appearance of the gel was impaired because it was not possible to restore the surface of the gel to a smooth state.

That is, silicone-based oil gelling agents of most conventional technology were of a type that solidified oils, and excellent oil thickening agents by which it was possible to freely control the form, viscosity, and the like of an oil or cosmetic composition according to the added amount of the thickening agent were not known. Furthermore, materials and techniques able to stably thicken a variety of oil agent systems containing combinations of silicone oils and organic oils were also not known.

Next, as an explanation of the conventional technology in terms of the relationship between a (poly)glycerin-modified silicone and oil thickening/gelling techniques, cosmetic compositions obtained by combining a silicone branched polyhydric alcohol-modified silicone (for example, an alkyl/linear siloxane branch/polyglycerin co-modified silicone) with an organo-modified clay mineral or a fructooligosaccharide fatty acid ester, which are known as oil thickening/gelling agents (see Patent Documents 12 and 13), a makeup cosmetic composition material that contains specific proportions of an alkyl glyceryl ether-modified silicone having a specific structure and silicic anhydride, which is known as an oil thickening/gelling agent (see Patent Document 14), and the like have been proposed.

The (poly)glycerin-modified silicones used in these techniques have poor oil thickening/gelling capacity, and must therefore be used in combination with another material capable of effectively thickening or gelling an oil agent, and had the problem of the effect of controlling the viscosity or form required for a cosmetic composition being unsatisfactory. In addition, organo-modified clay minerals and silicic anhydride can cause aggregation depending on the type of oil agent or the water content, and the proposed cosmetic compositions had problems in terms of stability. Fructooligosaccharide fatty acid esters exhibited insufficient capacity for thickening/gelling silicone oils other than cyclic siloxanes, and had the problem of reduced freedom when formulating cosmetic compositions.

Recently, Patent Document 15 has proposed a novel alternating copolymer of organopolysiloxane with polyglycerin derivative, and suggests that a high molecular weight polyglycerin-modified silicone can be obtained without the problem of white turbidness and the like, caused by the unreacted raw material occurring. However, it is clear from the chemical structure that this compound has a hydrophilic group portion incorporated on its backbone. As a result, this copolymer has properties completely different from those of conventional general-use hydrophilic silicones such as polyether-modified silicones and the like and, therefore a high level of technical skill is necessary to stably compound this copolymer in delicate formulations such as cosmetic products and the like, leading to the problem of the field of use being limited. Furthermore, this copolymer has good compatibility with oil agents comprising only silicone-based oils, but readily undergoes phase separation in mixed oil agent systems comprising silicone-based oils and organic oils, and had the problem of being unable to achieve a satisfactory effect.

The cause of such problems is closely related to problems in production techniques of conventional polyhydric alcohol-modified silicone. That is, silicones modified by polyhydric alcohols such as (poly)glycerin had a low degree of freedom in terms of structural design and were difficult to produce with stable product quality. Such polyhydric alcohol-modified silicones are ordinarily produced by adding a polyhydric alcohol derivative having a reactive unsaturated group to an organohydrogensiloxane. However, in many cases, compatibility between the remaining polyhydric alcohol derivative and the copolymer that is a reaction product is low, and such silicones separate into two phases within a short period of time following production, meaning that there were significant constraints when mass producing such silicones.

Additionally, compatibility between organohydrogensiloxanes and such polyhydric alcohol derivatives is fundamentally low and, therefore, when the design is such that molecular weight of the copolymer exceeds about 5,000, the addition reaction does not complete even if a solvent is added, thus, in many cases, leading to difficulties in producing the target product. Even when the molecular weight is about 3,000, the unreacted product gradually separates or precipitates. This necessitates a task of removing the separated or precipitated material and is a large obstruction from the perspective of production efficiency as well. (Patent Documents 16 to 18)

Even when a compound is used in which a form of the hydroxyl group is protected as the polyhydric alcohol derivative, deprotection is required following completion of the reaction and, therefore, the problem of separation into two phases cannot be avoided. In addition, heavy acidizing conditions must be introduced in order to achieve deprotection in this method, and the desired product, such as one having a low molecular weight, cannot be obtained in an easily reproducible manner as a result of disconnections of the silicone backbone occurring. (Patent Document 19)

Patent Document 20 proposes a method for producing a branched polyglycerol-modified silicone obtained by adding/graft polymerizing a silicone having at least one functional group selected from the group consisting of hydroxy groups, carboxy groups, amino groups, imino groups, mercapto groups, and epoxy groups, with 2,3-epoxy-1-propanol in the presence of an acidic or basic catalyst. However, with this method, the siloxane backbone disconnects during the graft polymerization, which results in two or more components having different properties being prone to be produced as the copolymer. This led to a multitude of problems related to product quality, refining processes, and the like.

For these reasons, because few conventional polyhydric alcohol-modified silicone are of practical use and are limited in terms of production techniques, most applied research has related to low molecular weight polyhydric alcohol-modified silicones. Examples of research into the use of high molecular weight polyglycerin-modified silicones, such as those having molecular weights in excess of 15,000, in cosmetic compositions cannot be found, except for Patent Document 15, which relates to a block copolymer, and in particular, there are no examples of reports into the use in cosmetic compositions of high molecular weight silicones in which a side chain and/or terminal of the polysiloxane backbone is modified by a polyglycerin derivative.

On the other hand, white pigments such as titanium oxide and zinc oxide, coloring pigments such as red iron oxide, and powders such as mica, sericite, and the like are widely used as basic cosmetic products, rouges, sunscreens, nail colors, nail coatings, foundations, mascaras, eye liners, and similar cosmetic compositions. Reasons for compounding these powders in cosmetic compositions include adjusting the hue, covering properties and feeling to touch of a cosmetic composition, and examples in which these powders have been combined with conventional polyhydric alcohol-modified silicones and used in oil-based cosmetic compositions have been reported. (Patent Documents 1 to 6 and 12 to 14)

However, aggregation or sedimentation of the powder readily occurred in these techniques, and it was not possible to give the user sufficient satisfaction for reasons such as coating unevenness or insufficient covering properties when applied to the skin or unnatural hues. In addition, the polyhydric alcohol-modified silicone used has a low molecular weight and poor oil thickening properties, and is therefore unsatisfactory in terms of cosmetic retainability.

Among powders, silicone-based powders such as organopolysiloxane elastomer spherical powders, poly(methyl silsesquioxane) powders, silicone resin powders, and silicone rubber powders and organic resin powders such as silk powders, nylon powders, poly(methyl methacrylate) powders, and polyethylene powders are excellent in terms of oil absorption capacity, and therefore mitigate the strong oiliness inherent in oil-based cosmetic compositions and the like and achieve the effect of making the skin sensation/feeling more natural following application. However, such powders were difficult to disperse uniformly in formulations and caused problems such as formulations feeling powdery as the compounded amount of the powder increased.

Therefore, there was a need for a material and/or cosmetic composition which can uniformly and stably disperse/solidify a powder or colorant in an oil-based cosmetic composition and which can maintain an excellent cosmetic effect and a natural feeling on the skin with no discomfort for approximately 1 day after the oil-based cosmetic composition is applied to the skin.

Finally, an explanation will be given of the conventional technology that relates to silicone-containing gel compositions. Interest has been shown in gel cosmetic compositions in terms of characteristics and effects based on the physical structures thereof, and a variety of investigations have been carried out. Although linked to oil thickening/gelling techniques, cosmetic compositions often have the problem of being difficult to use when in a form that is completely solid or a liquid having a low viscosity, meaning that the scope of application is limited. As a result, gel cosmetic compositions having an intermediate viscosity or elasticity between a liquid and a solid and development of materials and techniques able to control cosmetic compositions in these forms are needed.

Therefore, among numerous techniques for thickening/gelling oils, the technique disclosed in Patent Document 7 of a gel silicone composition can greatly thicken or gel a silicone oil that is an oil agent having a high compounding content in a cosmetic composition and exhibits good compositional stability compared to cases in which a powdery gelling agent is used, and is widely used as a base for a gel cosmetic composition or a base for an emulsion composition or emulsion cosmetic composition. (Patent Documents 21 to 26)

However, the polyether-modified silicone used as a thickening/gelling agent in Patent Document 7 must contain water in order for gelling to be possible, and therefore had the problem of the range of formulations being limited and had concerns regarding stickiness and greasiness depending on the compounded amount of the polyether-modified silicone. Furthermore, in cases where an oil agent system contains an organic oil, the thickening/gelling effect was poor.

In addition to silicone oils, a variety of oil agents such as hydrocarbon oils and ester oils are used in cosmetic compositions, and these oil agents are often additionally used in cosmetic composition formulations in order to make use of each oil agent's advantages and make up for each oil agent's drawbacks in terms of feeling to touch and the like. Therefore, there is a need for a gel cosmetic composition in which a variety of oil agent systems comprising a combination of a silicone oil and an organic oil can be maintained in a gel form having an intermediate viscoelasticity between a liquid and a solid. In addition, there is a need for a gel cosmetic composition in which the form, viscosity and the like of the gel cosmetic composition can be freely controlled by adjusting the added amount of the thickening/gelling agent.

Patent Document 1: Japanese Patent No. 3389271 (Japanese Unexamined Patent Application Publication No. H-06-157236)
Patent Document 2: Japanese Patent No. 3513682 (Japanese Unexamined Patent Application Publication No. H-09-71504)
Patent Document 3: Japanese Patent No. 3625471 (WO2003-075864)
Patent Document 4: Japanese Unexamined Patent Application Publication No. H-06-305933 (Japanese Patent No. 3477222)
Patent Document 5: Japanese Unexamined Patent Application Publication No. H-07-25728 (Japanese Patent No. 3160427)
Patent Document 6: Japanese Unexamined Patent Application Publication No. H-07-33622 (Japanese Patent No. 3200247)
Patent Document 7: Japanese Patent No. 3333782 (Japanese Unexamined Patent Application Publication No. H-05-311076)
Patent Document 8: Japanese Unexamined Patent Application Publication No. 2004-182680
Patent Document 9: U.S. Pat. No. 5,874,069
Patent Document 10: U.S. Pat. No. 5,919,441
Patent Document 11: U.S. Pat. No. 6,534,072
Patent Document 12: Japanese Patent No. 3678420 (WO2003-041664)
Patent Document 13: Japanese Unexamined Patent Application Publication No. 2004-231608
Patent Document 14: Japanese Unexamined Patent Application Publication No. 2005-194523
Patent Document 15: Japanese Unexamined Patent Application Publication No. 2005-42097
Patent Document 16: Japanese Patent Publication No. S-62-34039
Patent Document 17: Japanese Patent No. 3976226 (Japanese Unexamined Patent Application Publication No. 2002-179798)
Patent Document 18: Japanese Unexamined Patent Application Publication No. 2005-089494
Patent Document 19: Japanese Patent Publication No. H-06-089147 (Japanese Patent No. 1956013)
Patent Document 20: Japanese Unexamined Patent Application Publication No. 2004-339244
Patent Document 21: Japanese Patent No. 3639315 (Japanese Unexamined Patent Application Publication No. H-07-100358)
Patent Document 22: Japanese Patent No. 3407770 (Japanese Unexamined Patent Application Publication No. H-08-217626)
Patent Document 23: Japanese Patent No. 3719540 (Japanese Unexamined Patent Application Publication No. H-09-194323)
Patent Document 24: Japanese Patent No. 3580384 (Japanese Unexamined Patent Application Publication No. H-08-268831)
Patent Document 25: Japanese Patent No. 3580385 (Japanese Unexamined Patent Application Publication No. H-08-268832)
Patent Document 26: Japanese Patent No. 3313043 (Japanese Unexamined Patent Application Publication No. H-10-245317)

DISCLOSURE OF THE INVENTION

Problem to be Solved by the Invention

In order to resolve the problems described above, an object of the present invention is to provide an excellent oil thickening agent or gelling agent which has excellent compatibility with a variety of oil agent systems and which can freely control the form, viscosity, and the like of an oil-based raw material or cosmetic composition by adjusting the added amount of the thickening agent or gelling agent.

Another problem to be addressed by the present invention is to provide an excellent dispersing/solidifying agent which can uniformly and stably disperse/solidify a powder or colorant in a cosmetic composition having an oil-based raw material as a base and which can maintain an excellent cosmetic effect and a natural feeling on the skin with no discomfort for approximately one day after the cosmetic composition is applied to the skin.

Yet another problem to be addressed by the present invention is to provide a gel composition which is a base used to stably and easily produce cosmetic compositions having a variety of viscoelasticities and forms, such as gel, paste-form, cream-form, milk-form, and the like, and which can maintain a variety of oil agents in a gel form having an intermediate viscoelasticity between a liquid and a solid. Furthermore, the present invention provides a stable gel composition which has a variety of functions and which can be easily obtained by compounding a powder in this composition or by further compounding a UV absorber, a film-forming agent, a salt and the like commonly used in cosmetic compositions. In particular, an object of the present invention is to provide a gel cosmetic composition that optionally ensures optical transparency and has excellent storage stability when compounded in an emulsion-type gel cosmetic composition.

Yet another problem to be addressed by the present invention is to provide a method for easily obtaining a cosmetic composition in an arbitrary form having a lower viscosity than paste-form, cream-form, and milk-form forms, and the like by diluting this composition by compounding water therein. Furthermore, the present invention provides a method for obtaining a topical composition in an arbitrary form by compounding water and a bioactive substance in this composition.

Means to Resolve the Problems

As a result of intensive investigation aimed at achieving the above objects, the present inventors arrived at the present invention. Specifically, the objects of the present invention are achieved by: a thickening agent or gelling agent for an oil-based raw material, the thickening agent or gelling agent comprising a novel co-modified organopolysiloxane having a group that has a siloxane dendron structure and a hydrophilic group such as a polyether group or the like in the molecule; and a topical composition or cosmetic composition comprising the same. Furthermore, the objects of the present invention are achieved by a method for producing a topical composition or cosmetic composition by using the thickening agent or gelling agent for an oil-based raw material or a gel composition.

The objects of the present invention are more preferably achieved by a thickening agent or gelling agent for an oil-based raw material comprising a high molecular weight hydrophilic silicone having a siloxane dendron structure and a tetraglycerin structure as a hydrophilic group, and by a gel composition. The objects are preferably achieved by a thickening agent or gelling agent comprising (B) a powder or colorant and (C) at least one component selected from a silicone-based surfactant (with the exception of compounds corresponding to component (A)), a crosslinking organopolysiloxane, a silicone resin, an acryl silicone dendrimer copolymer, a polyamide-modified silicone, and an alkyl-modified silicone resin wax.

More specifically, an object of the present invention is achieved by: a thickening agent or gelling agent for an oil-based raw material and a topical composition, especially a cosmetic composition, comprising the thickening agent or gelling agent, expressed by the following general formula (1):

wherein the thickening agent or gelling agent has a hydrophilic group and a group having a siloxane dendron structure and comprises a co-modified organopolysiloxane preferably having a degree of polymerization of not lower than 200.

The first object of the present invention is achieved by a thickening agent or gelling agent for an oil-based raw material comprising a co-modified organopolysiloxane having a group that has a siloxane dendron structure and a hydrophilic group, expressed by the following general formula (1):

and a topical composition, especially a cosmetic composition, comprising the thickening agent or gelling agent In the general formula (1), $R^1$ is a monovalent organic group (with the exception of groups corresponding to L1 and Q) or a hydrogen atom, and $L^1$ is a silylalkyl group having a siloxane dendron structure expressed by the following general formula (2) when i=1.

General Formula (2):

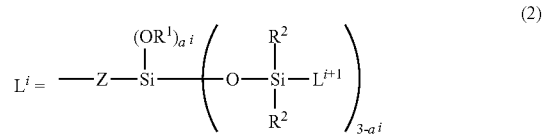

In general formula (2), $R^1$ is synonymous with the groups described above, $R^2$ is an alkyl group having 1 to 6 carbons or a phenyl group, and Z is a divalent organic group. i represents a generation of the silylalkyl group represented by $L^i$, and is an integer of 1 to c when c is a number of generations that is a number of repetitions of the silylalkyl group. The number of generations c is an integer from 1 to 10, and $L^{i+1}$ is the silylalkyl group when i is less than c and is a methyl group or a phenyl group when i=c. $a^i$ is a number in a range of 0 to 3; and $R^1$ is a group that is synonymous with that described above and, in the general formula (2), is preferably a hydrogen atom, or a substituted or unsubstituted monovalent hydrocarbon group having from 1 to 30 carbons.

In the general formula (1), Q is a hydrophilic group bonded to the silicon atom via a linking group that is at least divalent, and comprises at least one hydrophilic unit selected from hydrophilic units expressed by the following structural formulae (3-1) to (3-4).

In structural formula 3-1, r is a number in a range of 1 to 6.

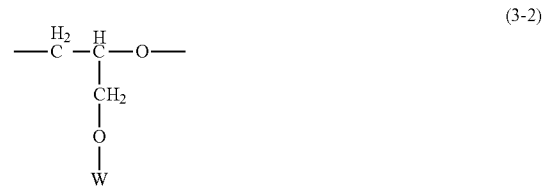

In structural formula 3-2, W is a hydrogen atom or an alkyl group having from 1 to 20 carbons.

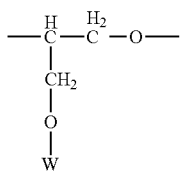
(3-3)

In structural formula 3-3, W is synonymous with the group described above.

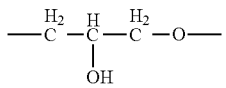
(3-4)

In the general formula (1), a, b, and c are in ranges so that $1.0 \leq a \leq 2.5$, $0.001 \leq b \leq 1.5$, and $0.001 \leq c \leq 1.5$.

More preferably, the object described above is achieved by a thickening agent or gelling agent for an oil-based raw material and a gel cosmetic composition, the thickening agent or gelling agent comprising a high molecular weight co-modified organopolysiloxane that is a co-modified organopolysiloxane which is expressed by structural formula (1-1) below and which has at least one silylalkyl group having a siloxane dendron structure per molecule, wherein a group derived from a polyglycerin (a group having a tetraglycerin structure is particularly preferable) is selected as the hydrophilic group (Q), and the numbers expressed by n1, n2, and n3, which indicate the degrees of polymerization of the following organosiloxane units, fall within the following ranges.

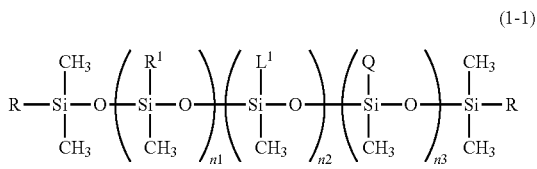
(1-1)

In structural formula (1-1), $R^1$, $L^1$, and Q are synonymous with the groups described above, and R is a group selected from $R^1$, $L^1$, and Q. n1, n2, and n3 are in ranges so that $200 \leq n1 \leq 1000$, $1 \leq n2 \leq 50$, and $0 \leq n3 \leq 20$; and when n3=0, at least one R is Q.

More specifically, the object described above is achieved by an invention of a thickening agent or gelling agent for an oil-based raw material, the thickening agent or gelling agent comprising a co-modified organopolysiloxane having a group that has a siloxane dendron structure and a hydrophilic group, described in [1] to [11] below.

[1] A thickening agent or gelling agent for an oil-based raw material, the thickening agent or gelling agent comprising (A) a co-modified organopolysiloxane which has a hydrophilic group and a group having a siloxane dendron structure and which is expressed by general formula (1) above.

[2] The thickening agent or gelling agent for an oil-based raw material according to [1], wherein the component (A) is a co-modified organopolysiloxane which is expressed by structural formula (1-1) above and which has at least one silylalkyl group having a siloxane dendron structure per molecule.

[3] The thickening agent or gelling agent for an oil-based raw material according to [1] or [2], wherein the component (A) is a co-modified organopolysiloxane such that, in general formula (1) or structural formula (1-1), $L^1$ is a functional group expressed by general formula (2-1) or general formula (2-2) below.

General Formula (2-1):

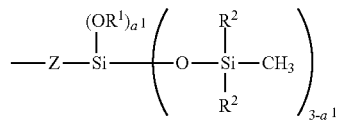
(2-1)

General Formula (2-2):

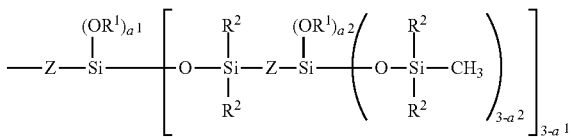
(2-2)

In these general formulae, $R^1$, $R^2$, and Z are synonymous with the groups described above, and $a^1$ and $a^2$ are each independently numbers in a range of 0 to 3.

[4] The thickening agent or gelling agent for an oil-based raw material according to any one of [1] to [3], wherein the component (A) is a co-modified organopolysiloxane expressed by structural formula (1-1-1) or structural formula (1-1-2) below.

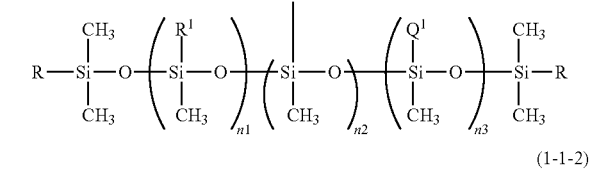
(1-1-1)

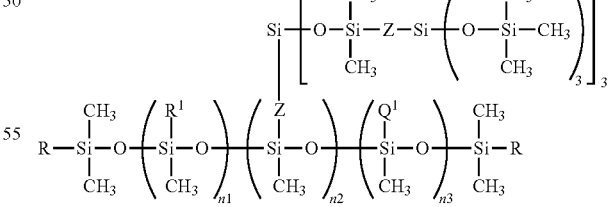
(1-1-2)

In these structural formulae, Z and $R^1$ are groups that are synonymous with those described above; R is a group selected from $R^1$, the $L^1$, and $Q^1$, described hereinafter. n1, n2, and n3 are numbers that fall within the numerical ranges $200 \leq n1 \leq 1000$, $1 \leq n2 \leq 50$, and $0 \leq n3 \leq 20$, and when n3=0, at least one R is $Q^1$.

$Q^1$ are each independently a hydrophilic group bonded to a silicon atom via a linking group that is at least divalent, comprising at least one linearly bonded hydrophilic unit selected from hydrophilic units expressed by the above structural formulae (3-1) to (3-4); or $Q^1$ are each independently a hydrophilic group bonded to the silicon atom via a linking group that is at least divalent, comprising not less than two of at least one hydrophilic unit selected from the hydrophilic units expressed by structural formula (3-1) to (3-4) above, and has a branch unit selected from groups expressed by structural formulae (3-5) to (3-7) below.

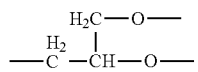 (3-5)

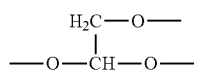 (3-6)

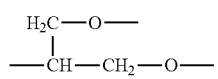 (3-7)

[5] The thickening agent or gelling agent for an oil-based raw material according to any one of [1] to [4], wherein the hydrophilic group Q or $Q^1$ is a hydrophilic group expressed by structural formulae (4-1), (4-2), (4-3), or (4-4) below.

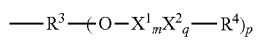 (4-1)

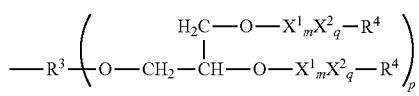 (4-2)

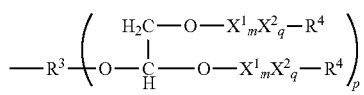 (4-3)

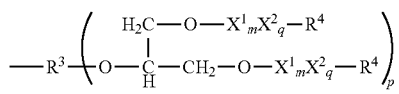 (4-4)

In these structural formulae, $R^3$ is an organic group having (p+1) valency, and p is a number that is greater than or equal to 1 and less than or equal 3. $X^1$ are each independently at least one hydrophilic unit selected from the hydrophilic units expressed by general formulae (3-2-1) to (3-4-1) below, and m is a number in a range of 3 to 5.

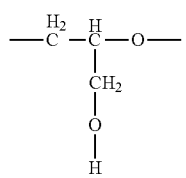 (3-2-1)

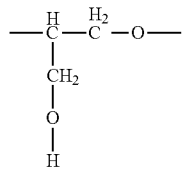 (3-3-1)

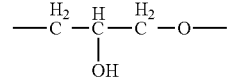 (3-4-1)

In these general formulae, $X^2$ is a hydrophilic unit expressed by structural formula (3-1) below, and q is a number in a range of 0 to 50. The manner in which $X^1$ and $X^2$ are each independently bonded is block or random.

—$C_rH_{2r}$—O— (3-1)

In structural formula (3-1), r is a number in a range of 1 to 6; and $R^4$ is a hydrogen atom or a group selected from the group consisting of glycidyl groups, acyl groups, and alkyl groups having from 1 to 20 carbons.

[6] The thickening agent or gelling agent for an oil-based raw material according to any one of [1] to [5], wherein the hydrophilic group Q or $Q^1$ is a hydrophilic group derived from a polyglycerin expressed by structural formula (4-1-1) below.

 (4-1-1)

In structural formula (4-1-1), $R^{3'}$ is a divalent organic group and $X^1$ are each independently at least one hydrophilic unit selected from the hydrophilic units expressed by general formulae (3-2-1) to (3-4-1) above, and m is a number in a range of 3 to 5. $R^4$ is a hydrogen atom or a group selected from the group consisting of glycidyl groups, acyl groups, and alkyl groups having from 1 to 20 carbons.

[7] The thickening agent or gelling agent for an oil-based raw material according to any one of [1] to [6], wherein the hydrophilic group Q or $Q^1$ is a hydrophilic group derived from a tetraglycerin.

[8] The thickening agent or gelling agent for an oil-based raw material according to any one of [1] to [7], further comprising (B) a powder or colorant.

[9] The thickening agent or gelling agent for an oil-based raw material according to any one of [1] to [8], further comprising (C) at least one component selected from a silicone-based surfactant (with the exception of compounds corresponding to component (A)), a crosslinking organopolysiloxane, a silicone resin, an acryl silicone dendrimer copolymer, a polyamide-modified silicone, and an alkyl-modified silicone resin wax.

[10] The thickening agent or gelling agent for an oil-based raw material according to any one of [1] to [9], wherein the oil-based raw material is (D1) at least one type of oil agent selected from a solid oil, a paste-form oil, a silicone oil, a hydrocarbon oil, and an ester oil.

[11] The thickening agent or gelling agent for an oil-based raw material according to [8], wherein the component (B) is (B1) at least one type of powder or colorant selected from a silicone resin powder, a silicone rubber powder, an organic resin powder (with the exception of silicone resin powders), an organo-modified clay mineral, titanium oxide, zinc oxide, a titanated mica, a metal soap, an inorganic body pigment, and an inorganic coloration pigment.

Another object of the present invention is achieved by the invention of a gel composition comprising the co-modified organopolysiloxane, described in [12] to [16] below.

[12] A gel composition comprising from 30 to 80 wt. % of (D) an oil-based raw material, from 10 to 70 wt. % of the thickening agent or gelling agent for an oil-based raw material according to any one of [1] to [11], from 0 to 20 wt. % of (E) at least one type of compound selected from a lower monohydric alcohol and an organic polyhydric alcohol-based compound, and from 0 to 20 wt. % of water.

[13] The gel composition according to [12], further comprising (F) a UV absorber.

[14] The gel composition according to [12] or [13], further comprising
(G) at least one type of compound selected from a sucrose fatty acid ester and a polyglycerol fatty acid ester.

[15] The gel composition according to any one of [12] to [14], further comprising (H) an organic film-forming agent.

[16] The gel composition according to any one of [12] to [15], further comprising (J) at least one type of compound selected from the group comprising an amino acid and/or a salt thereof, an inorganic salt, an organic acid and/or a salt thereof, and a water-soluble polymer.

Likewise, another object of the present invention is achieved by a method of adjusting the transparency of an emulsion composition, comprising independently mixing an aqueous phase and an oil phase that contains the component (A) and oil-based raw material (D), and then emulsifying after adjusting so that the difference in refractive index between the two phases at 25° C. is 0.0020 units or lower.

Furthermore, another object of the present invention is achieved by an invention of a cosmetic composition comprising the thickening agent or gelling agent for an oil-based raw material or the gel composition, an invention of a topical composition comprising a bioactive substance, and an invention of production methods thereof, described in [17] to [25] below.

[17] A method for producing a cosmetic composition by compounding from 0.1 to 4,000 parts by weight of (E) water with 100 parts by weight of the gel composition according to any one of [12] to [16].

[18] A cosmetic composition obtained by compounding from 0.1 to 4,000 parts by weight of (E) water with 100 parts by weight of the gel composition according to any one of [12] to [16].

[19] A gel cosmetic composition comprising from 30 to 80 wt. % of (D) an oil-based raw material, from 20 to 60 wt. % of the thickening agent or gelling agent for an oil-based raw material according to [8] or [11], and from 0 to 20 wt. % of (E) water.

[20] A method for producing a topical composition by compounding from 0.1 to 4,000 parts by weight of (E) water and from 0.001 to 1.0 parts by weight of a bioactive substance with 100 parts by weight of the gel composition according to any one of [12] to [16].

[21] A topical composition obtained by compounding from 0.1 to 4,000 parts by weight of (E) water and from 0.001 to 1.0 parts by weight of a bioactive substance with 100 parts by weight of the gel composition according to any one of [12] to [16].

[22] A gel topical composition comprising from 30 to 80 wt. % of (D) an oil-based raw material, from 20 to 60 wt. % of the thickening agent or gelling agent for an oil-based raw material according to [8] or [11], from 0 to 20 wt. % of (D) at least one type of compound selected from a lower monohydric alcohol and an organic polyhydric alcohol-based compound, from 0 to 20 wt. % of (E) water, and from 0.001 to 1.0 parts by weight of a bioactive substance.

[23] The topical composition according to [21] or [22], wherein the bioactive substance is at least one type of bioactive substance selected from among an anti-inflammatory agent, an anti-aging agent, a skin-lightening agent, a hair regrowth agent, a hair growth promoter, a circulation promoter, an antimicrobial agent, a germicide, a vitamin, a wound healing accelerator, an irritation mitigation agent, an analgesic, a cell activating agent, and an enzyme.

[24] The cosmetic composition according to [18] or [19], wherein the form of the product is liquid, milk-form, cream-form, solid, paste-form, gel, powder-form, multi-layer, mousse-form, or spray-form.

[25] The topical composition according to any one of [21] to [23], wherein the form of the product is liquid, milk-form, cream-form, solid, paste-form, gel, powder-form, multi-layer, mousse-form, or spray-form.

Another object of the present invention is preferably achieved by a production method in which the thickening agent or gelling agent for an oil-based raw material is subjected to a hydrosilylation reaction with an organopolysiloxane having a silicon-bonded hydrogen atom and other raw materials. The manufacturing method is described in detail in [26] below.

[26] A method for producing the thickening agent or gelling agent for an oil-based raw material according to any one of [1] to [7], comprising subjecting the co-modified organopolysiloxane of component (A) to an addition reaction with an organopolysiloxane having a silicon-bonded hydrogen atom and a compound with a siloxane dendron structure having one carbon-carbon double bond at a molecular terminal represented by general formula (2') below (at an amount corresponding to less than or equal to 0.9 times the molar equivalent of silicon-bonded hydrogen atoms in component (A)) in the presence of (C) a hydrosilylation reaction catalyst; and, thereafter, further addition reacting (D) a hydrophilic compound having one alkenyl group at a molecular terminal.

General Formula (2'):

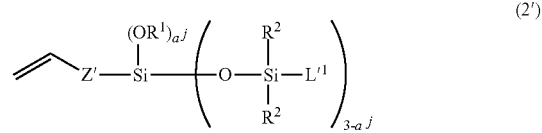

(2')

In general formula (2'), $L^1$ is a methyl group or, when j=1, is a silylalkyl group expressed by general formula (2") below, and Z' is a divalent organic group.

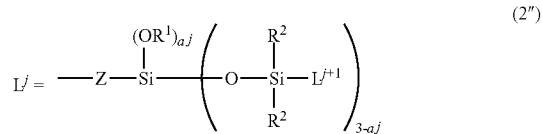

(2")

In general formula (2"), $R^2$ is a phenyl group or an alkyl group having from 1 to 6 carbons, and Z is a divalent organic group. j represents a generation of the silylalkyl group represented by $L^j$ and is an integer of 1 to c' when c' is a number of generations that is a number of repetitions of the silylalkyl group. The number of generations c' is an integer from 1 to 10, and $L^{j+1}$ is the silylalkyl group when j is less than c', and is a methyl group or a phenyl group when j=c'. $a^j$ is a number in a range from 0 to 3.

Effects of the Invention

The first problem to be addressed by an oil thickening agent, which relates to the degree of freedom with which the form of an oil agent can be controlled, another problem to be addressed, which relates to dispersing and solidifying a powder or colorant, yet another problem to be addressed, which relates to a gel composition, and yet another problem to be addressed, which relates to a method for producing a cosmetic composition or topical composition, as explained in the "Problems to be Solved by the Invention" section above, can all be preferably solved by the present invention. In particular, a cosmetic composition that optionally ensures optical transparency and has excellent storage stability when compounded in an emulsion-type gel cosmetic composition can be provided.

DETAILED DESCRIPTION OF THE INVENTION

The thickening agent or gelling agent for an oil-based raw material according to the present invention comprises a co-modified organopolysiloxane having a group that has a siloxane dendron structure and a hydrophilic group. Furthermore, the thickening agent or gelling agent for an oil-based raw material according to the present invention preferably has a group derived from a polyglycerin (a group having a tetraglycerin structure is particularly preferable) as the hydrophilic group and contains a high molecular weight co-modified organopolysiloxane.

Specifically, the co-modified organopolysiloxane is a co-modified organopolysiloxane expressed by general formula (1) below:

$$R^1_a L^1_b Q_c SiO_{(4-a-b-c)/2} \quad (1).$$

In general formula (1), a co-modified organopolysiloxane has a group having a siloxane dendron structure (-$L^1$) and a hydrophilic group (-Q), and the degree of polymerization of the organosiloxane unit is preferably 200 or higher. (Hereinafter, the group represented by $L^1$ in general formula (1), which is a silylalkyl group expressed by the following general formula (2) when i=1, is also referred to as the "carbosiloxane dendrimer" and the "silylalkyl group having a siloxane dendron structure".)

General Formula (2):

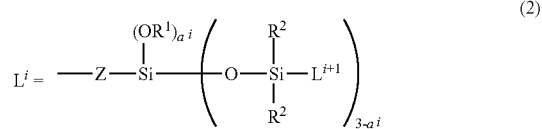

$$L^i = -Z-Si \begin{pmatrix} (OR^1)_{ai} \\ \\ \end{pmatrix} \begin{pmatrix} R^2 \\ | \\ O-Si-L^{i+1} \\ | \\ R^2 \end{pmatrix}_{3-ai} \quad (2)$$

In general formula 2, $R^1$ is a monovalent organic group or a hydrogen atom (with the exception of groups that are $L^1$ or Q), $R^2$ is an alkyl group having 1 to 6 carbons or a phenyl group, and Z is a divalent organic group. i represents a generation of the silylalkyl group represented by L', and is an integer of 1 to c when c is a number of generations that is a number of repetitions of the silylalkyl group. The number of generations c is an integer from 1 to 10, and $L^{i+1}$ is the silylalkyl group when i is less than c, and is a methyl group or a phenyl group when i=c. $a_i$ is a number in a range of 0 to 3.

First, a detailed description of the moieties $R^1$, $L^1$, and Q in general formula (1) will be given.

In general formula (1), $R^1$ is a monovalent organic group or a hydrogen atom. However, $R^1$ as a monovalent organic group does not include groups that correspond to $L^1$ or Q described above. Examples of the $R^1$ moiety include a hydrogen atom, a substituted or unsubstituted monovalent hydrocarbon group having from 1 to 30 carbons, an alkoxy group having from 1 to 30 carbons, a straight or branched polysiloxane chain, and the like. Examples of the substituted or unsubstituted monovalent hydrocarbon group include methyl groups, ethyl groups, propyl groups, butyl groups, pentyl groups, hexyl groups, heptyl groups, octyl groups, decyl groups, dodecyl groups, and other similar saturated aliphatic hydrocarbon groups; cyclopentyl groups, cyclohexyl groups, and similar saturated cycloaliphatic hydrocarbon groups; phenyl groups, tolyl groups, xylyl groups, naphthyl groups, and similar aromatic hydrocarbon groups; and groups wherein the hydrogen atoms bonded to the carbon atoms of these groups are substituted at least partially by fluorine or a similar halogen atom, or an organic group having an epoxy group, an acyl group, a carboxyl group, an amino group, a (meth)acryl group, a mercapto group, or the like. Examples of the alkoxy group include methoxy groups, ethoxy groups, isopropanoxy groups, higher alkoxy groups, and the like. The straight or branched polysiloxane chain is a straight or branched polysiloxane chain that does not correspond with $L^1$. Examples thereof include straight or branched polysiloxane chains having a polysiloxane chain structure that comprises a dimethylpolysiloxane unit that is bonded to the siloxane via a divalent linking group; where the dimethylpolysiloxane unit has a degree of polymerization of 1 to 100, and a silanol end, a trimethylsiloxy end, or an n-butyldimethylsiloxy end. Note that a portion of the methyl group of the polysiloxane chain may be substituted by a phenyl group, a fluorine or similar halogen atom, or an organic group including epoxy groups, acyl groups, carboxyl groups, amino groups, (meth)acryl groups, mercapto groups, and the like.

A modified group other than the group having a siloxane dendron structure (-$L^1$) and the hydrophilic group (-Q) can be introduced as $R^1$ or, alternately, the co-modified organopolysiloxane of the present invention can be designed in order to impart further functionality. Specifically, when $R^1$ is a substituted monovalent hydrocarbon group, a substituent can be suitably selected from the organic group examples described above in accordance with desired characteristics and uses. For example, when using the co-modified organopolysiloxane as a cosmetic raw material, a monovalent hydrocarbon group substituted with an amino group, an aminoethyl aminopropyl group, a carboxyl group, or the like can be selected as a substituent for the purpose of improving sensation during use, feeling to touch, and durability. Likewise, in addition to an alkyl group having from 1 to 4 carbons, such as a methyl group or an ethyl group, an alkyl group having from 8 to 20 carbons can be selected as a portion of the $R^1$ moiety for the purpose of improving sensation during use, feel on the skin, and affinity with other components of a so-called medium chain alkyl group or long chain alkyl group.

Of these, $R^1$ is preferably a monovalent hydrocarbon group or a monovalent fluorinated hydrocarbon group having from 1 to 20 carbons. Examples of the monovalent hydrocarbon group not having unsaturated aliphatic bonds belonging to the $R^1$ moiety include methyl groups, ethyl groups, propyl groups, butyl groups, pentyl groups, hexyl groups, and similar alkyl groups; phenyl groups, tolyl groups, xylyl groups, and similar aryl groups; and aralkyl groups such as benzyl groups. Examples of the monovalent fluorinated hydrocarbon group include trifluoropropyl groups, pentafluoroethyl groups, and similar perfluoroalkyl groups. From an industrial perspective, $R^1$ is preferably a methyl group, an ethyl group, or a phenyl group, and more preferably from 90 to 100 mol % of all the $R^1$ moieties are selected from methyl groups, ethyl groups, or phenyl groups.

In general formula (1), the group represented by $L^1$ is a silylalkyl group having a siloxane dendron structure, and is defined as the silylalkyl group expressed by general formula (2) when i=1. The silylalkyl group having a siloxane dendron structure has a structure where a carbosiloxane unit is extended in the form of a dendrimer and, thus, compared to a linear or simply branched polysiloxane unit, is a functional group that exhibits high water repellency; and, due to a well balanced combination with hydrophilic groups, the silylalkyl group can impart the co-modified organopolysiloxane according to the present invention with an excellent oil agent component thickening effect and gelling performance. Additionally, the silylalkyl group having a siloxane dendron structure is chemically stable, and for this reason, the silylalkyl group is a functional group providing advantageous characteristics such as usability in combination with a wide range of cosmetic composition-use components.

In general formula (2), $R^2$ is a phenyl group or an alkyl group having from 1 to 6 carbons. Examples of the alkyl group having from 1 to 6 carbons include methyl, ethyl, n-propyl, i-propyl, n-butyl, i-butyl, s-butyl, pentyl, neopentyl, cyclopentyl, hexyl, and similar straight, branched, or cyclic alkyl groups.

In general formula (2), i represents a generation of the silylalkyl group represented by $L^i$, and is an integer of 1 to c when c is a number of generations that is a number of repetitions of the silylalkyl group. The number of generations c is an integer from 1 to 10, and $L^{i+1}$ is the silylalkyl group when i is less than c and, is a methyl group or a phenyl group when i=c. In particular, $L^i$ is preferably a methyl group when i=c. $a^i$ is a number in a range of 0 to 3.

From a technical standpoint, the number of generations c is preferably an integer from 1 to 3, and more preferably is 1 or 2. In each of the number of generations, the group represented by $L^1$ is expressed as follows. In this formula, $R^2$ and Z are synonymous with the groups described above.

When the number of generations c=1, $L^1$ is expressed by the following general formula (2-1).

General Formula (2-1):

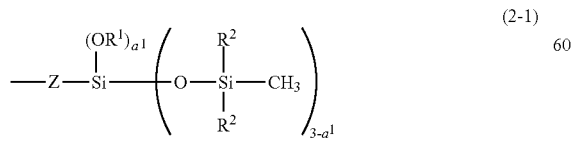

When the number of generations c=2, $L^1$ is expressed by the following general formula (2-2).

General Formula (2-2):

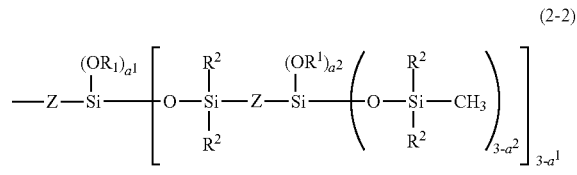

When the number of generations c=3, $L^1$ is expressed by the following general formula (2-3).

General Formula (2-3):

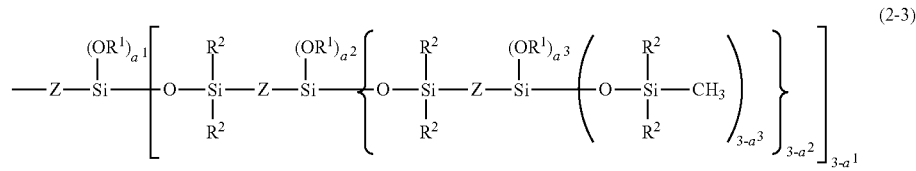

In formula (2), $a^i$ are each independently a number in a range from 0 to 3 and, in a structure expressed by formulae (2-1) to (2-3) where the number of generations is from 1 to 3, $a^1$, $a^2$, and $a^3$ are each independently a number in a range from 0 to 3. The $a^i$ moieties are preferably a number in a range from 0 to 1 and more preferably the $a^i$ moieties are 0.

In general formulae (2) and (2-1) to (2-3), Z are each independently a divalent organic group, and specific examples thereof include a divalent organic group formed by addition-reacting a silicon-bonded hydrogen atom and a functional group having an unsaturated hydrocarbon group such as an alkenyl group, an acryloxy group, a methacryloxy group, or the like at the terminal. Depending on the method for introducing the silylalkyl group having a siloxane dendron structure, the functional group can be appropriately selected and is not restricted to the functional groups described above. More specifically, Z are each independently a group selected from divalent organic groups expressed by the following general formulae (5-1) to (5-7). Of these, the Z in $L^1$ is preferably a divalent organic group expressed by general formula (5-1) that is introduced by a reaction between a silicon-bonded hydrogen atom and an alkenyl group. Likewise, Z is preferably a divalent organic group expressed by general formula (5-3) that is introduced by a reaction between a silicon-bonded hydrogen atom and an unsaturated carboxylic ester group. On the other hand, in the silylalkyl group represented by $L^i$ in which the number of generations c is 2 or more, and $L^i$ is $L^2$ to $L^c$, Z is preferably an alkylene group having from 2 to 10 carbons, more preferably a group selected from an ethylene group, a propylene group, a methylethylene group, and a hexylene group, and most preferably an ethylene group.

$$—R^6— \qquad (5\text{-}1)$$

$$—R^6—\overset{\overset{O}{\|}}{C}— \qquad (5\text{-}2)$$

$$—R^6—\overset{\overset{O}{\|}}{C}—O—R^6— \qquad (5\text{-}3)$$

-continued

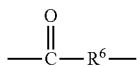  (5-4)

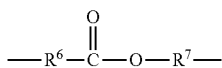  (5-5)

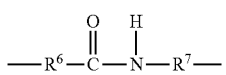  (5-6)

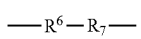  (5-7)

In these formulae (5-1) to (5-7), $R^6$ may have a substituent, and are each independently a straight or branched chain alkylene group or alkenylene group having from 2 to 22 carbons, or an arylene group having from 6 to 22 carbons. More specifically, examples of $R^6$ include an ethylene group, a propylene group, a butylene group, a hexylene group, and similar straight alkylene groups; a methylmethylene group, a methylethylene group, a 1-methylpentylene group, a 1,4-dimethylbutylene group, and similar branched alkylene groups. $R^6$ is preferably a group selected from an ethylene group, a propylene group, a methylethylene group, and a hexylene group.

In formulae (5-5) to (5-7), $R^7$ is a group selected from divalent organic groups expressed by the following formulae.

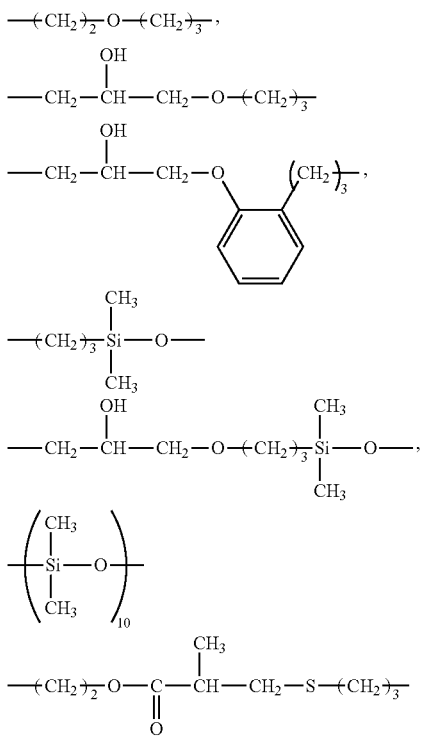

In general formula (1), Q is defined as a hydrophilic group bonded to the silicon atom via a linking group that is at least divalent, and comprises at least one hydrophilic unit selected from hydrophilic units expressed by the following structural formulae (3-1) to (3-4). Q as the hydrophilic group is a portion that imparts hydrophilicity to the co-modified orga-nopolysiloxane according to the present application and, generally, is a functional group derived from a hydrophilic compound. Preferable examples of Q as defined above include at least monovalent alcohols, polyether-based compounds, polyglycerin-based compounds, polyglycidyl ether-based compounds, and functional groups derived from hydrophilic sugars, that may be partially capped at the molecular end by a hydrocarbon. In the invention of the present application, Q is preferably a group derived from a polyglycerin, and especially a hydrophilic group having a tetraglycerin structure, from the perspective of an oil agent thickening and gelling effect.

Specifically, Q is a hydrophilic group bonded to the silicon atom via a linking group that is at least divalent, and comprises at least one hydrophilic unit selected from hydrophilic units expressed by the following structural formulae (3-1) to (3-4).

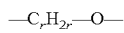  (3-1)

The hydrophilic unit expressed by formula (3-1) is an oxyalkylene unit. In this formula, r is a number in a range from 1 to 6, and is preferably a number in a range from 2 to 4. The hydrophilic unit expressed by formula (3-1) can have 1 or more hydrophilic groups (Q).

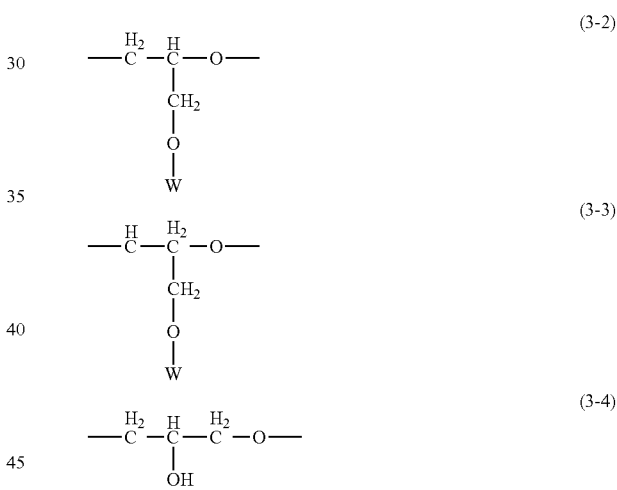

In formulae (3-2) to (3-4), W is a hydrogen atom or an alkyl group having from 1 to 20 carbons, and preferably is a hydrogen atom. Particularly, when W is a hydrogen atom, oxidation in air does not occur easily, and aldehydes such as formaldehyde and the like, and antigenic compounds such as formate esters and the like, are not easily produced over time while in storage. Therefore, when W is a hydrogen atom, there is a benefit of high environmental compatibility.

The hydrophilic units expressed by structural formulae (3-2) to (3-4) are hydrophilic units included in a hydrophilic group derived from a hydrophilic compound selected principally from polyhydric alcohols including glycerin, polyglycerins (also called "polyglycerols"), and polyglycidyl ethers or compounds in which terminal hydroxyl groups thereof are partially capped by hydrocarbon groups. However, the hydrophilic units are not limited thereto.

In general formula (1), Q may be, for example, a hydrophilic group that does not have a branched structure such as a straight polyoxyalkylene group, and may also be a hydrophilic group that has a partial branched structure in the functional group such as a polyglycerol group or a polyglycidylether group.

More specifically, Q may be a hydrophilic segment bonded to the silicon atom via a linking group that is at least divalent, comprising at least one linearly bonded hydrophilic unit selected from hydrophilic units expressed by the following structural formulae (3-1) to (3-4). Similarly, Q may be a hydrophilic segment bonded to the silicon atom via a linking group that is at least divalent, comprising not less than one of at least one hydrophilic unit selected from hydrophilic units expressed by structural formulae (3-1) to (3-4) above, and a branch unit selected from groups expressed by structural formulae (3-5) to (3-7) below.

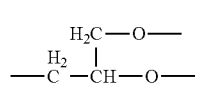
(3-5)

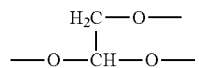
(3-6)

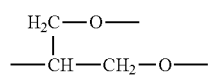
(3-7)

In structural formulae (3-5) to (3-7), the at least one hydrophilic unit selected from the hydrophilic units expressed by the general formulae (3-1) to (3-4) are each independently bonded to the two oxygen atoms. The hydrophilic unit may further be bonded to a branch unit selected from groups expressed by structural formulae (3-5) to (3-7). Moreover the hydrophilic unit may be formed so as to have a dendroid-shape polyether structure, a polyglycerol structure, or a polyglycidyl ether structure obtained by branching into multiple generations. For example, the structure of a hydrophilic group Q which has one branch unit expressed by structural formula (3-5) and two branch units expressed by structural formula (3-7) and which is branched in a dendritic manner is shown below, but it goes without saying that dendroid-shape polyether structures, polyglycerol structures and polyglycidyl ether structures are not limited to this example.

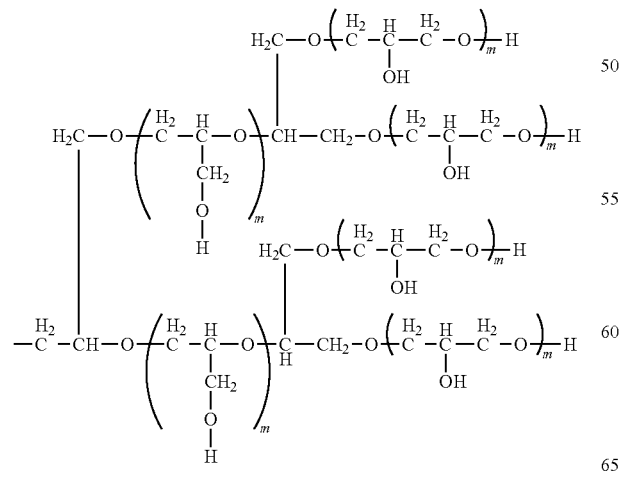

In the formula, m is a number in a range of 1 to 50.

The linking group that is at least divalent is a bonding site with respect to the silicon atom included in the hydrophilic group (Q), and a structure thereof is not particularly limited. Examples thereof include, ethylene groups, propylene groups, butylene groups, hexylene groups, and similar alkylene groups; ethylene phenylene groups, propylene phenylene groups, and similar alkylene phenylene groups; ethylene benzylene groups and similar alkylene aralkylene groups; ethyleneoxy phenylene groups, propyleneoxy phenylene groups, and similar alkyleneoxy phenylene groups; methyleneoxy benzylene groups, ethyleneoxy benzylene groups, propyleneoxy benzylene groups, and similar alkyleneoxy benzylene groups; and, furthermore, groups described below. Note that there are preferably from 0 to 3, and more preferably 0 or 1, ether bonds in the linking group that is at least divalent.

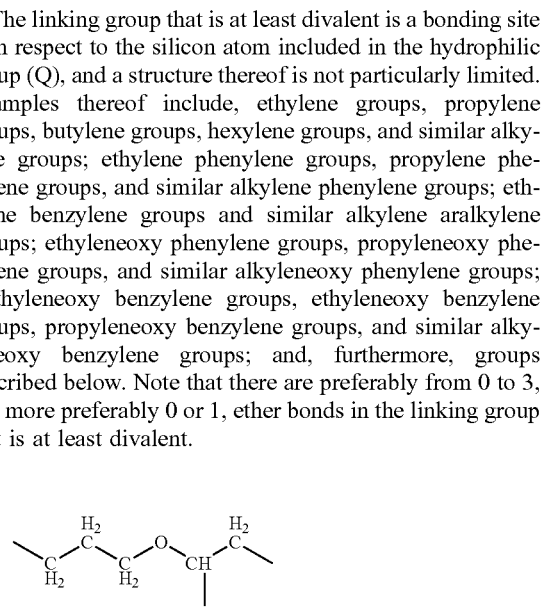

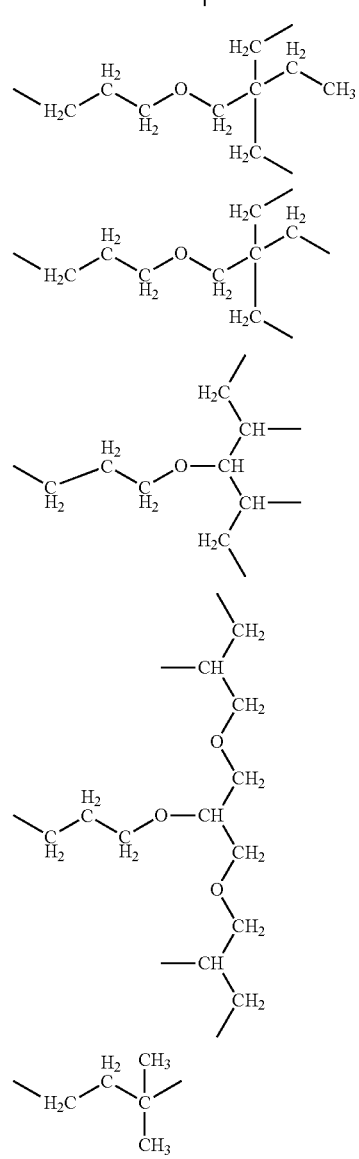

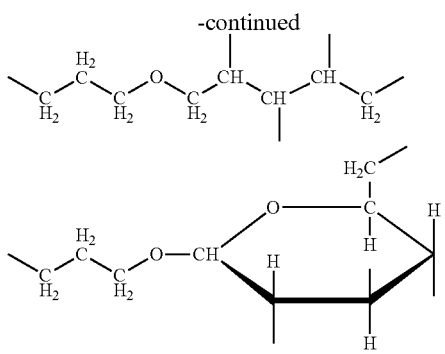

More preferably, Q is a hydrophilic group expressed by structural formulae (4-1) to (4-4) below, and these are generally hydrophilic groups derived from polyglycerin-based compounds.

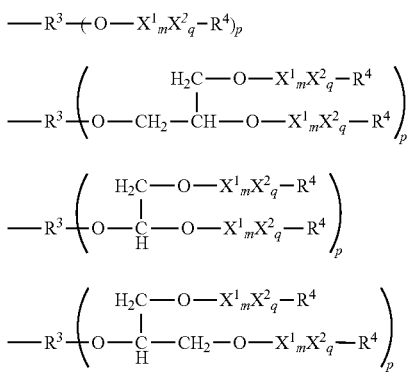

In formulae (4-1) to (4-4), $R^3$ is an organic group having (p+1) valency, and p is a number that is greater than or equal to 1 and less than or equal to 3. Examples of $R^3$ include a group that is synonymous with the linking group that is at least divalent.

It is more preferable that p is equal to 1 and that $R^3$ is a group selected from divalent organic groups expressed by the following general formulae.

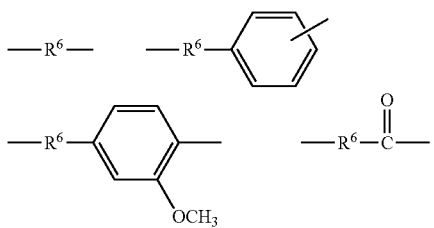

In these formulae, $R^6$ may have a substituent, and are each independently a straight or branched chain alkylene group or alkenylene group having from 2 to 22 carbons, or an arylene group having from 6 to 22 carbons.

$X^1$ are each independently at least one hydrophilic unit selected from the hydrophilic units expressed by general formulae (3-2-1) to (3-4-1) below, and m is a number in a range of 3 to 5, and is more preferably 4.

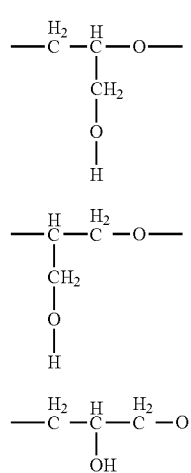

In these formulae, $X^2$ is an oxyalkylene unit expressed by structural formula (3-1) below, and q is a number in a range of 0 to 50.

$$—C_rH_{2r}—O— \quad (3-1)$$

In this formula, r is a number in a range of 1 to 6, and $X^2$ is preferably an oxyethylene unit or oxypropylene unit. In addition, in cases where $X^2$ is bonded continuously, one or more $X^2$ groups can be contained in Q as a polyoxyalkylene unit expressed by formula (3-1-1).

$$—(C_2H_4O)_{t1}(C_3H_6O)_{t2}— \quad (3-1-1)$$

In this formula, t1 and t2 are each numbers greater than or equal to 0, and (t1+t2) is a number in a range of 0 to 50 and preferably in a range of 0 to 30.

Here, the manner in which $X^1$ and $X^2$ are bonded can be block or random. That is, the hydrophilic group Q may be a hydrophilic group in which hydrophilic segments, which are obtained by bonding hydrophilic units expressed by general formulae (3-2-1) to (3-4-1) above in a block manner, are bonded to hydrophilic segments comprising polyoxyalkylene units, and may be a hydrophilic group in which these constituent units are bonded in a random manner. An example thereof is a bonding pattern such as $—(X^2)_{m1}—X^1—(X^2)_{m2}—X^1—$.

$R^4$ is a hydrogen atom or a group selected from the group consisting of glycidyl groups, acyl groups, and alkyl groups having from 1 to 20 carbons.

It is particularly preferable for the hydrophilic group Q to be a hydrophilic group derived from a polyglycerin expressed by structural formula (4-1-1) below from the perspective of thickening effect and gelling performance against oil agent components of the co-modified organopolysiloxane according to the present invention.

In the formula, $R^{3'}$ is a divalent organic group, and can be a group synonymous with those mentioned above. $X^1$ and $R^4$ are synonymous with the groups described above, and m is a number in a range of 3 to 5. It is particularly preferable for m to be 4 and for the group to have a tetraglycerin structure.

As mentioned above, it is preferable for the hydrophilic group Q to be a hydrophilic group derived from a polyglycerin-based compound from the perspective of thickening effect and gelling performance against oil agent components of the co-modified organopolysiloxane according to the present invention, and it is most preferable for hydrophilic group Q to be a hydrophilic group derived from a tetraglycerin. Specifically, a polyglycerin monoallyl ether or a polyglyceryl eugenol, which are examples of hydrophilic groups derived from polyglycerin-based compounds having a tetraglycerin structure, is preferable.

From the perspective of thickening effect and gelling performance against oil agent components, the co-modified organopolysiloxane expressed by general formula (1) above, which has a group having a siloxane dendron structure (-L¹) and a hydrophilic group (-Q), preferably has a degree of polymerization of the organosiloxane unit of 200 or higher and is preferably a co-modified organopolysiloxane having a straight chain polysiloxane structure expressed by structural formula (1-1) below.

Structural formula (1-1)

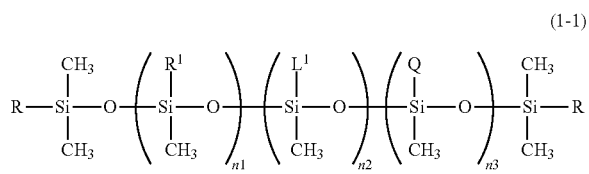

(1-1)

In the formula, $R^1$, $L^1$, and Q are each independently synonymous with the groups described above, and functional groups that are preferable as $L^1$ and Q are also synonymous with the groups described above. R is a group selected from among $R^1$, $L^1$, and Q. However, when n2=0, at least one R is $L^1$; and when n3=0, at least one R is Q. While 90 mol to 100% of all the $R^1$ moieties are preferably groups selected from methyl groups, ethyl groups, and phenyl groups, for the purpose of designing a co-modified organopolysiloxane with higher functional properties, a long chain alkyl group or a monovalent hydrocarbon group in which a portion of the carbon-bonded hydrogen is substituted by a fluorine atom or other halogen atom or another organic group can be selected as a portion of $R^1$. Such a long chain alkyl group or a monovalent hydrocarbon group is preferable. Additionally, a hydrogen atom (—H) that is bonded to a silicon atom may be included as a portion of $R^1$.

In the formula, (n1+n2+n3) is preferably a number in a range of 200 to 2,000, and more preferably a number in a range of 200 to 1,200. Specifically, the co-modified organopolysiloxane is preferably a high molecular weight organopolysiloxane having a degree of polymerization of 200 or higher from the perspective of thickening effect and gelling performance against oil agent components of the co-modified organopolysiloxane according to the present invention.

In particular, from the perspective of thickening effect and gelling performance against oil agent components of the co-modified organopolysiloxane according to the present invention, n1 is preferably a number in a range of 200 to 2,000, more preferably a number in a range of 200 to 1,000, and further preferably a number in a range of 250 to 800. From the perspective of the effect of the invention, n1 is most preferably a number in a range of 300 to 750.

It is preferable for n2 to be a number in a range of 1 to 250, and because it is preferable for a side chain moiety to have one or more groups having a siloxane dendron structure (-L¹) from the perspective of thickening effect and gelling performance against oil agent components, n2 is preferably a number in a range of 1 to 50, more preferably a number in a range of 3 to 35, and most preferably a number in a range of 5 to 25.

n3 is a number in a range of 0 to 100, preferably a number in a range of 0 to 50, and most preferably a number in a range of 0 to 20. From the perspective of thickening effect and gelling performance against oil agent components, however, if n3=0, at least one R is required to be $Q^1$. It is particularly preferable for n3 to be a number in a range of 1 to 20.

In particular, if the co-modified organopolysiloxane according to the present application is used as a thickening agent and gelling agent for an oil agent component, it is particularly preferable to use a co-modified organopolysiloxane expressed by structural formula (1-1-1) or (-1-1-2) below.

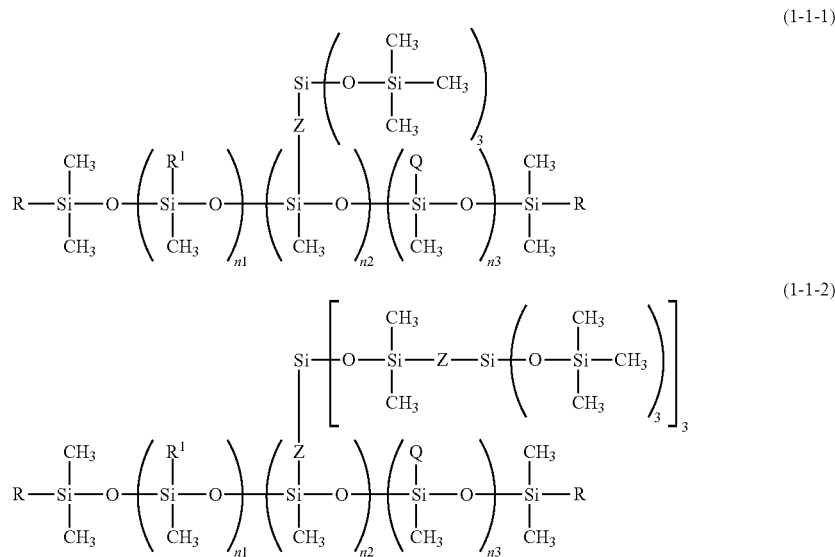

In these formulae, Z, $R^1$, and Q are groups that are synonymous with those described above; and R is a group selected from among $R^1$, the $L^1$, and Q. n1, n2, and n3 are numbers that fall within the numerical ranges $200 \leq n1 \leq 1000$, $1 \leq n2 \leq 50$, and $0 \leq n3 \leq 20$, and when $n3=0$, at least one R is Q.

The co-modified organopolysiloxane according to the present application described above can be obtained by addition-reacting a hydrophilic compound, which has a reactive functional group and a compound with a siloxane dendron structure having one carbon-carbon double bond at one end of the molecular chain, with an organopolysiloxane that has a reactive functional group. The type of addition reaction is not particularly limited but, from the standpoint of reaction control, purity, and yield, the addition reaction is preferably performed in the presence of a hydrosilylation reaction catalyst.

Specifically, co-modified organopolysiloxane according to the present application can be obtained by reacting at least (a) an organohydrogensiloxane expressed by the following general formula (1');

(in this formula, $R^1$, a, b, and c are the same as described above) and having a degree of polymerization of 200 or higher, (b) a hydrophilic derivative having one reactive unsaturated group in the molecule; and (c) a siloxane dendron having one reactive unsaturated group in the molecule in the presence of a hydrosilylation reaction catalyst.

Here, the co-modified organopolysiloxane according to the present application can be more preferably manufactured by reacting (b) the hydrophilic derivative having one reactive unsaturated group in the molecule, (c) the siloxane dendron having one reactive unsaturated group in the molecule, and (a) the organohydrogensiloxane expressed by the general formula (1') and having a degree of polymerization of 200 or higher together, while the component (b) and the component (c) are at least in a state of coexistence, or by subjecting at least (a) the organohydrogensiloxane and the component (c) (at an amount corresponding to 0.9 times the molar equivalent of silicon-bonded hydrogen atoms in component (a)) to an addition reaction and then subjecting the component (b) to a further addition reaction.

Preferable examples of the organohydrogensiloxane (a) expressed by general formula (1') include organohydrogensiloxanes expressed by the following structural formula (1-1)'.

Structural formula (1-1)':

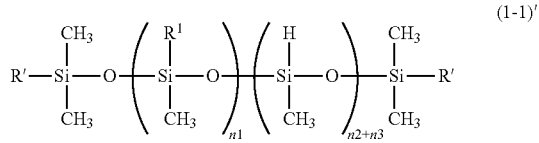

In this formula, $R^1$ are each independently a group that is synonymous with that described above, and R' is a group selected from $R^1$ and a hydrogen atom. n1, n2, and n3 are synonymous with the numbers described above. However, when (n2+n3)=0, at least one R' is a hydrogen atom.

The hydrophilic derivative (b) having one reactive unsaturated group in the molecule is a hydrophilic compound having a reactive functional group such as an alkenyl group on a molecular terminal, and examples thereof include a terminal allyl etherified polyglycerol-polyether copolymer, an allyl polyglycerol, an allyl polyglycidyl ether, and the like, and the hydrophilic derivative (b) can be synthesized according to a publicly known method. From the perspective of thickening effect and gelling performance against oil agent components of the co-modified organopolysiloxane according to the present invention, preferable examples of the hydrophilic derivative (b) include polyglycerin monoallyl ethers and polyglyceryl eugenols, and it is preferable for the hydrophilic group moiety to have a polyglycerin structure selected from among triglycerin, tetraglycerin, and pentaglycerin, and from the perspective of thickening effect and gelling performance, it is particularly preferable for the hydrophilic derivative (b) to be a hydrophilic compound having a tetraglycerin structure in the hydrophilic group moiety.

The siloxane dendron (c) having one reactive unsaturated group in the molecule is a compound expressed by the following general formula (2') that has a siloxane dendron structure having one carbon-carbon double bond at a molecular terminal.

General Formula (2'):

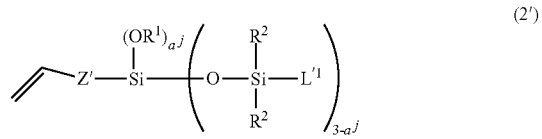

In general formula (2'), $L^{'1}$ is a methyl group or, when $j=1$, is a silylalkyl group expressed by following general formula (2"). Z' is a divalent organic group.

$$L^j = \quad \underset{\underset{R^2}{\overset{R^2}{|}}{\overset{(OR^1)_{a^j}}{|}}}{-Z-Si} \left( O - \underset{\underset{R^2}{|}}{\overset{R^2}{|}} Si - L^{j+1} \right)_{3-a^j} \quad (2'')$$

In general formula (2"), $R^2$ is a phenyl group or an alkyl group having from 1 to 6 carbons, and Z is a divalent organic group. j represents a generation of the silylalkyl group represented by $L^j$ and is an integer of 1 to c' when c' is a number of generations that is a number of repetitions of the silylalkyl group. The number of generations c' is an integer from 1 to 10, and $L^{j+1}$ is the silylalkyl group when j is less than c', and is a methyl group or a phenyl group when $j=c'$. $a^j$ is a number in a range of 0 to 3. $R^1$ is a group that is synonymous with that described above and, in the general formula (2"), is preferably a hydrogen atom, or a substituted or unsubstituted monovalent hydrocarbon group having from 1 to 30 carbons, and more preferably is a methyl group or a hydrogen atom.

The hydrosilylation reaction is preferably performed in the presence of a catalyst. Examples of the catalyst include platinum, ruthenium, rhodium, palladium, osmium, iridium, and similar compounds, and platinum compounds are particularly effective due to their high catalytic activity. Examples of the platinum compound include chloroplatinic acid; platinum metal; platinum metal supported on a carrier such as platinum supported on alumina, platinum supported on silica, platinum supported on carbon black, or the like; and a platinum complex such as platinum-vinylsiloxane complex, platinum phosphine complex, platinum-phosphite complex, platinum alcoholate catalyst, or the like. A usage amount of the catalyst is about 0.5 to 100 ppm in terms of platinum metal, when using a platinum catalyst.

Additionally, the crude co-modified organopolysiloxane obtained via the addition reaction described above can be refined by performing a deodorizing treatment by a hydrogenation reaction in the presence of a hydrogenation catalyst in a solvent or without a solvent. This refined product can be preferably used in cases where the co-modified organopolysiloxane is used in a topical composition application in which odor reduction and compatibility with other cosmetic composition components are needed. Moreover, the deodorizing treatment preferably has, as a pre-process or a post-process, a stripping process in which nitrogen gas is brought into contact with the crude co-modified organopolysiloxane or the hydrogenated product to remove light matter under reduced pressure.

In the hydrogenation reaction and stripping process, solvents, reaction conditions, pressure-reduction conditions, and the like used in the refining of conventional organopolysiloxane copolymers or polyether-modified silicones can be used or selected without any restrictions.

Alternately, the odor of the crude co-modified organopolysiloxane obtained via the addition reaction described above can easily be reduced by performing a stripping process in which light matter is removed by bringing nitrogen gas into contact with the crude product under reduced pressure, after an unreacted unsaturated compound is hydrolyzed by adding an acidic substance.

The co-modified organopolysiloxane according to the present invention that is obtained via the manufacturing method described above can be easily manufactured, and the degree of modification and type of modifying group can be easily controlled by simply changing the preparation of the raw material. Therefore, a functional molecular design is easy. Furthermore, the obtained co-modified organopolysiloxane is beneficial because it is chemically stable, has superior utility, and separation into two phases and sedimentation, or the like, of unreacted raw material following production occurs only minimally.

The novel co-modified organopolysiloxane according to the present invention has a silylalkyl group having a siloxane dendron structure, which exhibits high water repellency, and a hydrophilic group in the same molecule and is a polymer in which the degree of polymerization of an organosiloxane unit is 200 or higher, and is therefore extremely useful as a thickening agent or gelling agent for an oil-based raw material (D).

Here, the technical effects of "thickening" and "gelling" for the oil-based raw material (D) involve a continuous phenomenon, and it is therefore not necessarily possible to clearly distinguish between "thickening" and "gelling". In general, increasing the viscosity of a flowable oil agent that is a liquid at room temperature is known as "thickening", and a phenomenon whereby further thickening occurs, the state of the oil agent progresses to a viscous fluid such as a syrup-form, cream-form, or paste-form fluid, the fluidity of the oil agent almost disappears and the oil agent finally becomes a gel, or a semisolid to soft solid, is known as "gelling". By selecting the usage amount or structure, the novel co-modified organopolysiloxane according to the present invention can be preferably used as either a thickening agent or a gelling agent for an oil agent component. For example, by compounding a small amount of the co-modified organopolysiloxane according to the present invention in an oil agent component, the co-modified organopolysiloxane functions as a thickening agent, and by compounding a large amount of the co-modified organopolysiloxane, it is possible to gel the oil agent component.

In the field of topical compositions and cosmetic products, thickening or gelling an oil-based raw material has a significant effect or change on the appearance, formulation type, sensation during use, and dosage form of a topical composition or cosmetic, and techniques for thickening/gelling oil agent components are therefore extremely important. In addition, such techniques can provide cosmetic composition manufacturers with a degree of freedom by which it is possible to arbitrarily control the form of a cosmetic composition from liquid to syrup-form, cream-form, paste-form, gel, solid, and the like, and techniques for thickening/gelling oil-based raw materials are therefore extremely important.

The technical effect of thickening an oil-based raw material is particularly remarkable in the case of a polymer in which the organosiloxane unit in the novel co-modified organopolysiloxane according to the present invention has a degree of polymerization of 200 or higher, and it is possible to gel an oil agent even by using only a small amount of the co-modified organopolysiloxane. However, even in the case of a co-modified organopolysiloxane in which the organosiloxane unit has a degree of polymerization of about 30 to 150, it is possible to use the co-modified organopolysiloxane as a thickening agent for an oil agent component in a dosage form where gelation is not desirable, and such a co-modified organopolysiloxane is useful as a thickening agent for oil-based raw materials used in topical compositions and cosmetic compositions. Moreover, the degree of gelling can be controlled by adjusting the compounded amounts of these components. Furthermore, the novel co-modified organopolysiloxane according to the present application has particularly excellent compatibility with a variety of oil-based raw materials, and therefore has the advantage of not causing the problem of phase separation even when compounded with oil agents other than silicone-based oils.

The oil-based raw material (D) is a component that is thickened or gelled by the thickening agent or gelling agent of the novel co-modified organopolysiloxane according to the present invention, and is not particularly limited as long as this component is an oil-based raw material able to be used as a topical composition or a cosmetic composition. A particularly preferable oil-based raw material is an oil agent, and is preferably at least one type of oil agent (D1) selected from among solid oils, paste-form oils, silicone oils, hydrocarbon oils, and ester oils.

More preferably, the oil-based raw material to be thickened or gelled by the thickening agent or gelling agent according to the present invention is one or more types of oil agent selected from among (D1-1) a silicone oil, hydrocarbon oil, or ester oil that is a liquid at 5 to 100° C. Moreover, these oil agents may be thickened or gelled after being combined with one or two or more types of commonly known vegetable oils and fats, animal oils and fats, higher alcohols, liquid triglyceride fatty acid, and artificial sebums.

Specific examples of silicone oils of component (D) include straight chain organopolysiloxanes expressed by following general formula (1), cyclic organopolysiloxanes expressed by following general formula (2), and branched chain organopolysiloxanes expressed by following general formula (3).

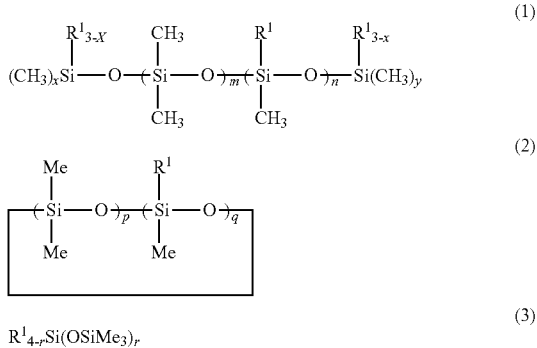

In formulae (1) to (3) relating to component (D) above, $R^1$ is a group selected from a hydrogen atom, a hydroxyl group, a monovalent unsubstituted or fluorine-substituted alkyl group having 2 to 30 carbons, an aryl group, an amino-substituted alkyl group, an alkoxy group, or a group expressed by (CH3)3SiOuSi(CH3)2CH2CH2—. Specific examples of $R^1$ include saturated aliphatic hydrocarbon groups such as ethyl groups, propyl groups, butyl groups, pentyl groups, hexyl groups, heptyl groups, octyl groups, decyl groups, dodecyl groups; unsaturated aliphatic hydrocarbon groups such as vinyl groups, allyl groups, hexenyl groups; saturated alicyclic hydrocarbon groups such as cyclopentyl groups and cyclohexyl groups; aromatic hydrocarbon groups such as phenyl groups, tolyl groups, and naphthyl groups; and groups in which the hydrogen atoms bonded to the carbon atoms of these groups are partially substituted by an organic group having a halogen atom, an epoxy group, a carboxyl group, an amino group, a (meth)acryl group, a mercapto group, and the like, or a group substituted by a trimethylsiloxy group and bonded via a divalent hydrocarbon group and/or a straight polydimethylsiloxane bond. m is an integer from 0 to 1,000, n is an integer from 0 to 1,000, and m+n is an integer from 1 to 2,000. x and y are 0, 1, 2, or 3. p and q are integers from 0 to 8 such that $3 \leq p+q \leq 8$. r is an integer from 1 to 4, and u is an integer from 0 to 500.

Examples of silicone oils having the structure described above include cyclic organopolysiloxanes such as hexamethyl cyclotrisiloxane (D3), octamethyl cyclotetrasiloxane (D4), decamethyl cyclopentasiloxane (D5), dodecamethyl cyclohexasiloxane (D6), 1,1-diethylhexamethyl cyclotetrasiloxane, phenylheptamethyl cyclotetrasiloxane, 1,1-diphenylhexamethyl cyclotetrasiloxane, 1,3,5,7-tetravinyltetramethyl cyclotetrasiloxane, 1,3,5,7-tetramethyl cyclotetrasiloxane, 1,3,5,7-tetracyclohexyltetramethyl cyclotetrasiloxane, tris(3,3,3-trifluoropropyl)trimethylcyclotrisiloxane, 1,3,5,7-tetra(3-methacryloxypropyl)tetramethyl cyclotetrasiloxane, 1,3,5,7-tetra(3-acryloxypropyl)tetramethyl cyclotetrasiloxane, 1,3,5,7-tetra(3-carboxypropyl) tetramethyl cyclotetrasiloxane, 1,3,5,7-tetra(3-vinyloxypropyl)tetramethyl cyclotetrasiloxane, 1,3,5,7-tetra(p-vinylphenyl)tetramethyl cyclotetrasiloxane, 1,3,5,7-tetra[3-(p-vinylphenyl)propyl]tetramethyl cyclotetrasiloxane, 1,3,5,7-tetra (N-acryloyl-N-methyl-3-aminopropyl)tetramethyl cyclotetrasiloxane, 1,3,5,7-tetra(N,N-bis(lauroyl)-3-aminopropyl)tetramethyl cyclotetrasiloxane, and the like. Examples of straight organopolysiloxanes include a dimethylpolysiloxane in which both molecular terminals are capped with trimethylsiloxy groups (dimethylsilicone with a low viscosity such as 2 cst or 6 cst to dimethylsilicone with a high viscosity such as 1,000,000 cst), an organohydrogenpolysiloxane, a methylphenylpolysiloxane in which both molecular terminals are capped with trimethylsiloxy groups, a copolymer of methylphenylsiloxane and dimethylsiloxane in which both molecular terminals are capped with trimethylsiloxy groups, a diphenylpolysiloxane in which both molecular terminals are capped with trimethylsiloxy groups, a copolymer of diphenylsiloxane and dimethylsiloxane in which both molecular terminals are capped with trimethylsiloxy groups, a trimethylpentaphenyltrisiloxane, a phenyl (trimethylsiloxy) siloxane, a methylalkylpolysiloxane in which both molecular terminals are capped with trimethylsiloxy groups, a copolymer of methylalkylsiloxane and dimethylpolysiloxane in which both molecular terminals are capped with trimethylsiloxy groups, a copolymer of methyl (3,3,3-trifluoropropyl) siloxane and dimethylsiloxane in which both molecular terminals are capped with trimethylsiloxy groups, an α,ω-dihydroxypolydimethylsiloxane, an α,ω-diethoxypolydimethylsiloxane, a 1,1,1,3,5,5,5-heptamethyl-3-octyltrisiloxane, a 1,1,1,3,5,5,5-heptamethyl-3-dodecyltrisiloxane, a 1,1,1,3,5,5,5-heptamethyl-3-hexadecyltrisiloxane, a tristrimethylsiloxymethylsilane, a tristrimethylsiloxyalkylsilane, a tetrakistrimethylsiloxysilane, a tetramethyl-1,3-dihydroxydisiloxane, an octamethyl-1,7-dihydroxytetrasiloxane, a hexamethyl-1,5-diethoxytrisiloxane, a hexamethyldisiloxane, an octamethyltrisiloxane, a higher alkoxy-modified silicone, a higher fatty acid-modified silicone, and the like.

Examples of the hydrocarbon oil of component (D) include liquid paraffin, light liquid isoparaffin, heavy liquid isoparaffin, vaseline, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene/polypropylene wax, squalane, squalene, pristane, polyisoprene, and the like.

Examples of the ester oil component (D) include hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyloctanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri-2-ethylhexanoate, trimethylolpropane tri-2-ethylhexanoate, ditrimethylolpropane triethylhexanoate, ditrimethylolpropane isostearate/sebacate, trimethylolpropane trioctanoate, trimethylolpropane triisostearate, diisopropyl adipate, diisobutyl adipate, 2-hexyldecyl adipate, di-2-heptylundecyl adipate, diisostearyl malate, hydrogenated castor oil monoisostearate, N-alkylglycol monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentylglycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearate, dipentaerythritol fatty acid ester, 2-hexyldecyl myristate, ethyl laurate, 2-octyldodecyl N-lauroyl-L-glutamate, di(cholesteryl/behenyl/octyldodecyl)N-lauroyl-L-glutamate, di(cholesteryl/octyldodecyl)N-lauroyl-L-glutamate, di(phytosteryl/behenyl/octyldodecyl) N-lauroyl-L-glutamate, di(phytosteryl/octyldodecyl)N-lauroyl-L-glutamate, isopropyl N-lauroylsarcosinate, diisostearyl malate, neopentylglycol dioctanoate, isodecyl neopentanoate, isotridecyl neopentanoate, isostearyl neopentanoate, isononyl isononanoate, isotridecyl isononanoate, octyl isononanoate, isotridecyl isononanoate, diethylpentanediol dineopentanoate, methylpentanediol dineopentanoate, tripropylene glycol dineopentanoate, octyldodecyl neodecanoate, 2-butyl-2-ethyl-1,3-propanediol dioctanoate, pentaerythrityl tetraoctanoate, pentaerythrityl hydrogenated rosin, pentaerythrityl triethylhexanoate, dipentaerythrityl (hydroxystearate/stearate/rosinate), polyglyceryl tetraisostearate, polyglyceryl-10 nonaisostearate, polyglyceryl-8 deca (erucate/isostearate/ricinoleate) (hexyldecanoic acid/sebacic acid) diglyceryl oligoester, glycol distearate (ethylene glycol distearate), diisopropyl dimer dilinoleate, diisostearyl dimer dilinoleate, di(isostearyl/phytosteryl)dimer dilinoleate, (phytosteryl/behenyl)dimer dilinoleate, (phytosteryl/isostearyl/cetyl/stearyl/behenyl)dimer dilinoleate, dimer dilinoleyl dimer dilinoleate, dimer dilinoleyl diisostearate, dimer dilinoleyl hydrogenated rosin condensate, dimer dilinoleic acid hardened castor oil, hydroxyalkyl dimer dilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri (caprylate/caprate), glyceryl tri (caprylate/caprate/myristate/stearate), hydrogenated rosin triglyceride (hydrogenated ester gum), rosin triglyceride (ester gum), glyceryl behenate eicosane dioate, glyceryl di-2-heptylundecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl ester of macadamia nut oil fatty acid, phytosteryl ester of macadamia nut oil fatty acid, phytosteryl isostearate, cholesteryl ester of soft lanolin fatty acid, cholesteryl ester of hard lanolin fatty acid, cholesteryl ester of long-chain branched fatty acid, cholesteryl ester of long-chain a-hydroxy fatty acid, octyldodecyl ricinoleate, octyldodecyl ester of lanolin fatty acid, octyldodecyl erucate, isostearic acid hardened castor oil, ethyl ester of avocado fatty acid, isopropyl ester of lanolin fatty acid, and the like.

Other oil-based raw materials include oils and fats, higher alcohols and higher fatty acids.

Examples of natural animal or vegetable oils and fats and semi-synthetic oils and fats include oils and fats such as avocado oil, linseed oil, almond oil, ibota wax, *perilla* oil, olive oil, cacao butter, kapok wax, kaya oil, carnauba wax, liver oil, candelilla wax, beef tallow, neatsfoot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shea butter, Chinese tung oil, cinnamon oil, jojoba wax, olive squalane, shellac wax, turtle oil, soybean oil, tea seed oil, *camellia* oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sunflower oil, grape oil, bayberry wax, jojoba oil, hydrogenated jojoba ester, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, reduced lanolin, lanolin alcohol, hard lanolin, lanolin acetate, lanolin fatty acid isopropyl ester, POE lanolin alcohol ether, POE lanolin alcohol acetate, lanolin fatty acid polyethylene glycol, POE hydrogenated lanolin alcohol ether, egg yolk oil, and the like. Herein, "POE" means "polyoxyethylene".

Examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, POE cholesterol ether, monostearyl glycerol ether (batyl alcohol), monooleyl glycerol ether (selachyl alcohol), and the like.

Examples of higher fatty acids include lauric acid, myristic acid, palmitic acid, stearic acid, behenic acid, undecylenic acid, oleic acid, linolic acid, linolenic acid, arachidonic acid, eicosapentaenoic acid (EPA), docosahexaenoic acid (DHA), isostearic acid, 12-hydroxystearic acid, and the like.

The thickening agent or gelling agent for an oil-based raw material of the present invention is compounded with the oil-based raw materials using a publicly known means so as to thicken or gel these oil-based raw materials and form a gel composition. Such thickened or gelled oil-based raw materials may further contain other components and, as described below, can be used as gel compositions that are compositions for producing cosmetic compositions (premixes), which are used to prepare water-based compositions.

In addition, the thickening agent or gelling agent for an oil-based raw material of the present invention can be added or uniformly dispersed in an already prepared topical composition or cosmetic composition so as to thicken or gel an oil-based raw material contained in the topical composition and the like. In particular, by thickening or gelling an oil agent in a cosmetic product, it is possible to obtain an appropriate viscosity and hardness for a cosmetic composition and improve the appearance, compounding properties and sensation during use thereof, and it is also possible to obtain a desired dosage form or cosmetic product type.

The thickening agent or gelling agent of the present invention is not particularly limited in terms of usage amount/compounding ratio, but this is preferably in a range from 1 to 99 wt. %, and more preferably in a range from 5 to 40 wt. %, of the weight of the entire material that contains an oil-based raw material. Moreover, because the degree of thickening varies according to the compounded amount of the thickening agent or gelling agent in the oil-based raw material, it is possible to control the viscosity of the entire material that contains an oil-based raw material and the hardness of the obtained gel composition (a characteristic of a cosmetic composition which can also be expressed as the visco-elastic or elastic texture of a gel) within desired ranges.

The co-modified organopolysiloxane according to the present invention can be used alone as a thickening agent or gelling agent for an oil-based raw material, but when used in combination with (B) a powder or colorant, in addition to an oil agent thickening/gelling effect, it is possible to stably and uniformly disperse these powders in the obtained thickened oil agent or oil-based gel substance and, in particular, it is possible to obtain a powder in oil dispersion in a mixed oil agent system which exhibits excellent stability in which precipitation or aggregation of the powders does not occur. Furthermore, it is possible to maintain an excellent cosmetic effect and a natural feeling on the skin with no discomfort for approximately 1 day after applying the powder in oil dispersion to the skin, and it is possible to achieve excellent dispersion/solidification performance.

Additionally, the component (B) is a powder and/or a colorant for use in a cosmetic composition, and this powder and/or colorant can be any powder provided that it is normally used in cosmetic compositions, and is not limited to form (sphere, bar, needle, plate, amorphous, spindle, or the like), particle size (aerosol, micro-particle, pigment-grade particle, or the like), or particle structure (porous, nonporous, or the like) thereof. When compounding the powder and/or colorant as a pigment, preferably one or two or more selected from an inorganic pigment powder, an organic pigment powder, and a resin powder having an average diameter in a range from 1 nm to 20 µm is compounded.

Examples of the powder or colorant include inorganic powders, organic powders, surfactant metal salt powders (metallic soaps), colored pigments, pearl pigments, organo-modified clay minerals, metal powder pigments, and the like. In addition, compound products of these pigments can also be used. Specific examples of inorganic powders include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, black mica, lithia mica, silicic acid, silicic acid anhydride, aluminum silicate, sodium silicate, magnesium sodium silicate, magnesium silicate, aluminum magnesium silicate, calcium silicate, barium silicate, strontium silicate, metal salts of tungstic acid, hydroxyapatite, vermiculite, higilite, bentonite, montmorillonite, hectorite, zeolite, ceramic powder, dicalcium phosphate, alumina, aluminum hydroxide, boron nitride, and the like. Examples of organic powders include polyamide powder, polyester powder, polyethylene powder, polypropylene powder, polystyrene powder, polyurethane powder, benzoguanamine powder, polymethylbenzoguanamine powder, polytetrafluoroethylene powder, poly (methyl methacrylate) powder, cellulose, silk powder, nylon powder, nylon 12, nylon 6, silicone powder, silicone rubber spherical powder, silicone rubber spherical powder that is surface-coated with polymethylsilsesquioxane, polymethylsilsesquioxane spherical powder, copolymers of styrene and acrylic acid, copolymers of divinylbenzene and styrene, vinyl resin, urea resin, phenol resin, fluorine resin, silicone resin, acrylic resin, melamine resin, epoxy resin, polycarbonate resin, macrocrystalline fiber powder, starch powder, lauroyl lysine, and the like. Examples of surfactant metal salt powders include zinc stearate, aluminum stearate, calcium stearate, magnesium stearate, zinc myristate, magnesium myristate, zinc palmitate, zinc laurate, zinc cetylphosphate, calcium cetylphosphate, sodium zinc cetylphosphate, and the like. Examples of colored pigments include inorganic red pigments such as red iron oxide, iron oxide, iron hydroxide, iron titanate, and the like; inorganic brown pigments such as gamma-iron oxide and the like; inorganic yellow pigments such as yellow iron oxide, ocher, and the like; inorganic black iron pigments such as black iron oxide, carbon black and the like; inorganic purple pigments such as manganese violet, cobalt violet, and the like; inorganic green pigments such as chromium hydroxide, chromium oxide, cobalt oxide, cobalt titanate, and the like; inorganic blue pigments such as Prussian blue, ultramarine blue, and the like; laked pigments of tar pigments such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207, and the like, laked pigments of natural pigments such as carminic acid, laccaic acid, carthamin, brazilin, crocin, and the like. Examples of pearl pigments include titanium oxide-coated mica, titanium mica, iron oxide-coated titanium mica, titanium oxide-coated mica, bismuth oxychloride, titanium oxide-coated bismuth oxychloride, titanium oxide-coated talc, fish scale foil, titanium oxide-coated colored mica, and the like. Examples of the metal powder pigment include powders of metals such as aluminum, gold, silver, copper, platinum, stainless steel, and the like.

In particular, a powder that absorbs and scatters ultraviolet light, such as microparticulate titanium oxide, microparticulate iron-containing titanium oxide, microparticulate zinc oxide, microparticulate cerium oxide, compound products thereof, and the like may be used as the inorganic powder. More specifically, an inorganic ultraviolet light blocking component may be compounded as an ultraviolet light scattering agent such as the inorganic powder pigments and metal powder pigments mentioned above. Examples thereof include metal oxides such as titanium oxide, zinc oxide, cerium oxide, titanium suboxide, iron-doped titanium oxides, and the like; metal hydroxides such as iron hydroxides and the like; metal flakes such as platy iron oxide, aluminum flake, and the like; and ceramics such as silicon carbide, and the like. Of these, at least one type of a material selected from fine particulate metal oxides and fine particulate metal hydroxides with an average particle size in a range from 1 to 100 nm is preferable.

Examples of the organo-modified clay mineral include dimethylbenzyl dodecylammonium montmorillonite clay, dimethyldioctadecylammonium montmorillonite clay, dimethylalkylammonium hectorite, benzyldimethylstearylammonium hectorite, distearyldimethylammonium chloride-treated aluminum magnesium silicate, and the like. Examples of commercially available products include Benton 27 (benzyldimethylstearylammonium chloride-treated hectorite, manufactured by Nationalred Co.), Benton 38 (distearyldimethylammonium chloride-treated hectorite, manufactured by Nationalred Co.), and the like.

The silicone rubber spherical powder (also known as a silicone elastomer spherical powder) preferably has a primary particle size in a range from 0.1 to 50 µm. Examples of commercially available products of the silicone rubber spherical powder include Trefil E-506S, Trefil E-508, 9701 Cosmetic Powder, and 9702 Powder, manufactured by Dow Corning Toray Co., Ltd., and the like. In addition, the silicone rubber spherical powder can also be used in the cosmetic composition of the present invention in the form of an aqueous dispersion liquid. Examples of commercially available products of the aqueous dispersion liquid include BY 29-129 and PF-2001 PIF Emulsion, manufactured by Dow Corning Toray Co., Ltd., and the like. Adding a powdered silicone elastomer to the cosmetic composition according to the present invention is advantageous because a feeling to touch that is substantial, such as that obtained when an oil agent is dispersed, is imparted, unevennesses of the skin are concealed, and, in contrast with oil agents, a natural impression is given due to oily shininess of the skin and oily texture being suppressed.

One or two or more types of the silicone elastomer can be compounded depending on the purpose thereof. A compounded amount of the silicone elastomer is preferably in a range from 0.05 to 25 wt. % and more preferably in a range from 0.1 to 15 wt. % of the entire cosmetic composition, depending on purpose and compounding intention.

Furthermore, these powders or colorants are preferably subjected to a water-repellent treatment. Additionally, a product can be used in which these powders and/or colorants are compounded together; or subjected to surface treatment using a general oil agent, a silicone compound other than the co-modified organopolysiloxane according to the present invention, a fluorine compound, a surfactant, or the like. One type thereof or two or more types thereof can be used, as necessary.

Examples of such water-repellent treatments include various treatments in which the powder and/or colorant is surface treated with a water repellency agent. Specific examples thereof include organosiloxane treatments such as a methylhydrogenpolysiloxane treatment, a silicone resin treatment, a silicone gum treatment, an acryl silicone treatment, a fluorinated silicone treatment, and the like; metallic soap treatments such as a zinc stearate treatment and the like; silane treatments such as a silane coupling agent treatment, an alkylsilane treatment, and the like; fluorine compound treatments such as a perfluoroalkylsilane treatment, a perfluoroalkyl phosphate treatment, a perfluoro polyether treatment, and the like; amino acid treatments such as an N-lauroyl-L-lysine treatment and the like; oil agent treatments such as a squalane treatment and the like; and acryl treatments such as an alkyl acrylate treatment and the like. One of the treatments described above can be used or a combination of two or more can be used.

Particularly preferable examples of these powders or colorants include (B1) at least one type of powder or colorant selected from among the group consisting of a silicone resin powder, a silicone rubber powder, an organic resin powder (with the exception of silicone resin powders), an organo-modified clay mineral, titanium oxide, zinc oxide, a titanated mica, a metal soap, an inorganic body pigment, and an inorganic coloration pigment. Because the co-modified organopolysiloxane according to the present invention exhibits good dispersion stability of a powder or colorant, in cases where a variety of pigments are used in combination with an oil agent, the hue, covering properties, and feeling to touch of a cosmetic composition can be easily adjusted without causing drawbacks such as aggregation or precipitation of a powder or a deterioration in feeling to touch. In particular, a case in which the co-modified organopolysiloxane according to the present invention is used in combination with a silicone-based powder such as a silicone resin powder or silicone rubber powder having excellent absorption capacity for an oil agent component or an organic resin powder such as a silk powder, nylon powder, poly(methyl methacrylate) powder, or polyethylene powder, in order to thicken or gel an oil-based raw material, has the advantage of being able to mitigate the strong oiliness inherent in oil-based cosmetic compositions and the like and achieve the effect of making the skin sensation/feeling more natural following application without imparting the powdery texture inherent in these powders.

The compounded amount of component (B) can be selected according to the dosage form or the type of cosmetic composition, but is preferably in a range from 0.1 to 99 wt. % relative to the overall gel composition comprising the oil-based raw material and the co-modified organopolysiloxane according to the present invention.

A gel composition that contains these powders or colorants can be used without further modification as a gel cosmetic composition, and the compounded amount thereof in the case of a gel cosmetic composition is preferably in a range from 10 to 50 wt. % of the overall cosmetic composition. In addition, when used as a solid gel cosmetic composition having low flowability, it is possible to compound the powder or colorant in a range from 50 to 80 wt. %.

It is possible to further compound (C) at least one component selected from a silicone-based surfactant (with the exception of compounds corresponding to component (A)), a crosslinking organopolysiloxane, a silicone resin, an acryl silicone dendrimer copolymer, a polyamide-modified silicone, an alkyl-modified silicone wax, and an alkyl-modified silicone resin wax to a gelling agent comprising the co-modified organopolysiloxane according to the present invention. These components (C) have excellent compatibility with mixtures of the co-modified organopolysiloxane according to the present invention and an oil-based raw material, and can be stably compounded in a gel composition.

The silicone-based surfactant is a silicone-based surfactant other than the co-modified organopolysiloxane according to the present invention. Such silicone-based surfactants are cleansing components or emulsifiers of oil agents, typical examples of which include polyoxyalkylene-modified silicones, polyglyceryl-modified silicones, glyceryl-modified silicones, sugar-modified silicones, fluorosurfactants, polyoxyethylene/polyoxypropylene block polymers, and alkylpolyoxyethylene/polyoxypropylene block polymer ethers. Preferable silicone-based surfactants include straight polyoxyalkylene-modified organopolysiloxanes (polyether-modified silicones in which a polyoxyalkylene group is bonded at a side chain and/or a terminal), block copolymerized type polyoxyalkylene/dimethylpolysiloxane copolymers, and straight polyoxyalkylene/alkyl-co-modified organopolysiloxanes (alkyl/polyether-modified silicones in which a polyoxyalkylene group and an alkyl group are bonded at a side chain and/or a terminal). Additional preferable examples of silicone-based surfactants include the specific elastomer silicone polyethers described in Japanese Patent No. 4080597 (Japanese Unexamined Patent Application Publication No. H-11-49957), Japanese Unexamined Patent Application Publication No. 2001-011281, and the like (examples of commercially available products include DC 9011 Silicone Elastomer Blend, manufactured by Dow Corning Corporation, in the USA).

The crosslinking organopolysiloxane is an organopolysiloxane having a structure in which the organopolysiloxane chain is three-dimensionally crosslinked via a reaction with a crosslinking component or the like, and preferably does not have a hydrophilic portion such as a polyoxyalkylene unit or the like, and is non-emulsifiable. Any crosslinking organopolysiloxane can be used without limitations to physical modes or preparation methods such as dilution, properties, and the like, provided that it is a crosslinking organopolysiloxane such as that described above. Particularly preferable examples include $\alpha,\omega$-diene crosslinking silicone elastomers (commercially available products include DC 9040 Silicone Elastomer Blend, DC 9041 Silicone Elastomer Blend, DC 9045 Silicone Elastomer Blend, and DC 9046 Silicone Elastomer Blend, manufactured by Dow Corning Corporation, in the USA) described in U.S. Pat. No. 5,654,362. Likewise, examples of partially crosslinking organopolysiloxane polymers include (dimethicone/vinyldimethicone) crosspolymers, (dimethicone/phenylvinyldimethicone) crosspolymers, (PEG-8 to 30/C6 to C30 alkyldimethicone) crosspolymers, (vinyldimethicone/C6 to C30 alkyldimethicone) crosspolymers, (dimethicone/polyglycerol) crosspolymers, and the like, using INCI names (International Nomenclature Cosmetic Ingredient labeling names).

However, in the case of being compounded as an emulsifiable crosslinking organopolysiloxane formed by crosslinking by means of a polyether compound as a component in a cosmetic composition, the co-modified organopolysiloxane according to the present invention functions as a surfactant or, alternately, a surfactant aid. For this reason, there is an advantage in that a uniform emulsification system can be formed. Furthermore, because the crosslinking organopolysiloxane functions as a surfactant, even when used in small amounts, a hydrous gel structure can be formed stably. This is advantageous because a hydrous cosmetic composition or emulsion cosmetic composition can be obtained that is soft and has superior water retention properties.

On the other hand, in the case of being compounded as a non-emulsifiable crosslinking organopolysiloxane, formed by crosslinking by means of an unsaturated hydrocarbon group such as a diene or an organopolysiloxane as a component, in a cosmetic composition, feel of adhesion to the skin can be improved. Furthermore, there are advantages in that excellent compatibility with other oil-based raw materials can be obtained, and the entire oil system can be uniformly and stably compounded in the cosmetic composition.

Preferable examples of silicone resins include solid silicone net-like compounds such as MQ resins, MDQ resin, MTQ resin, MDTQ resin, TD resin, TQ resin, and TDQ resin formed from any combination of a trialkylsiloxy unit (M unit), a dialkylsiloxy unit (D unit), a monoalkylsiloxy unit (T unit), and a tetrafunctional siloxy unit (Q unit). Note that the substituent on the silicon of these silicone resins may include a substituted alkyl group, a phenyl group, an aryl group, or the like, in addition to the alkyl group. Of these, from the standpoint of obtaining superior usability, fluorine-modified silicone resins, trimethylsiloxy silicic acid (MQ resin), and dimethylsiloxy group-containing trimethylsiloxy silicic acid (MDQ resin) are particularly preferable. Compounding the silicone resin in conjunction with the co-modified organopolysiloxane according to the present invention is useful because the following improvement effects can be obtained due to the compounding of the silicone resin: improvements in feeling to touch of the cosmetic composition, uniform adhesion to the applied area, and adhesion of the powder to the skin.

Specific preferable examples of acryl silicone dendrimer copolymers include a vinyl-based polymer having a carbosiloxane dendrimer structure in a side chain such as that described in Japanese Patent No. 4009382 (Japanese Unexamined Patent Application Publication No. 2000-063225). Examples of commercially available products thereof include FA4001 CM Silicone Acrylate, FA4002 ID Silicone Acrylate (manufactured by Dow Corning Toray Co., Ltd.), and the like. When compounding the acryl silicone dendrimer copolymer alone, superior film formability can be obtained. Therefore, by compounding the dendrimer copolymer in the cosmetic composition according to the present invention, a strong cosmetic coating film can be formed on the applied part, and cosmetic durability such as sebum resistance, rubbing resistance, and the like can be significantly improved.

By using the co-modified organopolysiloxane together with the acryl silicone dendrimer copolymer, there are advantages in that a surface protective property such as sebum resistance can be improved due to high water repellency provided by the carbosiloxane dendrimer structure; and at the same time, excellent feeling to touch and brightness are imparted when applying, and irregularities such as pores and wrinkles of the skin to which the cosmetic composition is applied can be effectively concealed due to the high emulsion stability of the present invention product being maintained. Moreover, the co-modified organopolysiloxane according to the present invention displays excellent miscibility with other oil agents, powders, the colorant, and the acryl silicone dendrimer copolymer and, therefore, there is an advantage in that makeup running or gathering on the skin can be controlled. Furthermore, when powders or colorants are treated in accordance with a conventional method by using the co-modified organopolysiloxane together with the acryl silicone dendrimer copolymer, a powder composition for use in a cosmetic composition with superior compounding stability can be prepared.

A compounded amount of the acryl silicone dendrimer copolymer can be suitably selected based on the purpose and compounding intent thereof, but is preferably in a range from 1 to 99 wt. % and more preferably in a range from 30 to 70 wt. % of the entire cosmetic composition.

Examples of the polyamide-modified silicone include the siloxane-based polyamide described in U.S. Pat. No. 5,981,680; and examples of commercially available products include 2-8178 Gellant, 2-8179 Gellant, and the like (manufactured by Dow Corning Corporation, in the USA). In the same way as oil-soluble gelling agents, such polyamide-modified silicones are useful as thickening/gelling agents for oil-based raw materials, and silicone oils in particular.

Compatibility with an oil agent such as a silicone oil or the like can be further improved by using a polyamide-modified silicone together with the co-modified organopolysiloxane of the present invention, and the cosmetic composition according to the present invention therefore delivers an excellent sense of stability and adhesion, and excellent spreading and setting when applied to the skin or hair. Additionally, there are advantages from a quality standpoint such that a glossy, sheer sensation, and superior luster can be provided, the viscosity or hardness (softness) of the entire cosmetic composition containing the oil-based raw material can be appropriately adjusted, and an oily sensation (oily and sticky feeling to touch) can be totally controlled. In addition, by using the co-modified organopolysiloxane of the present invention together with a polyamide-modified silicone, the dispersion stability of a perfume, a powder, and the like can be improved. Therefore, the obtained cosmetic composition is characterized by being able to maintain a uniform and fine cosmetic sensation for an extended period of time.

A compounded amount of the polyamide-modified silicone can be suitably selected based on the purpose and compounding intent thereof but, when using the polyamide-modified silicone as a gelling agent for an oil-based raw material, is in a range from 0.5 to 80 parts by weight and preferably in a range from 1 to 50 parts by weight per 100 parts by weight of the oil-based component such as the oil agent or the like.

The alkyl-modified silicone wax used in the cosmetic composition of the present invention depending on the purpose of the cosmetic composition needs only to be an alkyl-modified silicone wax in wax form at room temperature, and examples thereof include methyl (long chain alkyl) polysiloxanes having both molecular terminals capped with trimethylsiloxy groups, copolymers of a dimethylpolysiloxane having both molecular terminals capped with trimethylsiloxy groups and a methyl (long chain alkyl) siloxane, dimethylpolysiloxane modified with long chain alkyls at both terminals, and the like. Examples of commercially available products include AMS-C30 Cosmetic Wax, 2503 Cosmetic Wax, and the like (manufactured by Dow Corning Corporation, in the USA).

When using the co-modified organosiloxane according to the present invention in combination with the alkyl-modified silicone wax, compatibility with the oil-based raw material is improved, and superior formability and uniform dispersibility of the other components can be obtained and, thereby a cosmetic composition exhibiting superior storage stability over an extended period of time can be obtained. In particular, in a system containing a powder and/or a colorant, there is an advantage in that separation of the system including the alkyl-modified silicone wax, for the most part, does not occur, and an oil-based cosmetic composition having superior form-retaining strength and which spreads smoothly and uniformly when applied can be provided.

In the present invention, the alkyl-modified silicone wax preferably has a melting point of not lower than 60° C. because such will lead to cosmetic retainability effects and stability at high temperatures. A compounded amount thereof can be suitably selected based on the purpose and compounding intent thereof, and can be compounded in a range from 1 to 50 wt. % of the entire cosmetic composition. The compounded amount is preferably in a range from 5 to 40 wt. % because such leads to improvements in the formability and cosmetic retainability of the oil-based cosmetic composition. Additionally, the alkyl-modified silicone wax displays high compatibility with silicone oil having a long chain alkyl group such as the alkyl-modified silicone or the like and the crosslinking organopolysiloxanes and, therefore, is preferably used in combination with these optional components.

Examples of alkyl-modified silicone resin waxes include the silsesquioxane resin wax described in Japanese Patent Application (Translation of PCT Application) No. 2007-532754.

As a result of using the alkyl-modified silicone resin wax in combination with the organosiloxane copolymer of the present invention and compounding these in the cosmetic composition of the present invention, there are advantages of conditioning effects on skin and hair being improved and fine texture and a moisturized feeling to touch being imparted.

In the present invention, a compounded amount of the alkyl-modified silicone resin wax can be suitably selected based on the purpose and compounding intent thereof, and can be compounded in a range from 0.5 to 50 wt. % of the entire cosmetic composition. The compounded amount is preferably in a range from 1 to 30 wt. % in order to attain sebum durability and a fine texture feeling to touch of the cosmetic composition.

By using (A) the thickening agent or gelling agent for an oil-based raw material according to the present invention, optionally (B) a powder or colorant, optionally (C) at least one type of compound selected from among the group consisting of a silicone-based surfactant (with the exception of compounds corresponding to component (A)), a crosslinking organopolysiloxane, a silicone resin, an acryl silicone dendrimer copolymer, a polyamide-modified silicone, an alkyl-modified silicone wax, and an alkyl-modified silicone resin wax, and (D) an oil-based raw material to form a topical composition or cosmetic raw material that is a gel composition, and then diluting by blending water and an arbitrary amount of (E) at least one type of compound selected from among the group consisting of lower monohydric alcohols and organic polyhydric alcohol-based compounds in this gel composition, it is possible to provide a method for easily obtaining a cosmetic composition, and especially an emulsion cosmetic composition, in an arbitrary form having a lower viscosity than paste-like, cream-form, and milk-form forms, and the like.

Furthermore, it is possible to compound (F) a UV absorber, (G) at least one compound selected from among sucrose fatty acid esters and polyglycerol fatty acid esters, (H) an organic film-forming agent, or (J) at least one compound selected from among amino acids and/or salts thereof, inorganic salts, organic acids and/or salts thereof, and water-soluble polymers in the gel composition, and a gel composition comprising these components can be produced easily and stably.

Similarly, by using (A) the thickening agent or gelling agent for an oil-based raw material according to the present invention, optionally (B) a powder or colorant, and (D) an oil-based raw material to form a topical composition or cosmetic raw material that is a gel composition, and then diluting by blending water, an arbitrary amount of (E) at least one type of compound selected from among the group consisting of lower monohydric alcohols and organic polyhydric alcohol-based compounds, and (K) a bioactive substance in this gel composition, it is possible to provide a method for easily obtaining a cosmetic composition, and especially an emulsion cosmetic composition, in an arbitrary form having a lower viscosity than paste-form, cream-form, and milk-form forms, and the like.

The gel composition according to the present invention is a composition for producing a cosmetic composition (a premix), which is used to prepare a hydrous cosmetic composition, and has the advantage of being able to form a stable hydrous cosmetic composition by using a simple stirring apparatus and blending apparatus without the need for a specialized high pressure emulsification apparatus, which obviates the need for investigating optimal emulsification/dispersion conditions. Furthermore, a cosmetic composition produced using the gel composition according to the present invention is a hydrous cosmetic composition, and especially a water-in-oil emulsion cosmetic composition, that is excellent in terms of stability over time, feeling to touch, moisture retention, product appearance, and the like, and is a hydrous cosmetic composition in which the components mentioned above can be compounded easily and stably.

An explanation of the compounding components in the gel composition according to the present invention will now be given.

Component (E) is at least one type of compound selected from among the group consisting of lower monohydric alcohols and organic polyhydric alcohol-based compounds, and a gel composition comprising this component has the advantages of exhibiting further improved self-emulsification properties and obviating the need for detailed investigations into emulsification conditions, which are essential when producing a stable water-in-oil emulsion cosmetic composition.

Examples of lower alcohols include ethanol, isopropanol, n-propanol, t-butanol, s-butanol, and the like. Examples of polyhydric alcohols include divalent alcohols such as 1,3-butylene glycol, 1,2-butylene glycol, propylene glycol, trimethylene glycol, tetramethylene glycol, 2,3-butylene glycol, pentamethylene glycol, 2-buten-1,4-diol, dibutylene glycol, pentyl glycol, hexylene glycol, octylene glycol, and the like; trivalent alcohols such as glycerol, trimethylol propane, 1,2,6-hexanetriol, and the like; polyhydric alcohols having 4 or more valences such as pentaerythritol, xylitol, and the like; and sugar alcohols such as sorbitol, mannitol, maltitol, maltotriose, sucrose, erythritol, glucose, fructose, a starch-decomposed product, maltose, xylitose, starch-decomposed sugar-reduced alcohol, and the like. Furthermore, examples other than low-molecule polyhydric alcohols include polyhydric alcohol polymers such as diethylene glycol, dipropylene glycol, triethylene glycol, polypropylene glycol, tetraethylene glycol, diglycerol, polyethylene glycol, triglycerol, tetraglycerol, polyglycerol, and the like. Moreover, a polyhydric alcohol can be compounded in an amount of approximately 5 to 30 wt. % in order to improve the storage stability of the cosmetic composition. This is an example of a preferable mode of the present invention.

Component (E) is preferably ethanol, isopropanol, 1,3-butylene glycol, sorbitol, dipropylene glycol, glycerin, or polyethylene glycol, and can improve the stability of an emulsion. Of these, 1,3-butylene glycol, sorbitol, dipropylene glycol, glycerin, and polyethylene glycol exhibit a moisturizing effect, and are therefore preferable. In addition, using a mixture of ethanol and a component (E) other than ethanol at a weight ratio of 5/5 to 9.9/0.1 is preferable in terms of the self-emulsification properties of the gel composition. Furthermore, using ethanol and a physiologically acceptable hydrophilic medium other than ethanol at a weight ratio of 6/4 or higher is particularly preferable in terms of the self-emulsification properties of the gel composition.

Water is free of components that are harmful to the human body and needs only to be clean. Examples thereof include tap water, purified water, mineral water, deep sea water, and the like. A gel composition comprising a high concentration of a lower alcohol such as ethanol, which is component (E), is highly flammable, but incorporating water reduces the flash point and ensures greater safety during production, storage, and transport. In addition, it is possible to disperse a water-soluble component such as a water-soluble ionic surfactant in advance and then compound in the gel composition.

Moreover, in cases where the cosmetic composition according to the present invention is a cosmetic composition, and especially a water-in-oil emulsion cosmetic composition, produced by additionally compounding water in the gel composition, the cosmetic composition contains both water contained in the gel composition that is a composition for producing a cosmetic composition and water added when the cosmetic composition is produced. It goes without saying that these two batches of water cannot be distinguished in the cosmetic composition.

The gel composition according to the present invention is preferably a gel composition comprising from 10 to 70 wt. % of (A) the thickening agent or gelling agent for an oil-based raw material according to the present invention, from 30 to 80 wt. % of (D) an oil-based raw material, from 0 to 20 wt. % of (E) at least one type of compound selected from among the group consisting of lower monohydric alcohols and organic polyhydric alcohol-based compounds, and from 0 to 20 wt. % of water.

The gel composition according to the present invention is more preferably a gel composition comprising from 20 to 50 wt. % of (A) the thickening agent or gelling agent for an oil-based raw material according to the present invention, from 40 to 60 wt. % of (D) an oil-based raw material, from 5 to 15 wt. % of (E) at least one type of compound selected from among the group consisting of lower monohydric alcohols and organic polyhydric alcohol-based compounds, and from 5 to 15 wt. % of water.

An explanation of optional components in the gel composition according to the present invention will now be given. The ultraviolet light blocking component (F) can be an inorganic ultraviolet light blocking component or an organic ultraviolet light blocking component. The inorganic ultraviolet light blocking component is an ultraviolet light scattering agent that contains the inorganic powder pigment, metal powder pigment, and the like disclosed as component (B), and examples of organic ultraviolet light blocking components (F2) include salicylic acid-based compounds such as homomethyl salicylate, octyl salicylate, and triethanolamine salicylate; PABA-based compounds such as paraminobenzoic acid, ethyl dihydroxypropyl paraminobenzoic acid, glyceryl paraminobenzoic acid, octyl dimethyl paraminobenzoic acid, amyl paradimethylaminobenzoate, and 2-ethylhexyl paradimethylaminobenzoate; benzophenone-based compounds such as 4-(2-β-glucopyranosyloxy)propoxy-2-hydroxybenzophenone, dihydroxydimethoxybenzophenone, sodium dihydroxydimethoxybenzophenone disulfonate, 2-hydroxy-4-methoxybenzophenone, hydroxymethoxybenzophenone sulfonic acid or a trihydrate thereof, sodium hydroxymethoxybenzophenone sulfonate, 2-hydroxy-4-methoxybenzophenone-5-sulfuric acid, 2,2'-dihydroxy-4-methoxybenzophenone, 2,4-dihydroxybenzophenone, 2,2'4,4'-tetrahydroxybenzophenone, 2,2'-dihydroxy-4,4'-dimethoxybenzophenone, and 2-hydroxy-4-n-octoxybenzophenone; benzotriazole-based compounds such as 2-[4-(2-ethylhexyloxy)-2-hydroxyphenyl]-2H-benzotriazole and 2-(2-hydroxy-4-isobutoxyphenyl)-2H-benzotriazole; cinnamic acid-based compounds such as 2-ethylhexyl para-methoxycinnamate (also known as octyl para-methoxycinnamate), glyceryl mono-2-ethylhexanoyl di-para-methoxy cinnamate, methyl 2,5-di-isopropylcinnamate, 2,4,6-tris[4-(2-ethylhexyloxycarbonyl)anilino]-1,3,5-triazine, methyl-bis(trimethylsiloxy)silylisopentyl trimethoxycinnamate, a mixture of isopropyl para-methoxycinnamate and diisopropylcinnamic acid ester, and a diethanolamine salt of para-methoxyhydrocinnamic acid; benzoylmethane-based compounds such as 2-phenylbenzimidazole-5-sulfate, 4-isopropyldibenzoylmethane, and 4-tert-butyl-4'-methoxydibenzoylmethane; 2-ethylhexyl 2-cyano-3,3-diphenyl-2-propenoate (also known as octocrylene), 2-ethylhexyl dimethoxybenzylidene-dioxoimidazolidine propionate, 1-(3,4-dimethoxyphenyl)-4,4-dimethyl-1,3-pentanedione, cinoxate, methyl-O-aminobenzoate, 2-ethylhexyl-2-cyano-3,3-diphenylacrylate, 3-(4-methylbenzylidene)camphor, octyltriazone, 2-ethylhexyl 4-(3,4-dimethoxyphenylmethylene)-2,5-dioxo-1-imidazolidine propionate, and polymer derivatives and silane derivatives thereof. Because organic-based UV absorbers generally have high polarities and do not readily dissolve, it has been difficult in the past to stably compound a desired high amount of an organic-based UV absorber in a water-in-oil (W/O) emulsion cosmetic composition. However, when the co-modified organopolysiloxane of the present invention, which has a group that has a carbosiloxane dendron structure, along chain alkyl group, and a hydrophilic group, is used as a thickening/gelling agent having emulsification properties and when a medium polarity oil such as an ester oil or the like is combined therewith as a binding agent, a stable, UV absorber-containing W/O emulsion cosmetic composition can be obtained even when the oil phase contains a low polarity oil such as a silicone oil, a hydrocarbon oil, or the like. In this case, the compounded amount of the organic-based UV absorber is preferably in a range of 0.1 to 10 wt. % and the compounded amount of the binding agent is preferably in a range of 0.005 to 5 wt. %.

It is possible to use a material obtained by incorporating these organic ultraviolet light blocking components in a polymer powder. The polymer powder may or may not be hollow, should have an average primary particle size in a range of 0.1 to 50 μm, and may have a particle size distribution that is either broad or sharp. Types of polymer include acrylic resins, methacrylic resins, styrene resins, polyurethane resins, polyethylene, polypropylene, polyethylene terephthalate, silicone resins, nylons, and acrylamide resins. A polymer powder comprising from 0.1 to 30 wt. % of an organic ultraviolet light blocking component is preferable, and a polymer powder comprising 4-tert-butyl-4'-methoxydibenzoylmethane, which is a UV-A absorber, is particularly preferable. In particular, using both inorganic and organic ultraviolet light blocking components is preferable, and using a UV-A blocking component in combination with a UV-B blocking component is more preferable.

(G) The sucrose fatty acid ester or polyglycerol fatty acid ester is a component that functions as a nonionic surfactant, and preferably has 12 or more carbons, and more preferably has 12 to 20 carbons, in the fatty acid. These are useful for further improving the stability of a high internal aqueous phase W/O gel emulsion cosmetic composition. Examples of (G1) sucrose fatty acid esters include sucrose dioleate, sucrose distearate, sucrose dipalmitate, sucrose dimyristate, sucrose dilaurate, sucrose monooleate, sucrose monostearate, sucrose monopalmitate, sucrose monomyristate, sucrose monolaurate, and the like. Examples of (G2) polyglycerol fatty acid esters are esters of polyglycerins having an average degree of polymerization of 2 to 10 and fatty acids (for example, a fatty acid selected from among caprylic acid, capric acid, lauric acid, myristic acid, palmitic acid, stearic acid, oleic acid, and linoleic acid). Preferable examples of polyglycerol fatty acid esters include hexaglycerin monooleate, hexaglycerin monostearate, hexaglycerin monopalmitate, hexaglycerin monomyristate, hexaglycerin monolaurate, decaglycerin monooleate, decaglycerin monostearate, decaglycerin monopalmitate, decaglycerin monomyristate, decaglycerin monolaurate, and the like. These fatty acid esters can be used singly or as a mixture thereof.

The organic film-forming agent (H) is a component that forms a polymer film on skin or hair, examples of which include poly(vinyl alcohol), poly(vinyl pyrrolidone), alkyl polyacrylate copolymers, and silicone raw rubbers (also known as silicone gums).

Examples of silicone raw rubbers include substituted or unsubstituted organopolysiloxanes having a dialkylsiloxy unit (D unit), such as dimethylpolysiloxane, methylphenylpolysiloxane, methylfluoroalkylpolysiloxane, and the like, as well as products thereof that have a micro crosslinked structure and the like. Of these, a dimethylpolysiloxane raw rubber having a degree of polymerization of 3,000 to 20,000 is preferable.

Silicone gum has an ultra-high degree of polymerization and, therefore forms a protective film with superior breathability and retention on hair or skin. Therefore, the silicone gum is a component which can particularly provide glossiness and luster to hair and can impart a texture of firmness and body to the entire hair during use and after use.

A compounded amount of the silicone gum is in a range from 0.05 to 30 wt. % and preferably in a range from 1 to 15 wt. % of the entire cosmetic composition. When an emulsion composition prepared via a step of pre-emulsifying (including emulsion polymerization) is used, the silicone gum can easily be compounded, and can be stably compounded in the various cosmetic compositions of the present invention. Particularly, when the cosmetic composition of the present invention is a hair cosmetic composition or the like, an effect of imparting a specific feeling to touch or glossiness of the hair may be insufficient if the compounded amount of the silicone gum is less than the lower limit described above.

The at least one compound selected from among amino acids and/or salts thereof, inorganic salts, organic acids and/or salts thereof, and water-soluble polymers (J) is an optional component in a topical composition or cosmetic composition and can be compounded as appropriate according to the function of the cosmetic composition.

Examples of amino acids include amino acids such as glycine, valine, leucine, isoleucine, serine, threonine, phenylalanine, arginine, lysine, aspartic acid, glutamic acid, cysteine, cysteine, methionine, tryptophan, and the like, and/or salts thereof.

Examples of inorganic salts include hydrochloric acid, sulfuric acid, nitric acid, carbonic acid, phosphoric acid, and similar alkali metal salts, alkaline earth metal salts, aluminum salts, zinc salts, ammonium salts, or the like. Preferable inorganic salts include sodium chloride, potassium chloride, magnesium chloride, calcium chloride, aluminum chloride, zinc chloride, ammonium chloride, and similar chlorides; sodium sulfate, potassium sulfate, magnesium sulfate, aluminum sulfate, zinc sulfate, ammonium sulfate, and other sulfides; sodium nitrate, potassium nitrate, magnesium nitrate, calcium nitrate, aluminum nitrate, zinc nitrate, ammonium nitrate, and similar nitrates; sodium carbonate, potassium carbonate, magnesium carbonate, calcium carbonate, and similar carbonates; and sodium phosphate, potassium phosphate, and similar phosphates. Of these, sodium chloride, potassium chloride, magnesium chloride, calcium chloride, sodium sulfate, potassium sulfate, magnesium sulfate, and aluminum sulfate are particularly preferable.

Organic acids are acids such as acetic acid, lactic acid, citric acid, ascorbic acid, malic acid, and tartaric acid. Examples of organic salts include sodium acetate, potassium acetate, and sodium ascorbate, as well as sodium citrate, sodium lactate, sodium glycolate, sodium malate, sodium tartrate, and similar α-hydroxyacid salts; sodium aspartate, potassium aspartate, magnesium aspartate, calcium aspartate, sodium glutamate, potassium glutamate, magnesium glutamate, calcium glutamate, arginine-glutamate salts, ornithine-glutamate salts, lysine-glutamate salts, lysine-aspartate salts, ornithine-aspartate salts, and similar amino acid salts; sodium alginate; and the like.

The water-soluble polymer can be compounded in order to prepare a cosmetic in the desired form or to stabilize or adjust the refractive index of the aqueous phase. Other compounding purposes include improving the sensation during use of the cosmetic composition, such as feeling to touch on the skin, hair, or the like, improving the moisturizing effect, improving the conditioning effect, and the like. Any of amphoteric, cationic, anionic, and nonionic polymers, and water-swellable clay minerals can be used provided that the water-soluble polymer is one that is commonly used in cosmetic products, and it is possible to use one or two or more of these water-soluble polymers. The water-soluble polymers described above have an effect of thickening a hydrous component and, for this reason, are particularly useful in obtaining a gel hydrous cosmetic composition, a water-in-oil emulsion cosmetic composition, and an oil-in-water emulsion cosmetic composition.

Examples of amphoteric water-soluble polymers include amphoteric starches, dimethyldiallylammonium chloride derivatives (for example, acrylamide-acrylic acid-dimethyldiallylammonium chloride copolymers and acrylic acid-dimethyldiallylammonium chloride copolymers), and methacrylic acid derivatives (for example, polymethacryloylethyldimethylbetaines, N-methacryloyloxyethyl-N,N-dimethylammonium-α-methylcarboxybetaine-alkyl methacrylate copolymers, and the like).

Examples of cationic water-soluble polymers include quaternary nitrogen-modified polysaccharides (for example, cation-modified cellulose, cation-modified hydroxyethylcellulose, cation-modified guar gum, cation-modified locust bean gum, cation-modified starch, and the like); dimethyldiallylammonium chloride derivatives (for example, copolymers of dimethyldiallylammonium chloride and acrylamide, poly(dimethylmethylene piperidinium chloride), and the like); vinylpyrrolidone derivatives (for example, copolymers of vinylpyrrolidone and dimethylaminoethyl methacrylic acid, copolymers of vinylpyrrolidone and methacrylamide propyltrimethylammonium chloride, copolymers of vinylpyrrolidone and methylvinylimidazolium chloride, and the like); and methacrylic acid derivatives (for example, methacryloylethyldimethylbetaine-methacryloylethyltrimethyl ammonium chloride-2-hydroxyethyl methacrylate copolymers, methacryloylethyldimethylbetaine-methacryloylethyltrimethyl ammonium chloride-methoxy polyethylene glycol methacrylate copolymers, and the like).

Examples of anionic water-soluble polymers include poly (acrylic acid) and alkali metal salts thereof, poly(methacrylic acid) and alkali metal salts thereof, hyaluronic acid and alkali metal salts thereof, acetylated hyaluronic acid and alkali metal salts thereof, water-soluble polymers of aliphatic carboxylic acids or metal salts thereof, such as hydrolysates of methyl vinyl ether-maleic anhydride copolymers, carboxymethyl cellulose and alkali metal salts thereof, methyl vinyl ether-maleic acid half ester copolymers, alkanolamide solutions of acrylic resins, and carboxyvinyl polymers.

Examples of nonionic water-soluble polymers include poly(vinyl pyrrolidone), highly polymerized polyethylene glycols, PEG/PPG-36/41 dimethyl ethers, PEG/PPG-14/7 dimethyl ethers, vinyl pyrrolidone-vinyl acetate copolymers, vinyl pyrrolidone-dimethylaminoethyl methacrylate copolymers, vinyl caprolactam-vinyl pyrrolidone-dimethylaminoethyl methacrylate copolymers, cellulose and derivatives thereof (for example, methyl cellulose, ethyl cellulose, hydroxyethyl cellulose, hydroxypropyl cellulose, and carboxymethyl cellulose), keratin and collagen and derivatives thereof, calcium alginate, pullulan, agar, gelatin, tamarind seed polysaccharides, xanthan gum, carrageenan, highmethoxylpectin, low-methoxylpectin, guar gum, pectin, gum arabic, crystalline cellulose, arabinogalactan, karaya gum, gum tragacanth, alginic acid, albumin, casein, curdlan, gellan gum, dextran, *pyrus cydonia* seed gum, gum tragacanth, chitin/chitosan derivatives, starches (rice, corn, potato, wheat and the like), keratin and collagen and derivatives thereof, and similar natural polymer compounds.

Water-swellable clay minerals are inorganic water-soluble polymers, a common example of which is the material expressed by formula (1) below, which is a type of colloid-containing aluminum silicate having a three-layer structure.

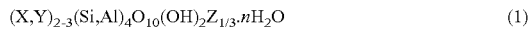

$$(X,Y)_{2\text{-}3}(Si,Al)_4O_{10}(OH)_2Z_{1/3} \cdot nH_2O \tag{1}$$

(In this formula, X is Al, Fe(III), Mn(III), or Cr(III), Y is Mg, Fe(II), Ni, Zn, or Li, and Z is K, Na, or Ca)

Specific examples of such inorganic water-soluble polymers include bentonite, montmorillonite, beidellite, nontronite, saponite, hectorite, magnesium aluminum silicate, and silicic anhydride, and these may be natural or synthetic products.

Gel compositions comprising the components mentioned above can be blended with water by means of mechanical forces using an apparatus such as a homomixer, a paddle mixer, a Henschel mixer, a homo-disper, a colloid mill, a propeller stirrer, a homogenizer, an in-line continuous emulsifier, an ultrasonic emulsifier, or a vacuum kneader.

In the cosmetic composition production method of the present invention, the usage amount/compounding ratio of water is not limited, but can be from 0.1 to 4,000 parts by weight, and preferably from 5 to 2,000 parts by weight, of water relative to 100 parts by weight of a gel composition comprising the components mentioned above. The obtained gel composition can be in a form such as an oil-in-water emulsion or a water-in-oil emulsion, but is extremely useful due to being able to be formed as a stable water-in-oil emulsion.

The emulsion composition including the co-modified organopolysiloxane according to the present invention can be suitably used as a preparation for external use, particularly for a cosmetic composition or a cosmetic raw material. Other cosmetic raw material components can be compounded in the aqueous phase or the oil phase of the emulsion composition, and this type of emulsion composition that comprises these cosmetic raw material components is encompassed by the present invention.

Furthermore, the transparency of an emulsion composition comprising the co-modified organopolysiloxane of the present invention can be adjusted by independently mixing the components that constitute the aqueous phase and the components that constitute the oil phase and then emulsifying so that the difference in refractive index at room temperature between the two phases is less than or equal to 0.0020 units. Specifically, the present invention includes a method of adjusting the transparency of an emulsion composition, comprising independently mixing an aqueous phase and an oil phase that contains the component (A) and oil-based raw material (D), and then emulsifying after adjusting so that the difference in refractive index between the two phases at 25° C. is less than or equal to 0.0020 units.

More specifically, the method of adjusting the transparency of the emulsion composition of the present invention includes the following steps (i) to (iv).

(i) The constituent components of the oil phase, which contains the co-modified organopolysiloxane according to the present application and (D) an oil-based raw material, may be blended using any method that is already known for such techniques. In such cases, the entire oil phase may be gelled or thickened. Specifically, as long as aqueous phase components are not contained therein, the oil phase may be a gel composition. Similarly, the components that constitute the aqueous phase are blended in a separate container.

(ii) The refractive index (RI) of each phase is measured separately at room temperature (25° C.).

(iii) The refractive index of each of the phases is adjusted so that the difference between the refractive indices of these two phases is at least within 0.0020 units, and the optical transparency of the final mixture is obtained.

(iv) The two phases are emulsified. Emulsifying can be performed according to a desired emulsifying method but, ordinarily, the two phases are coalesced as an emulsion by gradually introducing the aqueous phase into the oil phase while agitating using mechanical means such as a shear mixer or the like.

The method of adjusting the transparency of the emulsion of the present invention can particularly be suitably used when adjusting a water-in-oil emulsion composition. The obtained emulsion composition can be processed under high shear conditions using an appropriate apparatus such as a homogenizer or the like and, as a result, the transparency and stability thereof can be further enhanced. Additionally, in step (iii), when adjusting a semi-transparent to highly transparent emulsion, the difference in the refractive indices of the two phases is within at least about 0.0020 refractive index (RI) units, preferably within about 0.00010 units, and most preferably, there is no difference between the refractive indices of the two phases.

On the other hand, when preparing a milky emulsion or the like, in applications where transparency of the emulsion is not particularly needed, emulsification can be carried out without adjusting the refractive index of each phase, and an opaque emulsion composition can be obtained.

The adjusting of the refractive indices can be performed by simply diluting the aqueous phase using an additional amount of water. Furthermore, a refractive index (RI) adjuster can be compounded in the aqueous phase or oil phase of the emulsion composition including the co-modified organopolysiloxane according to the present invention in order to adjust the difference between the refractive indices of the oil phase and the aqueous phase. Thereby, optical transparency of the emulsion composition can be obtained. In other words, when the difference between the refractive indices of both phases is 0 or extremely small, the entire emulsion composition is transparent or semi-transparent.

A type and amount used of the refractive index adjuster varies according to the refractive indices of the aqueous phase and the oil phase and, generally, is present in an amount sufficient to adjust the refractive indices of the aqueous phase and the oil phase so as to obtain optical transparency.

The refractive index adjuster is not particularly limited provided that this component is a compound having the effect of increasing the refractive index value of the aqueous phase of the composition or is a component that lowers the refractive index value of the oil phase of the composition. Additionally, adding the refractive index adjuster may be performed at any stage of the steps (i) to (iv), but from a practical perspective, the refractive index of each phase is preferably adjusted in step (iii), using the refractive index adjuster.

Examples of the compound used as the refractive index adjuster of the aqueous phase include polyhydric alcohols and derivatives thereof, sugar alcohols and derivatives thereof, polyoxyalkylene group-containing alcohols, polyoxyalkylene group-containing ethers, silicone-polyether copolymers, various water soluble polar compounds, water soluble inorganic salts, organic salts, amino acids, and the like. One of these aqueous phase refractive index adjusters may be used or a combination of two or more may be used. A component that is a part of the cosmetic raw material components can be suitably used as the aqueous phase refractive index adjuster.

Specific examples of the aqueous phase refractive index adjuster that can be used include propylene glycol, dipropylene glycol, glycerin, sorbitol, mannitol, xylitol, pentaerythritol, trimethylolpropane, hexylene glycol, octylene glycol, 1,2-butanediol, 1,2-pentanediol, 4-methyl-1,2-pentanediol, 2-methyl-1,2-pentanediol, 3,3-methyl-1,2-butanediol, 4-methyl-1,2-hexanediol, 1,2-heptanediol, 3-phenyl-1, 2-propanediol, glycerol isopropyl ether, glycerol propyl ether, glycerol ethyl ether, glycerol methyl ether, glycerol butyl ether, glycerol isopentyl ether, diglycerol isopropyl ether, diglycerol isobutyl ether, triglycerol isopropyl ether, alkyl xylitol ether, alkyl sorbitol ether, 1,2,6-hexanetriol, 1,2-hexanediol, 1,2,4-butanetriol, 1,2-butylene glycol, 1,3-butylene glycol, diglycerin, triglycerin, tetraglycerin, polyglycerin, polyethyleneglycol, glycerin monoalkyl ether (e.g. hexyl alcohol, selachyl alcohol, batyl alcohol, and the like); sugar alcohols (e.g. maltitol, maltotriose, sucrose, erythritol, glucose, fructose, starch-decomposed products, maltose, xylitose, starch-decomposed sugar-reduced alcohols, and the like); glysolid; tetrahydrofurfuryl alcohol; POE-tetrahydrofurfuryl alcohol; POP-butyl ether; POE-butyl ether; POP•POE-butyl ether; tripolyoxypropylene glycerin ether; POP-glycerin ether; POP-glycerin ether phosphate; POP•POE-pentane erythritol ether, silicone-polyether copolymers or various water soluble-polar substances; water soluble inorganic salts such as sodium chloride, or organic salts, amino acids, and the like.

Examples of components that can be used as the oil phase refractive index adjuster include the products cited as examples of the oil agent of the present invention; oils and fats commonly used in cosmetic compositions, higher alcohols, higher fatty acids, organic-based oleophilic surfactants, and the like. However, because this component is used to adjust the oil phase refractive index, it is an oil agent that is different than the oil agent used as the base oil of the oil phase of the emulsion. One of these oil phase refractive index adjusters may be used or a combination of two or more may be used. Additionally, a mixture of two base oils may be used for the purpose of adjusting the refractive index of the oil phase.

Specific examples of the oil phase refractive index adjuster include silicone oils, lauryl myristate or diisopropyl sebacate, diisopropyl adipate, ester oils such as benzoic acid alkyls having 8 to 18 carbons, mineral oils or polydecenes, hydrogenated polyisobutene, and similar hydrocarbon oils, oleyl alcohol, batyl alcohol, lanolin alcohol, cholesterol, phytosterol, octyldodecanol, and similar long chain alcohols, PPG-3 myristyl ether or PPG-14 butyl ether, and POE(20) glyceryl triisostearate, or other mixtures.

Similarly, by diluting the gel composition of the present invention by blending water and (K) a bioactive substance therein, it is possible to provide a method for easily obtaining a topical composition or a cosmetic composition, and especially an emulsion cosmetic composition, in an arbitrary form having a lower viscosity than paste-form, cream-form, and milk-form forms, and the like. Specifically, it is possible to obtain a topical composition by blending 100 parts by weight of a gel composition comprising the components mentioned above, 0.1 to 4,000 parts by weight of water, and 0.001 to 1.0 parts by weight of (K) a bioactive substance. Moreover, being able to obtain an emulsion cosmetic composition having excellent transparency by adjusting the refractive indices of the oil phase component and aqueous phase component is as mentioned above.

Examples of bioactive substances (K) include substances that impart some sort of bioactivity to the skin when applied on the skin. Examples thereof include anti-perspiration active components, deodorant agents, anti-inflammatory agents, anti-aging agents, skin-lightening agents, tightening agents, anti-oxidizing agents, hair regrowth agents, hair growth promoters, circulation promoters, antimicrobial agents, germicides, drying agents, cooling agents, warming agents, vitamins, amino acids, wound healing accelerators, irritation mitigation agents, analgesics, cell activating agents, enzyme components, and the like. The bioactive substance is preferably at least one type of bioactive substance selected from among an anti-inflammatory agent, an anti-aging agent, a skin-lightening agent, a hair regrowth agent, a hair growth promoter, a circulation promoter, an antimicrobial agent, a germicide, a vitamin, a wound healing accelerator, an irritation mitigation agent, an analgesic, a cell activating agent, and an enzyme.

In particular, in cases where the cosmetic composition according to the present invention is an anti-perspirant, or depending on the purpose of the cosmetic composition, the cosmetic composition can contain an anti-perspiration active component and/or a deodorant agent.

Examples of the anti-perspiration active component include astringent salts such as aluminum chlorohydrate, aluminum-zirconium tetrachlorohydrex glycine (ZAG), and the like; but aluminum, hafnium, zinc, and zirconium salts (e.g. aluminum halide, aluminum hydroxy halide, zirconium halide, zirconium oxyhalide, zirconium hydroxy halide, zirconyl hydroxide halide, aluminum chloride zirconium, zirconium lactate-aluminum, and basic aluminum halide) can be used. Examples thereof include $Al_2(OH)_5Cl$, aluminum bromide, buffer aluminum sulphate, alum, dried alum, various aqueous, alcohol, or glycine complexes thereof (e.g. a complex of an aluminum-zirconium chlorohydrate and glycine comprising aluminum, zirconium, and glycine (a ZAG complex), and the like. A single anti-perspiration active component may be used or a combination of two or more may be used. In cases where the anti-perspirant composition according to the present invention is a water-in-oil emulsion-type anti-perspirant composition, these anti-perspiration active components are an aqueous phase component. On the other hand, soybean extracts and isoflavones are known for their anti-perspirant effects; and, because they have low water solubility, are preferably used by dissolving them in the oil phase.

In the present invention, a compounded amount of the anti-perspiration active component is an amount sufficient to reduce perspiration, and restricting the compounded amount to a small amount can be beneficial in personal care compositions. Specifically, from the standpoints of anti-perspirant effects and feeling to touch, the compounded amount of the anti-perspiration active component in an anti-perspirant composition is preferably from 5 to 25 wt. % of the entire cosmetic composition. When using a water soluble anti-perspiration active component, from the standpoint of cost effectiveness, it is preferable to increase the proportion of water in the composition to a maximum limit, while maintaining anti-perspirant effects, but the anti-perspiration active component can also be added to the aqueous phase at amount near the saturation amount.

The cosmetic composition of the present invention, particularly the anti-perspirant composition, can include a deodorant agent in conjunction with or in place of the anti-perspirant component. Examples of the deodorant agent include deodorizers, perfumes, and substances that prevent or remove odors caused by perspiration. Such deodorant agents are antimicrobial agents (germicides or fungicides), bacteriostatic agents, odor absorbing substances, deodorizers, perfumes, or the like, and are compounded for the purpose of preventing underarm odor, odor from perspiration, foot odor, and other bodily odors. Note that these deodorant agents are useful in cosmetic compositions other than anti-perspirants and it goes without saying that they can be beneficially compounded in the cosmetic composition of the present invention.

Examples of antimicrobial agents include alkyltrimethylammonium bromide, cetylpyridinium chloride, benzethonium chloride, benzalkonium chloride, chlorhexidine hydrochloride, chlorhexidine gluconate, [[(diisobutylphenoxy)ethoxy]ethyl]dimethylbenzylammonium chloride, N-lauroyl sarcosine sodium, N-palmitoyl sarcosine sodium, N-myristoyl glycine, N-lauroyl sarcosine potassium, trimethyl ammonium chloride, aluminum chlorohydroxy sodium lactate, triethyl citrate, tricetyl methyl ammonium chloride, 1,5-pentanediol, 1,6-hexanediol, 2,4,4'-trichloro-2'-hydroxy diphenylether (triclosan), and 3,4,4'-trichlorocarbanilide(triclocarban); L-lysine hexadecylamide and similar diaminoalkylamidos; citric acid, salicylic acid, piroctose, and other heavy metal salts, preferably zinc salts and acids thereof; pyrithione heavy metal salts, preferably pyrithione zinc, phenol zinc sulfate, ethylparaben, butylparaben, hinokitiol, farnesol, phenoxyethanol, isopropyl methylphenol, propolis, lysozyme, lysozyme chloride, combinations of lysozyme and vitamin E or derivatives thereof, combinations of organic acids such as lysozyme and α-hydroxyacid and the like; and the like.

Examples of bacteriostatic agents include 1-heptyl glyceryl ether, 1-(2-ethylhexyl)glyceryl ether, 1-octyl glyceryl ether, 1-decyl glyceryl ether, 1-dodecyl glyceryl ether, and similar glyceryl monoalkyl ethers.

The odor absorbing substance is not particularly limited, provided that it absorbs odor causing substances and reduces odor, is constituted by a portion of the inorganic powders and organic polymers described above, and displays the same characteristics.

Examples of the odor absorbing substance include zinc oxide, magnesium oxide, zeolite, aluminometasilicate, silicic anhydride, colloidal silica, talc, mica, hydroxyapatite, cellulose, corn starch, silk, nylon powder, crosslinking organopolysiloxane powder, organopolysiloxane elastomer spherical powder, and the like. Likewise, carbonates such as alkali metal carbonates, alkali metal bicarbonate salts, and the like and hydrogen carbonates, ammonium salts, tetraalkylammonium salts, and the like can be used. Of these odor absorbing substances, sodium salts and potassium salts are more preferable. Additionally, organic or inorganic porous particles carrying silver, copper, zinc, cerium, or similar metal ions (e.g. silver ion-carrying zeolite, silver ion/zinc ion/ammonium ion-carrying zeolite), or aggregates of needle-form crystals including silver cancrinite can be used. Because these function as antimicrobial agents and odor absorbing substances, they can be used beneficially as the deodorant agent.

Furthermore, hydroxyalkylated cyclodextrin, sake cake extract containing rice fermenting liquid, and various extracts derived from animals, vegetables, microorganisms, fungi, and the like such as brown seaweed extract, cinnamon bark, clove, fennel, ginger, *mentha*, citron, *gentiana lutea*, apricot, eucalyptus, *Sophora flavescens*, mulberry, althea, sage, *Anthemis nobilis*, *Scutellaria* root, nutgall, *gardenia, hamamelis*, herbs, and the like can be used as the deodorant agent. A part of these components overlaps with a bioactive component described below, but selecting these extracts as the deodorant agent for the purpose of the functional effects thereof is both beneficial and preferable from the standpoint of the composition design of the cosmetic composition.

Preferably from 0.001 to 60 wt. %, more preferably from 0.01 to 30 wt. %, and yet more preferably from 0.01 to 3 wt. % of the odor absorbing substance is included in the entire composition. Provided that the compounded amount of the odor absorbing substance is within this range, there is an advantage that deodorizing performance can be improved while not negatively affecting the strength and feeling to touch of the formulation.

Suitable perfumes include known topical use substances, topical use substances that are effective in masking malodor accompanied by perspiration, and various topical use substances that provide a composition having a desired aroma. Examples thereof include the whole of perfumes and perfume chemicals such as perfume precursors, deodorizing fragrances, and the like that are suitable for topical application to the skin and, as necessary, may be a blended perfume component. More specifically, examples thereof include perfumes that contain a variety of extracts and are extracted from a variety of plant flowers, seeds, leaves, roots, and the like, perfumes extracted from seaweed, perfumes extracted from a variety of animal parts and secretions (for example, musk or sperm oil), and artificially synthesized perfumes (for example, menthol, musk, acetic acid esters, and vanilla).

The cosmetic composition of the present invention can include a preservative for the purpose of preventing decomposition and the like. Examples of preservatives include alkyl paraoxybenzoates, benzoic acid, sodium benzoate, sorbic acid, potassium sorbate, phenoxyethanol, and the like. Examples of antimicrobial agents include benzoic acid, salicylic acid, carbolic acid, sorbic acid, alkyl paraoxybenzoates, parachlorometacresol, hexachlorophene, benzalkonium chloride, chlorhexidine chloride, trichlorocarbanilide, triclosan, photosensitizers, and the like. However, in cases where the cosmetic composition is a rouge, it is preferable that these are not included.

Examples of other bioactive components include Angelica keiskei extract, avocado extract, Hydrangea serrata extract, Althaea officinalis extract, Arnica montana extract, aloe extract, apricot extract, apricot kernel extract, Gingko biloba extract, fennel fruit extract, turmeric root extract, oolong tea extract, Rosa multiflora extract, Echinacea angustifolia leaf extract, Scutellaria baicalensis root extract, Phellodendron amurense bark extract, Coptis rhizome extract, Hordeum vulgare seed extract, Hypericum perforatum extract, Lamium album extract, Nasturtium officinale extract, orange extract, dried sea water solution, seaweed extract, hydrolyzed elastin, hydrolyzed wheat powders, hydrolyzed silk, Chamomilla recutita extract, carrot extract, Artemisia capillaris flower extract, Glycyrrhiza glabra extract, Hibiscus sabdariffa extract, Pyracantha fortuneana extract, kiwi extract, Cinchona succirubra extract, cucumber extract, guanosine, Gardenia florida extract, Sasa veitchii extract, Sophora angusti folia extract, walnut extract, grapefruit extract, Clematis vitalba leaf extract, chlorella extract, Morus alba extract, Gentiana lutea extract, black tea extract, yeast extract, burdock extract, fermented rice bran extract, rice germ oil, Symphytum officinale leaf extract, collagen, Vaccinum vitis idaea extract, Asiasarum sieboldi extract, Bupleurum falcatum extract, umbilical extract, Salvia extract, Crocus sativus flower extract, sasa bamboo grass extract, Crataegus cuneata fruit extract, Zanthoxylum piperitum extract, Corthellus shiitake extract, Rehmannia chinensis root extract, Lithospermum erythrorhizone root extract, Perilla ocymoides extract, Tilia cordata extract, Spiraea ulmaria extract, Paeonia albiflora extract, Acorns calamus root extract, Betula alba extract, Equisetum arvense extract, Hedera helix extract, Crataegus oxyacantha extract, Sambucus nigra extract, Achillea millefolium extract, Mentha piperita leaf extract, sage extract, Malva sylvestris extract, Cnidium officinale root extract, Swertia japonica extract, soybean seed extract, Zizyphus jujuba fruit extract, thyme extract, Camellia sinensis leaf extract, Eugenia caryophyllus flower extract, Imperata cylindrica extract, Citrus unshiu peel extract, Angelica acutiloba root extract, Calendula officinalis extract, Prunus persica kernel extract, Citrus aurantium peel extract, Houttuynia cordata extract, tomato extract, natto extract, carrot extract, garlic extract, Rosa canina fruit extract, hibiscus extract, Ophiopogon japonicus root extract, Nelumbo nucifera extract, parsley extract, honey, Hamamelis virginiana extract, Parietaria officinalis extract, Isodon trichocarpus extract, bisabolol, Eriojotrya japonica extract, Tussilago farfara flower extract, Petasites japonicus extract, Poria cocos extract, Ruscus aculeatus root extract, grape extract, propolis, Luffa cylindrica fruit extract, safflower flower extract, peppermint extract, Tillia miquellana extract, Paeonia suffruticosa root extract, Humulus lupulus extract, Pinus sylvestris cone extract, horse chestnut extract, Lysichiton camtschatcense extract, Sapindus mukurossi peel extract, Melissa officinalis leaf extract, peach extract, Centaurea cyanus flower extract, Eucalyptus globulus leaf extract, Saxifraga sarementosa extract, Citrus junos extract, Coix lacryma-jobi seed extract, Artemisia princeps extract, lavender extract, apple extract, lettuce extract, lemon extract, Astragalus sinicus extract, rose extract, rosemary extract, Roman chamomile extract, and royal jelly extract.

In addition, examples of the bioactive component include biological macromolecules such as deoxyribonucleic acid, mucopolysaccharides, sodium hyaluronate, sodium chondroitin sulfate, collagen, elastin, chitin, chitosan, hydrolytic membrana testae, and the like; hormones such as estradiol, ethenyl estradiol, and the like; oil-based components such as sphingo lipid, ceramide, cholesterol derivatives, phosphatides, and the like; anti-inflammatory agents such as ε-aminocaproic acid, glycyrrhizinic acid, β-glycyrrhetic acid, lysozyme chloride, guai-azulene, hydrocortisone, allantoin, tranexamic acid, azulene, and the like; vitamins such as vitamin A, B2, B6, C, D, and E, calcium pantothenate, biotin, nicotinic acid amide, vitamin C esters, and the like; active components such as allantoin, diisopropyl amine dichloroacetate, 4-aminomethyl cyclohexanecarboxylic acid, and the like; anti-oxidizing agents such as carotenoid, flavonoid, tannin, lignan, saponin, and the like; cell activator agents such as α-hydroxyacid, β-hydroxyacid, and the like; circulation promoters such as γ-orizanol, vitamin E derivatives, and the like; wound healing agents such as retinol, retinol derivatives, and the like; refreshing agents such as cepharanthine, licorice extract, capsicum tincture, hinokitiol, iodized garlic extract, pyridoxine hydrochlorate, dl-α-tocopherol, dl-α-tocopherol acetate, nicotinic acid, nicotinic acid derivatives, calcium pantothenate, D-pantothenyl alcohol, acetyl pantothenyl ethyl ether, allantoin, isopropyl methylphenol, carpronium chloride, benzalkonium chloride, diphenhydramine hydrochlorate, Takanal, camphor, anillylamide nonylate, vanillylamide nonanoate, piroctone olamine, glyceryl pentadecanoate, l-menthol, camphor, and the like; hair growth promoters such as mononitroguaiacol, resorcin, γ-aminobutyric acid, benzethonium chloride, mexiletine hydrochloride, auxin, female hormones, Cantharides tincture, cyclosporin, zinc pyrithione, hydrocortisone, Minoxidil, polyoxyethylene sorbitan monostearate, mentha oil, Sasanishiki extract, and the like.

Moreover, examples of skin beautifying components include skin-lightening agents such as placenta extracts, arbutin, glutathione, saxifrageous extracts, and the like; cell activating agents such as royal jelly and the like; agents for ameliorating skin roughness; circulation promoters such as nonylic acid vanillylamide, benzyl nicotinate, beta-butoxyethyl nicotinate, capsaicin, zingerone, cantharide tincture, ichthammol, caffeine, tannic acid, a-borneol, tocopherol nicotinate, inositol hexanicotinate, cyclandelate, cinnarizine, tolazoline, acetylcholine, verapamil, cepharanthine, γ-oryzanol, and the like; astringents such as zinc oxide, tannic acid, and the like; antiseborrheic agents such as sulfur, thianthol, and the like; and the like. Examples of vitamins include vitamin As such as vitamin A oil, retinol, retinol acetate, retinol palmitate, and the like; vitamin Bs such as vitamin B2s such as riboflavin, riboflavin butyrate, flavin adenine dinucleotide, and the like; vitamin B6s such as pyridoxine hydrochloride, pyridoxine dioctanoate, pyridoxine tripalmitate, and the like; vitamin B12 and derivatives thereof; vitamin B15 and derivatives thereof, and the like; vitamin Cs such as L-ascorbic acid, L-ascorbyl dipalmitic acid esters, sodium L-ascorbyl 2-sulfate, dipotassium L-ascorbyl phosphoric acid diester, and the like; vitamin Ds such as ergocalciferol, cholecalciferol, and the like; vitamin Es such as α-tocopherol, β-tocopherol, γ-tocopherol, dl-α-tocopherol acetate, dl-α-tocopherol nicotinate, dl-α-tocopherol succinate, and the like; vitamin H; vitamin P; nicotinic acids such as nicotinic acid, benzyl nicotinate, and the like; pantothenic acids such as calcium pantothenate, D-pantothenyl alcohol, pantothenyl ethyl ether, acetyl pantothenyl ethyl ether, and the like; and the like.

The topical composition, cosmetic composition, and the like according to the present invention can, if necessary, further contain another surfactant. In particular, one or two or more surfactants selected from the group consisting of an anionic surfactant, a cationic surfactant, a nonionic surfactant, an amphoteric surfactant, and a semipolar surfactant can be used in combination for the purpose of dispersing the oil agent in water with higher stability. Moreover, from the perspective of being able to improve the overall stability of the formulation, a silicone-based nonionic surfactant is preferably used. A compounded amount of these surfactants is in a range from 0.1 to 25 wt. % and preferably in a range from 0.5 to 10 wt. % of the entire cosmetic composition.

Furthermore, in cases where the topical composition, gel composition or cosmetic composition of the present invention is used in a cleansing agent, two or more types of surfactants can be preferably compounded from the perspective of cleansing activity. In cases where the cosmetic composition according to the present invention is a cosmetic composition for cleansing skin or cleansing hair, the compounded amount can be adjusted within a range from 0.1 to 90 wt. % of the entire cosmetic composition for the purpose of improving cleansing properties, and from the perspective of cleansing ability, the surfactant component is preferably compounded at an amount of not less than 25 wt. % of the entire cosmetic composition.

More specifically, examples of anionic surfactants include saturated or unsaturated fatty acid salts (e.g. sodium laurate, sodium stearate, sodium oleate, sodium linolenate, and the like); alkylsulfuric acid salts; alkylbenzene sulfonic acids (e.g. hexylbenzenesulfonic acid, octylbenzenesulfonic acid, dodecylbenzenesulfonic acid, and the like) and salts thereof; polyoxyalkylene alkyl ether sulfuric acid salts; polyoxyalkylene alkenyl ether sulfuric acid salts; polyoxyethylene alkylsulfuric ester salts; sulfosuccinic acid alkyl ester salts; polyoxyalkylene sulfosuccinic acid alkyl ester salts; polyoxyalkylene alkylphenyl ether sulfuric acid salts; alkanesulfonic acid salts; octyltrimethylammonium hydroxide; dodecyltrimethylammonium hydroxide; alkyl sulfonates; polyoxyethylene alkylphenyl ether sulfuric acid salts; polyoxyalkylene alkyl ether acetic acid salts; alkyl phosphoric acid salts; polyoxyalkylene alkyl ether phosphoric acid salts; acylglutamic acid salts; α-acylsulfonic acid salts; alkylsulfonic acid salts; alkylallylsulfonic acid salts; α-olefinsulfonic acid salts; alkylnaphthalene sulfonic acid salts; alkanesulfonic acid salts; alkyl- or alkenylsulfuric acid salts; alkylamide sulfuric acid salts; alkyl- or alkenyl phosphoric acid salts; alkylamide phosphoric acid salts; alkyloylalkyl taurine salts; N-acylamino acid salts; sulfosuccinic acid salts; alkyl ether carboxylic acid salts; amide ether carboxylic acid salts; a-sulfofatty acid ester salts; alanine derivatives; glycine derivatives; and arginine derivatives.

Examples of salts include alkali metal salts such as sodium salts and the like, alkaline earth metal salts such as magnesium salts and the like, alkanolamine salts such as triethanolamine salts and the like, and ammonium salts.

Examples of cationic surfactants include alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, di stearyldimethylammonium chloride, dicocoyldimethylammonium chloride, dioctyldimethylammonium chloride, di(POE)oleylmethylammonium (2 EO) chloride, benzalkonium chloride, alkyl benzalkonium chloride, alkyl dimethylbenzalkonium chloride, benzethonium chloride, stearyl dimethylbenzylammonium chloride, lanolin derivative quaternary ammonium salt, diethylaminoethylamide stearate, dimethylaminopropylamide stearate, behenic acid amide propyldimethyl hydroxypropylammonium chloride, stearoyl colaminoformyl methylpyridinium chloride, cetylpyridinium chloride, tall oil alkylbenzyl hydroxyethylimidazolinium chloride, and benzylammonium salt.

Examples of nonionic surfactants include polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hydrogenated) castor oils, polyoxyalkylene alkyl phenols, polyoxyalkylene alkyl phenyl ethers, polyoxyalkylene phenyl phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycol, diethyleneglycol, polyoxyalkylene-modified silicones, polyglyceryl-modified silicones, glyceryl-modified silicones, sugar-modified silicones, fluorine-based surfactants, polyoxyethylene/polyoxypropylene block polymers, and alkyl polyoxyethylene/polyoxypropylene block polymer ethers. In particular, the nonionic surfactant is a silicone-based surfactant, and a polyoxyalkylene-modified silicone, a polyglycerol-modified silicone, or a glycerol-modified silicone in which an alkyl branch, a straight chain silicone branch, and the like may, if necessary, be contained together with a hydrophilic group can also be preferably used.

Examples of amphoteric surfactants include imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. Specific examples thereof include imidazoline-type amphoteric surfactants such as sodium 2-undecyl-N,N,N-(hydroxyethylcarboxymethyl)-2-imidazoline, 2-cocoyl-2-imidazolinium hydroxide-1-carboxyethyloxy disodium salt, and the like; alkylbetaine-type amphoteric surfactants such as lauryl dimethylaminoacetic acid betaine, myristyl betaine, and the like; and amidobetaine-type amphoteric surfactants such as coconut oil fatty acid amidopropyl dimethylamino acetic acid betaine, palm kernel oil fatty acid amidopropyl dimethylamino acetic acid betaine, beef tallow fatty acid amidopropyl dimethylamino acetic acid betaine, hardened beef tallow fatty acid amidopropyl dimethylamino acetic acid betaine, lauric amidopropyl dimethylamino acetic acid betaine, myristic amidopropyl dimethylamino acetic acid betaine, palmitic amidopropyl dimethylamino acetic acid betaine, stearic amidopropyl dimethylamino acetic acid betaine, oleic amidopropyl dimethylamino acetic acid betaine, and the like; alkyl sulfobetaine-type amphoteric surfactants such as coconut oil fatty acid dimethyl sulfopropyl betaine and the like; alkylhydroxy sulfobetaine-type amphoteric surfactants such as lauryl dimethylaminohydroxy sulfobetaine and the like; phosphobetaine-type amphoteric surfactants such as laurylhydroxy phosphobetaine and the like; amidoamino acid-type amphoteric surfactants such as sodium N-lauroyl-N'-hydroxyethyl-N'-carboxymethyl ethylenediamine, sodium N-oleoyl-N'-hydroxyethyl-N'-carboxymethyl ethylenediamine, sodium N-cocoyl-N'-hydroxyethyl-N'-carboxymethyl ethylenediamine, potassium N-lauroyl-N'-hydroxyethyl-N'-carboxymethyl ethylenediamine, potassium N-oleoyl-N'-hydroxyethyl-N'-carboxymethyl ethylenediamine, sodium N-lauroyl-N-hydroxyethyl-N'-carboxymethyl ethylenediamine, sodium N-oleoyl-N-hydroxyethyl-N'-carboxymethyl ethylenediamine, sodium N-cocoyl-N-hydroxyethyl-N'-carboxymethyl ethylenediamine, monosodium N-lauroyl-N-hydroxyethyl-N',N'-dicarboxymethyl ethylenediamine, monosodium N-oleoyl-N-hydroxyethyl-N',N'-dicarboxymethyl ethylenediamine, monosodium N-cocoyl-N-hydroxyethyl-N',N'-dicarboxymethyl ethylenediamine, disodium N-lauroyl-N-hydroxyethyl-N',N'-dicarboxymethyl ethylenediamine, disodium N-oleoyl-N-hydroxyethyl-N',N'-dicarboxymethyl ethylenediamine, disodium N-cocoyl-N-hydroxyethyl-N',N'-dicarboxymethyl ethylenediamine, and the like.

Examples of semipolar surfactants include alkylamine oxide-type surfactants, alkylamine oxides, alkylamide amine oxides, alkylhydroxyamine oxides, and the like. Alkyldimethylamine oxides having from 10 to 18 carbons, alkoxyethyl dihydroxyethylamine oxides having from 8 to 18 carbons, and the like are preferably used. Specific examples thereof include dodecyldimethylamine oxide, dimethyloctylamine oxide, diethyldecylamine oxide, bis-(2-hydroxyethyl)dodecylamine oxide, dipropyltetradecylamine oxide, methylethylhexadecylamine oxide, dodecylamidopropyldimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, stearyldimethylamine oxide, isostearyldimethylamine oxide, coconut fatty acid alkyldimethylamine oxide, caprylic amide propyldimethylamine oxide, capric amide propyldimethylamine oxide, lauric amide propyldimethylamine oxide, myristic amide propyldimethylamine oxide, palmitic amide propyldimethylamine oxide, stearic amide propyldimethylamine oxide, isostearic amide propyldimethylamine oxide, oleic amide propyldimethylamine oxide, ricinoleic amide propyldimethylamine oxide, 12-hydroxystearic amide propyldimethylamine oxide, coconut fatty acid amide propyldimethylamine oxide, palm kernel oil fatty acid amide propyldimethylamine oxide, castor oil fatty acid amide propyldimethylamine oxide, lauric amide ethyldimethylamine oxide, myristic amide ethyldimethylamine oxide, coconut fatty acid amide ethyldimethylamine oxide, lauric amide ethyldiethylamine oxide, myristic amide ethyldiethylamine oxide, coconut fatty acid amide ethyldiethylamine oxide, lauric amide ethyldihydroxyethylamine oxide, myristic amide ethyldihydroxyethylamine oxide, and coconut fatty acid amide ethyldihydroxyethylamine oxide.

In addition to the components described above, the topical composition or cosmetic composition of the present invention may include a variety of components such as oil-soluble gelling agents, pH adjusting agents, antioxidants, chelating agents, moisturizing components, perfumes, and the like, provided that such use does not impair the effects of the present invention.

Examples of the oil-soluble gelling agent include amino acid derivatives such as N-lauroyl-L-glutamic acid, α,γ-di-n-butylamine, and the like; dextrin fatty acid esters such as dextrin palmitate, dextrin stearate, dextrin 2-ethylhexanoate palmitate, and the like; sucrose fatty acid esters such as sucrose palmitate, sucrose stearate, and the like; fructooligosaccharide fatty acid esters such as inulin stearate, fructooligosaccharide 2-ethylhexanoate, and the like; benzylidene derivatives of sorbitol such as monobenzylidene sorbitol, dibenzylidene sorbitol, and the like; and the like.

Examples of pH adjusting agents include lactic acid, citric acid, glycolic acid, succinic acid, tartaric acid, dl-malic acid, potassium carbonate, sodium hydrogen carbonate, ammonium hydrogen carbonate, and the like.

Chelating agents act by insolubilizing mineral ions in water, and examples thereof include EDTA, alanine, sodium salt of edetic acid, sodium polyphosphate, sodium metaphosphate, and phosphoric acid.

Examples of the antioxidants include tocopherol, butylhydroxyanisole, dibutylhydroxytoluene, phytic acid, and the like. Examples of the chelating agent include alanine, sodium salt of edetic acid, sodium polyphosphate, sodium metaphosphate, phosphoric acid, and the like.

Examples of moisturizing components include hyaluronic acid, chondroitin sulfate, pyrrolidone carboxylic acid salts, polyoxyethylene methylglucoside, polyoxypropylene methylglucoside, and the like. Moreover, it goes without saying that polyhydric alcohols and the like exhibit the function of retaining moisture on the skin or hair. With the cosmetic composition of the present invention, there are cases in which moisture retention properties of the moisturizing agent can be improved by using these moisturizing components in combination with other oil-based raw materials, selecting a gel formulation form for the cosmetic composition, or using the moisturizing components in combination with a membrane forming component.

Specific examples of products that the cosmetic composition of the present invention can be used for include skin cleansing agent products, skin care products, makeup products, anti-perspirant products, ultraviolet light blocking products, and similar skin use cosmetic products; hair use cleansing agent products, hair dressing products, hair use coloration products, hair growth products, hair rinsing products, hair conditioning products, hair treatment products, and similar hair use cosmetic products; and bath use cosmetic products. Examples of the topical composition of the present invention include hair regrowth agents, hair growth promoters, analgesics, germicides, anti-inflammatory agents, refreshing agents, and skin anti-aging agents, but are not limited thereto.

The skin use cosmetic products can be used on any site of the entire body including the scalp, face (including lips, eyebrows, and cheeks), fingers, and fingernails. Specific examples thereof include cleansing gels, cleansing creams, cleansing foams, face washing creams, eye makeup removers, face washing foams, liquid soaps (body soaps), hand soaps, gel soaps, shaving creams, nail polish removers, acne treatment cosmetic compositions, and similar skin cleansing agent products; skin creams, scalp treatments, skin milks, milk lotions, emulsions, facial packs, body powders, essences, shaving lotions, massage lotions, and similar skin care products; foundations, liquid foundations, oil-based foundations, makeup bases, powders, face powders, lip creams, lipsticks, lip glosses, eye creams, eyebrow pencils, eyelash cosmetic products, and similar makeup products; deodorants and similar anti-perspirants; and sunscreen agents, tanning use medicaments (sun tanning agent), and similar ultraviolet light blocking products.

Examples of scalp use cosmetic products include shampoos, rinse-in shampoos, and similar hair use cleansing agents; hair waxes, hair use curl holding agents, setting agents, hair creams, hairsprays, hair liquids, and similar hair dressing products; hair coloring substances, hair color sprays, hair color rinses, hair color sticks, and similar hair use coloration products; hair tonics, hair treatment essences, hair packs, and similar hair growing products; and oil rinses, cream rinses, treatment rinses, hair conditioners, hair treatments, and similar hair rinse or hair conditioning products. In addition, examples of bath use cosmetic products include bath foams.

The form of the cosmetic composition or cosmetic product according to the present invention is not particularly limited, and these can be preferably used in the form of a liquid, W/O emulsion O/W emulsion, W/O cream-form, O/W cream-form, solid, paste-form, gel-form, powder-form, multi-layer, mousse-form, mist-form, granule, flake, crushed stone, and similar forms. Particularly preferable forms are W/O creams, solids, pastes, gels, and powders, and these forms are useful as forms of a cosmetic composition or cosmetic product that make use of the thickened or gelled characteristics imparted by the gelling agent and thickening agent of the present invention.

A container of the cosmetic composition or cosmetic product according to the present invention is also not particularly limited, and any container such as a jar, pump, tube, bottle, pressurized can dispensing container, pressure resistant aerosol container, light-blocking container, compact container, cosmetic receptacle (kanazara), stick container, repeating container, spray container, divided container provided with a compound liquid dispensing opening, and the like can be filled with the cosmetic composition or cosmetic product. Normal silicone-based formulations tend to separate easily in tubes, but the cosmetic composition or cosmetic product according to the present invention has excellent stability and therefore has the benefit that the cosmetic composition or cosmetic product according to the present invention can be stored stably, even when charged into a tube container.

Anti-Perspirant Composition

As described above, the co-modified organopolysiloxane according to the present invention is a gelling agent or thickening agent having excellent versatility, and can be used widely as a composition to be applied as a cosmetic composition or a medicament to the human body. Next, a specific example of use as an anti-perspirant composition will be described. An anti-perspirant composition according to the present invention can be selected from any of a water-in-oil emulsion type gel anti-perspirant, a stick form formulation, and a spray or similar aerosol formulation. Components thereof are dependent on the type of formulation selected, and can be appropriately selected from the cosmetic composition components described above. Particularly, the anti-perspiration active component compounded in an aqueous phase or an oil phase preferably optionally includes the deodorant component, as described above.

Water-In-Oil Emulsion Type Gel Anti-Perspirant

In a water-in-oil emulsion type gel anti-perspirant, which is one embodiment of the present invention, an oil phase component comprising the co-modified organopolysiloxane (for example, an oil-based cosmetic raw material such as a co-modified organopolysiloxane, volatile oil agent, nonvolatile oil agent, solubilization agent or the like) is mixed with an aqueous phase component according to an arbitrary method. In such cases, in order to ensure transparency, the refractive index of each phase is preferably adjusted in order to improve the stability and transparency of the water-in-oil emulsion type gel anti-perspirant.

A moisturizing feel and a natural feeling on the skin without discomfort can be imparted by compounding the co-modified organopolysiloxane of the present invention in the water-in-oil emulsion type gel anti-perspirant. Additionally, the co-modified organopolysiloxane of the present invention can also function as an emulsifier for stably emulsifying/dispersing the aqueous phase including the anti-perspiration active component in the oil phase. A compounded amount thereof is from 0.1 to 10 parts and preferably from 0.5 to 5 parts by weight, when the entire composition is considered to be 100 parts by weight. Furthermore, in the anti-perspirant of the present invention, by using the method of adjusting the transparency of the emulsion, there is a benefit in that a transparent water-in-oil emulsion type gel anti-perspirant having excellent transparency can be obtained.

The usage amount of the volatile oil that is the base oil of the water-in-oil emulsion type gel anti-perspirant is from 5 to 40 parts, preferably from 10 to 30 parts, and more preferably from 15 to 20 parts by weight, when the entire composition is considered to be 100 parts by weight. Those products among the examples recited for component (D) of the present invention that have a vapor pressure measured at 25° C. can be used as the volatile oil. Specifically, the vapor pressure at 25° C. of the volatile oil is from 0.01 to 8 hPa and preferably from 0.02 to 2.0 hPa; and the volatile oil has a boiling point at 1 atmosphere of less than 250° C.

In the water-in-oil emulsion type gel anti-perspirant, the types and compounded amounts of the anti-perspiration active component and the deodorant component are as described above and can be suitably adjusted as desired.

Examples of the nonvolatile oil agent include those products that are not "volatile oils" recited for the oil-based raw material in the present invention; the components recited for component (C) of the present invention; ether oils such as dioctyl ethers and the like; dioctyl carbonates, dioctadecyl carbonates, and similar carbonate ester oils; neopentyl glycol dicaprates and similar ester oils; polyalkylene glycol and derivatives thereof; and the like. These have an emollient effect and also have the effect of adjusting the feeling to touch and form of the water-in-oil emulsion type gel anti-perspirant. A compounded amount of the nonvolatile oil is, as described above, from 1 to 10 parts by weight and preferably from 2 to 8 parts by weight.

A solubilization agent can be used in the water-in-oil emulsion type gel anti-perspirant of the present invention. These solubilization agents are selected from the products recited for the oil-based raw material component (D) in the present invention, oils and fats normally used in cosmetic compositions, higher alcohols, higher fatty acids, organic-based oleophilic surfactants, and the like; and generally are selected from the oil agent used as the base oil, the oil agent used as the refractive index adjuster, and an oil agent different from the nonvolatile oil. However, the refractive index adjuster, base oil, or nonvolatile oil may function as the solubilization agent. A compounded amount of the solubilization agent is from about 0.1 to about 20 parts and preferably from 1.0 to 10.0 parts by weight of the entire composition.

Other components that may be present in the water-in-oil emulsion type gel anti-perspirant of the present invention include the components (F), (G), (H), and (J) of the present invention. Proportions of these components are normally from 0 to 8 parts by weight, when the entire composition is considered to be 100 parts by weight, but are not limited thereto.

Those surfactants that have already been given as examples may also be added to the water-in-oil emulsion type gel anti-perspirant of the present invention. These encompass any hydrophilic emulsifier with an HLB greater than 8. A compounded amount thereof is generally from 0 to 2 parts by weight per 100 parts by weight of the entire composition. However, it is understood that adjusting this proportion based on the desired HLB of the system is obvious to one having ordinary skill in the art. Examples of hydrophilic nonionic surfactants preferable as the surfactant include POE-sorbitan fatty acid esters; POE sorbit fatty acid esters; POE-glycerin fatty acid esters; POE-fatty acid esters; POE-alkyl ethers; pluronic-types; POE-POP-alkyl ethers; tetra POE-tetra POP-ethylenediamine condensates; POE-castor oil hydrogenated castor oil derivatives; POE-beeswax-lanolin derivatives; alkanolamides; POE-propylene glycol fatty acid esters; POE-alkylamines; POE-fatty amides; sucrose fatty acid esters; alkylethoxydimethyl amine oxides; trioleyl phosphates; and the like.

Various components other than the components described above can be used in the topical composition (e.g. the anti-perspirant composition) of the present invention, provided that such use does not impair the effects of the present invention. Examples thereof include thickening agents, oil-soluble gelling agents, organo-modified clay minerals, bioactive components, skin beautifying components, pH adjusting agents, antioxidants, solvents, chelating agents, moisturizing components, medicaments, and the like.

The anti-perspirant composition according to the present invention is used by applying an amount thereof to the underarms or other sites sufficient to suppress perspiration and/or odor. Preferably about 0.1 to 10 g, more preferably 0.1 to 5 g, and even more preferably 0.1 to 1 g is applied at the target site on the skin.

Nonaqueous Stick-Form Anti-Perspirant Composition

Next, a stick-form anti-perspirant composition, which is an embodiment of the present invention, will be described. The stick-form anti-perspirant composition is a form of a solid anti-perspirant composition and may be in a hydrous form such as a solid W/O emulsion or the like if the gelling agent or thickening agent according to the present invention is contained therein, and can also be a substantially water-free preparation for external use. Here, an example of a substantially water-free system will be described. The nonaqueous stick-form anti-perspirant composition is effective in obtaining superior stability and a dry sensation during use.

An oil phase component such as a co-modified organopolysiloxane, a volatile oil agent, a higher alcohol, a wax, a nonvolatile oil agent, or the like is mixed in the nonaqueous stick-form anti-perspirant composition, which is an embodiment of the present invention. The mixture is heated to the melting temperature (e.g. about 80° C.) of the solid component such as the higher alcohol, the wax, or the like, and agitated. Thus, a single liquid phase is formed. A temperature slightly higher than a solidification point of the system (e.g. about 65° C.) is maintained, the remaining components other than the anti-perspiration active component are added while agitating, and then the active component is added. After thoroughly mixing, the mixture is poured into a container and allowed to solidify at room temperature. Thus, the stick-form anti-perspirant composition is manufactured. Note that the agitating can be performed using a mechanical force by means of an apparatus such as a mixer or the like.

Moisturizing feel and a natural feeling on the skin free of discomfort can be imparted by compounding the co-modified organopolysiloxane of the present invention in the nonaqueous stick-form anti-perspirant composition. Therefore, in cases when a sensation of dryness is excessive, this sensation can be mitigated and a natural sensation during use can be obtained. Additionally, particle agglomeration can be suppressed due to the co-modified organopolysiloxane of the present invention being effectively adsorbed on the surface of the powder or solid microparticles and, therefore, the powder or solid microparticles can be stably and uniformly dispersed in the oil. As a result, the nonaqueous stick-form anti-perspirant composition including the co-modified organopolysiloxane of the present invention has the benefit that there is little white residue after application and drying. Furthermore, the co-modified organopolysiloxane of the present invention has excellent compatibility with higher alcohols, waxes, and similar solid oils and, therefore, the degree of hardness of the stick can be controlled and the generation of white deposit originating from the solid oil after application and drying can be mitigated. A compounded amount thereof is from 0.1 to 10 parts by weight and preferably from 0.5 to 5 parts by weight, when the entire composition is considered to be 100 parts by weight.

One or more types of volatile oil agents can be used in the nonaqueous stick-form anti-perspirant composition according to the present invention, and a compounded amount thereof is from 5 to 70 wt. % and, from the standpoint of obtaining excellent feeling to touch, is preferably from 10 to 60 wt. % of the entire composition.

In the nonaqueous stick-form anti-perspirant composition according to the present invention, any of the components described above can be used as the anti-perspiration active component without any particular restrictions. However, as the composition is a nonaqueous system, water soluble salts and the like are preferably used in their solid states and are dispersed in the composition as microparticles. An average diameter of the microparticles of the anti-perspiration active component is preferably from about 0.1 to 100 µm, more preferably from 0.1 to 20 µm, and even more preferably from 0.1 to 10 µm. On the other hand, by using relatively small particles having an average diameter in a range from 0.5 to 8 µm and relatively large particles having an average diameter in a range from 12 to 50 µm in combination, feeling to touch properties such as sliding feel and the like when applying the stick-form anti-perspirant composition can be improved.

One or more types of the anti-perspiration active component can be used in the nonaqueous stick-form anti-perspirant composition, and a compounded amount thereof is preferably from 10 to 70 wt. %, more preferably from 15 to 50 wt. %, and even more preferably from 15 to 25 wt. % of the entire composition because the effects of suppressing perspiration and odor can be sufficiently obtained and feeling to touch is excellent. Additionally, the deodorant agent described above can be compounded in conjunction with or in place of the anti-perspiration active component, and the type and compounded amount thereof are as described above.

The higher alcohol that can be used in the nonaqueous stick-form anti-perspirant composition according to the present invention has from 12 to 50 carbons, preferably from 16 to 30 carbons, and more preferably from 18 to 24 carbons. If the higher alcohol is within this range, excellent feeling to touch can be obtained. Specific examples thereof include cetyl alcohol, stearyl alcohol, arachidyl alcohol, behenyl alcohol, and the like. One or more types of higher alcohols can be used, and a compounded amount thereof is from 1 to 50 wt. %, preferably from 5 to 35 wt. %, and more preferably from 10 to 25 wt. % of the entire composition. If the higher alcohol is within this range, suitable formativeness and excellent feeling to touch can be obtained.

Examples of the nonvolatile oil agent that can be used in the nonaqueous stick-form anti-perspirant composition according to the present invention include those products that are not "volatile oils" recited for the oil agent component (D) in the present invention; various silicone oils; mineral oils and polydecenes; hydrogenated polyisobutene and similar hydrocarbon oils; the component (C) of the present invention; dioctyl ethers and similar ether oils; dioctyl carbonate, dioctadecyl carbonate, and similar carbonate ester oils; isopropyl palmitate, isopropyl myristate, lauryl myristate, diisopropyl sebacate, diisopropyl adipate, benzoic acid alkyls having from 8 to 18 carbons, and similar ester oils; PPG-3 myristyl ether, PPG-14 butyl ether, and similar polyalkylene glycols and derivatives thereof; isostearyl alcohol and oleyl alcohol; 2-ethylhexyl alcohol; organo-oleophilic surfactants; and the like. These oil agents have, in addition to emollient effects, effects of adjusting the feeling to touch and the form, and also may function as a compatibility accelerator of the oil phase. One or more types of nonvolatile oil agents can be used, and a compounded amount thereof is from 1 to 30 wt. % and preferably from 5 to 15 wt. % of the entire composition.

The nonaqueous stick-form anti-perspirant composition according to the present invention can further include a wax. This is preferable because stability at elevated temperatures will improve. Examples of the wax include the component (D) described above, oils and fats, and higher fatty acids, which are solid at room temperature. Preferable examples include hydrogenated castor oil, fatty acid, wax-like modified silicones, and glycerol monostearate; 2-8178 Gellant, 2-8179 Gellant, and the like (manufactured by Dow Corning Corporation, in the USA); AMS-C30 Cosmetic Wax, 2503 Cosmetic Wax, and the like (manufactured by Dow Corning Corporation, in the USA); alkyl-modified silicone resin wax; and the like. Such products impart suitable hardness and stability to the obtained stick-form anti-perspirant composition.

One or more types of waxes can be used, and a compounded amount thereof is from 1 to 10 wt. % and, from the perspective of obtaining excellent stability and excellent feeling to touch, is preferably from 2 to 8 wt. % of the entire composition.

Furthermore, in the nonaqueous stick-form anti-perspirant composition according to the present invention, a ratio of a total weight "X" of the oil phase component (except the volatile oil and the solid oil) to a total weight "Y" of the anti-perspiration active component and the deodorant agent is such that X/Y=1/7 to 5/6 and, from the standpoints of being able to further suppress white residue while maintaining high feeling to touch and anti-perspirant deodorant performance, is preferably such that X/Y=1/6 to 2/3.

Moreover, other components that can be present in the nonaqueous stick-form anti-perspirant composition according to the present invention include the components (F), (G), (H), and (J), and the proportions of these components are generally from about 0 parts to 8 parts relative to the total weight of the composition, but are not limited thereto. Additionally, various components other than the components described above can be used provided that such use does not impair the effects of the present invention. Examples thereof include thickening agents, oil-soluble gelling agents, organo-modified clay minerals, bioactive components, skin beautifying components, pH adjusting agents, antioxidants, solvents, chelating agents, moisturizing components, medicaments, and the like.

The anti-perspirant composition according to the present invention is used by applying an amount thereof to the underarms or other sites sufficient to suppress perspiration and/or odor. Preferably about 0.1 to 10 g, more preferably 0.1 to 5 g, and even more preferably 0.1 to 1 g is applied at the target site on the skin. Additionally, the stick composition of the present invention is preferably applied once or twice per day in order to effectively suppress perspiration and/or odor.

Aerosol Anti-Perspirant Composition

Next, an aerosol anti-perspirant composition, which is a preparation for external use including the co-modified organopolysiloxane according to the present invention and is an embodiment of the present invention, will be described. The aerosol anti-perspirant composition may be in a hydrous form and can also be a substantially water-free preparation for external use. Nonaqueous aerosol anti-perspirant compositions provide an advantage of a dry sensation during use and, on the other hand, hydrous aerosol anti-perspirant compositions provide advantages of effectively suppressing perspiration and easily attaining a feeling of freshness.

The aerosol anti-perspirant composition according to the present invention can include a propellant, a powder component dispersed therein (e.g. an anti-perspiration active component, a deodorant agent, or a usage enhancing component), a co-modified organopolysiloxane, a liquid oil agent, and the like. Moreover, the co-modified organopolysiloxane can be compounded in the form of the aforementioned gel composition.

The anti-perspiration active component in the aerosol anti-perspirant composition according to the present invention may be in the form of a powder or a solution. When a powder, the anti-perspiration active component is preferably dispersed in the composition as microparticles. An average diameter of the microparticles is preferably from about 0.1 to 100 μm, more preferably from 0.1 to 20 μm, and even more preferably from 0.1 to 10 μm. When in the form of a solution, an aqueous solution can also be used, but in order to further enhance storage stability and the like of the composition, a material in which an AP active component is complexed with or dissolved in propylene glycol, polyethyleneglycol, an alkylglycerol ether, an alkyl etherified sugar, an alkyl etherified sugar alcohol, or a similar polyol is more preferably used. Examples of the anti-perspiration active component that can be used in the aerosol anti-perspirant composition according to the present invention include the same examples described above.

One or more types of the anti-perspiration active component can be used, and a compounded amount thereof is preferable from 0.001 to 20.0 wt. % and more preferably from 0.1 to 10.0 wt. % of the entire weight of the aerosol anti-perspirant composition.

Examples of a deodorant agent that can be used in conjunction with or in place of the anti-perspiration active component in the aerosol anti-perspirant composition according to the present invention include antimicrobial agents (germicides or fungicides), bacteriostatic agents, odor absorbing substances, deodorizers, perfumes, and the like. Specific examples thereof are as described above, and a compounded amount of the deodorant agent is preferably from 0.01 to 10.0 wt. % and more preferably from 0.1 to 3.0 wt. % of the entire weight of the aerosol anti-perspirant composition.

Additionally, because the aerosol anti-perspirant composition includes the co-modified organopolysiloxane of the present invention, particle agglomeration can be suppressed due to the co-modified organopolysiloxane of the present invention being effectively adsorbed on the surface of the powder or solid microparticles and, therefore, the powder or solid microparticles can be stably and uniformly dispersed in the system. As a result, with the aerosol anti-perspirant composition including the co-modified organopolysiloxane of the present invention, advantages are expected of reduced clogging of the aerosol valve, whiteness after use being not noticeable, and improved uniform adhesion to the skin. Additionally, depending on the AP active component and/or deodorant agent, drying or tightening of the skin may be felt after use, dry skin or declines in the elasticity of the skin may occur, or unnatural skin sensation may be experienced. However, these inconveniences are expected to be mitigated through use of the co-modified organopolysiloxane of the present invention. A compounded amount thereof is about 0.1 to about 10 parts and preferably from about 0.5 parts to about 5 parts.

In order to impart a dry feeling to touch to the skin, a particle size of the powder is preferably from 1 to 20 μm and more preferably from 5 to 15 μm. If the particle size is greater than 20 μm, abrasiveness will be felt, and if less than or equal to 1 μm, particle scattering may occur.

Examples of the propellant used in the present invention include gaseous vehicles. Specific examples include propane, n-butane, isobutane, isopentane, pentane, dimethylether, liquified petroleum gas (LPG), liquified natural gas, and the like. Of these, LPG, dimethylether, and isopentane are preferable. A single type of propellant may be used or two or more types may be combined. It is also possible to compound an alternative freon such as 1,1-difluoroethane or the like or a freon gas, but this is not preferable from an environmental standpoint. Additionally, from the standpoints of environment and safety, carbon dioxide gas or nitrogen gas can also be used. An amount of propellant charged is not particularly limited and can be determined appropriately according to conventional methods.

Exemplary powder components other than the AP active component and the deodorant agent that can be included in the aerosol anti-perspirant composition according to the present invention include usage enhancing components. Examples of usage enhancing components include products that have the ability to impart a feeling of dryness to the skin, such as silica gel, talc, bentonite, kaolinite, regular spherical shape silica, smectite, surface treated materials of the same, and similar inorganic powders; polyethylene powder, nylon powder, polystyrene powder, crosslinking organopolysiloxane powder, organopolysiloxane elastomer spherical powder, silicone resin powder, and similar organic powders; composite powders such as inorganic powders including a metallic oxide; and the like. That is, the usage enhancing components can be the components (B) and (C) of the present invention. One of these usage enhancing components may be used or a combination of two or more may be used.

Examples of the liquid oil agent compounded in the aerosol anti-perspirant composition according to the present invention include those products recited for the oil agent component (D) in the present invention that are liquid at room temperature. The liquid oil agent has the effects of uniformly adhering the powder on the skin and enhancing sensation during use. Combinations of one or two or more of these liquid oil agents can be used. Not only from the perspective of feeling to touch, but also from the perspectives of emollient effect and formulation flexibility, it is preferable that the liquid oil agent include a silicone oil. In order to obtain a dry feeling to touch that is free of stickiness, a preferable range of the viscosity of the silicone oil is 100,000 cst (25° C.) or less, and a more preferable range is 100 cst (25° C.) or less. Note that a compounded amount of the liquid oil agent is preferably from 0.1 to 50 wt. % and more preferably from 0.5 to 25 wt. % of the entire weight of the aerosol anti-perspirant composition. If the compounded amount is less than 0.1 wt. %, a dry feeling to touch of the oil will not be displayed and compatibility on the skin will be poor; and if greater than 50 wt. %, sensation during use may decline due to non-adhesion to the skin and/or the stability of the formulation may be negatively affected.

When the aerosol anti-perspirant composition according to the present invention includes the liquid oil agent, the liquid oil agent can be pre-emulsified and compounded in the form of an O/W emulsion. This is effective in cases where dispersing the liquid oil agent as-is stably and uniformly in the aerosol anti-perspirant composition is difficult due to the viscosity of the liquid oil agent being high, and other reasons. Here, an O/W emulsion formulation provided with resistance to alcohols (described hereinafter) is preferable; and using a phosphate-based surfactant or a nonionic surfactant having an oleyl group as the surfactant is effective from the perspective of obtaining an O/W emulsion having excellent compounding stability. Additionally, an O/W emulsion with excellent compounding stability can be obtained by using a combination of a phosphate-based surfactant and a general nonionic surfactant.

The aerosol anti-perspirant composition according to the present invention can further include water, ethanol, IPA, a polyhydric alcohol, a surfactant, or the like for the purpose dissolving the anti-perspiration active component in the system and more effectively displaying perspiration suppression effects. However, when a compounded amount of ethanol, IPA, and similar lower monohydric alcohols and some polyhydric alcohols such as propylene glycol and 1,3-butylene glycol is great, there is a tendency for inflammation or irritation to occur at sites where the skin is sensitive, such as the armpits, during application and after application. Therefore, the compounded amount of the lower monohydric alcohol is preferably not more than 50 wt. % of the entire weight of the aerosol anti-perspirant composition. Additionally, the compounded amount of the polyhydric alcohol that tends to cause irritation and the like at sites where the skin is sensitive is preferably not more than 20 wt. % of the entire weight of the aerosol anti-perspirant composition. A preferable polyhydric alcohol is the component recited as the "refractive index adjuster of the aqueous phase". Regarding water, a weight ratio of the anti-perspiration active component to water (anti-perspiration active component/water) is preferably in a range from 1/0.5 to 1/2. When the weight ratio is within this range, the following effects can be expected: further enhancing of perspiration suppression effects without a feeling of stickiness occurring, and rapid expression thereof.

Compounding the surfactant is effective in increasing the stability of hydrous aerosol anti-perspirant compositions. Specifically, nonaqueous aerosol anti-perspirant compositions are manufactured according to a conventional method in which a stock solution is prepared by first mixing the components other than the propellant and the powder; then, the powder is dispersed uniformly in this stock solution; and, thereafter, the propellant is charged. As a result, stability problems do not easily occur. On the other hand, when a hydrous aerosol anti-perspirant composition is manufactured according to the same method, there are problems in that the stability of the system declines when the liquified petroleum gas (LPG) or similar propellant is compounded, and the perspiration component and similar components are prone to separate as a deposit. Therefore, the type and amount of the liquid oil agent that can be compounded becomes limited, and countermeasures such as reducing the concentration of the AP active component and increasing the compounded amount of the alcohol have become necessary. This has lead to a decrease in the degree of freedom of formulation. However, these problems can be mitigated by compounding an appropriate surfactant.

From the standpoints of the anti-perspiration active component being acidic and obtaining dispersion stability effects of the aerosol anti-perspirant composition system, the appropriate surfactant is preferably one or two or more types of nonionic or weakly acidic surfactants. Of these, polyoxyethylene polyoxypropylene cetyl ether phosphate and polyoxyethylene oleyl ether phosphate are preferable.

A compounded amount of this surfactant is preferably from 0.1 to 25 wt. % and more preferably from 0.1 to 10 wt. % of the entire weight of the aerosol anti-perspirant composition. If the compounded amount is less than 0.1 wt. %, the stability enhancing effect of the formulation will be poor and, taking into consideration the purpose of compounding, exceeding 25 wt. % is not cost effective and will lead to a decline in sensation during use.

Moreover, other components that can be present in the aerosol anti-perspirant composition according to the present invention include the components (F), (G), (H), and (J) of the present invention, and while proportions of these components are generally from about 0 parts to 8 parts per the total weight of the composition, said proportions are not limited thereto. Additionally, various components other than the components described above can be used provided that such use does not impair the effects of the present invention. Examples thereof include thickening agents, oil-soluble gelling agents, organo-modified clay minerals, bioactive components, skin beautifying components, pH adjusting agents, antioxidants, solvents, chelating agents, moisturizing components, medicaments, and the like.

A conventional aerosol container can be used for the aerosol anti-perspirant composition according to the present invention. Alternately, the aerosol anti-perspirant composition according to the present invention can be sprayed using an aerosol container in which an inner surface thereof has been coated with a resin coating for the purpose of preventing rust or the like. The aerosol anti-perspirant composition according to the present invention can also be sprayed using a double-layer container that is provided with an inner pouch.

The anti-perspirant composition according to the present invention is used by applying an amount thereof to the underarms or other sites, by spraying, sufficient to suppress perspiration and/or odor. Preferably about 0.1 to 5 g, more preferably 0.1 to 3 g, and even more preferably 0.1 to 1 g is applied at the target site on the skin. Additionally, the aerosol anti-perspirant composition of the present invention is preferably applied by spraying once or twice per day in order to effectively suppress perspiration and/or odor.

EXAMPLES

Hereinafter, the present invention is described with reference to examples, but it should be understood that the present invention is not limited to these examples. In the following compositional formulae, "Me" represents a methyl (—$CH_3$) group, "M" represents a $Me_3SiO$ group (or an $Me_3Si$ group), "D" represents an $Me_2SiO$ group, "$M^H$" represents an MeHSiO group, and "$M^R$" and "$D^R$" respectively represent units in which a methyl group in "M" or "D" is modified by any substituent. Additionally, in the manufacturing examples, "IPA" represents isopropyl alcohol.

Production Example 1

Synthesis of Silicone Compound No. 1

196.6 g of a methylhydrogenpolysiloxane expressed by the mean structural formula $MD_{400}D^H{}_{10}M$, 13.6 g of a vinyl tris(trimethylsiloxy)silane expressed by the mean structural formula $CH_2$=CH—$Si(OSiMe_3)_3$, 5.5 g of a glycerin monoallyl ether expressed by the structural formula $CH_2$=CH—$CH_2$—$OCH_2CH(OH)CH_2OH$, and 90 g of isopropyl alcohol (hereinafter abbreviated to IPA) were placed in a reaction vessel, and heated to 70° C. while agitating under a nitrogen stream. 0.060 g of an IPA solution of a platinum-1,3-divinyl-1,1,3,3-tetramethyldisiloxane complex (Pt concentration: 4.5 wt. %) was added and the mixture was reacted for 5 hours at 80° C. Then, 2 g of the reaction liquid was sampled and it was confirmed that the reaction was complete through an alkali decomposition gas generation method (the remaining Si—H groups were decomposed using a KOH ethanol/water solution, and the reaction rate was calculated from the volume of the generated hydrogen gas). The reaction liquid was heated under reduced pressure so as to distil off low-boiling components, thereby obtaining a composition containing a novel glycerin-modified silicone having a siloxane dendron structure expressed by the mean structural formula $MD_{400}D^{R*31}{}_5D^{R*21}{}_5M$ (silicone compound No. 1).

In this formula, $R^{*21}$ and $R^{*31}$ are as described below.
$R^{*21}$=—$C_3H_6OCH_2CH(OH)CH_2OH$
$R^{*31}$=—$C_2H_4Si(OSiMe_3)_3$ This composition was a light yellow color uniform viscous liquid having semi-transparency.

Production Example 2

Synthesis of Silicone Compound No. 2

198.7 g of a methylhydrogenpolysiloxane expressed by the mean structural formula $MD_{400}D^H{}_{10}M$, 8.2 g of a vinyl tris(trimethylsiloxy)silane expressed by the mean structural formula $CH_2$=CH—$Si(OSiMe_3)_3$, 5.6 g of a glycerin monoallyl ether expressed by the structural formula $CH_2$=CH—$CH_2$—$OCH_2CH(OH)CH_2OH$, 2.4 g of 1-decene, and 90 g of IPA were placed in a reaction vessel, and heated to 70° C. while agitating under a nitrogen stream. 0.050 g of an IPA solution of a platinum-1,3-divinyl-1,1,3,3-tetramethyldisiloxane complex (Pt concentration: 4.5 wt. %) was added and the mixture was reacted for 3 hours at 80° C. Then, 2 g of the reaction liquid was sampled and it was confirmed that the reaction was complete through an alkali decomposition gas generation method. The reaction liquid was heated under reduced pressure so as to distil off low-boiling components, thereby obtaining a composition containing a novel glycerin-modified silicone having an alkyl group and a siloxane dendron structure expressed by the mean structural formula $MD_{400}D^{R*11}{}_2D^{R*31}{}_3D^{R*21}{}_5M$ (silicone compound No. 2).

In this formula, $R^{*21}$ and $R^{*31}$ are the same as described above, and $R^{*11}=-C_{10}H_{21}$.

This composition was a light yellowish-brown, semi-transparent uniform liquid.

Production Example 3

Synthesis of Silicone Compound No. 3

109.3 g of a methylhydrogenpolysiloxane expressed by the mean structural formula $MD_{72}D^H{}_{12}M$, 66.3 g of a vinyl tris(trimethylsiloxy)silane expressed by the mean structural formula $CH_2=CH-Si(OSiMe_3)_3$, 24.3 g of a polyglycerin monoallyl ether, 200 g of IPA, and 0.23 g of a 2.3 wt. % sodium acetate/methanol solution were placed in a reaction vessel, and heated to 50° C. while agitating under a nitrogen stream. 0.160 g of an IPA solution having 5 wt. % of chloroplatinic acid was added, and the mixture was reacted for 7 hours at 80° C. Then, 2 g of the reaction liquid was sampled and it was confirmed that the reaction was complete through an alkali decomposition gas generation method. The reaction liquid was heated under reduced pressure so as to distil off low-boiling components, thereby obtaining a composition containing a novel polyglycerin-modified silicone having a siloxane dendron structure expressed by the mean structural formula $MD_{72}D^{R*31}{}_9D^{R*22}{}_3M$ (silicone compound No. 3).

In this formula, $R^{*31}$ is the same as described above.

Moreover, the polyglycerin monoallyl ether was synthesized by ring-opening polymerizing 3 molar equivalents of glycidol with 1 mole of a glycerin monoallyl ether, and had a structure in which an average of 4 moles of glycerin were added. Moreover, the glycerin monoallyl ether has two hydroxyl groups that can both react with the glycidol and the polyglycerin portion therefore includes not only a straight chain structure, but also a branched structure.

$R^{*22}$ is expressed by $-C_3H_6O-X$, where "X" is the tetraglycerin portion.

This composition had a milky white uniform gum-like form.

Production Example 4

Synthesis of Silicone Compound No. 4

116.6 g of a methylhydrogenpolysiloxane expressed by the mean structural formula $MD_{72}D^H{}_{12}M$, 47.3 g of a vinyl tris(trimethylsiloxy)silane expressed by the mean structural formula $CH_2=CH-Si(OSiMe_3)_3$, 26.0 g of a polyglycerin monoallyl ether, 200 g of IPA, and 0.20 g of a 2.3 wt. % sodium acetate/methanol solution were placed in a reaction vessel, and heated to 60° C. while agitating under a nitrogen stream. 0.08 g of an IPA solution having 5 wt. % of chloroplatinic acid was added, and the mixture was reacted for 2 hours at 80° C. Then, 2 g of the reaction liquid was sampled and it was confirmed that the reaction rate had reached 80% through an alkali decomposition gas generation method. 10.2 g of 1-decene and 0.08 g of an IPA solution containing 5 wt. % of chloroplatinic acid were then added, and the mixture was further reacted for 3 hours at 80° C. The reaction liquid was sampled again and confirmed, revealing that the reaction was complete. The reaction liquid was heated under reduced pressure so as to distil off low-boiling components, thereby obtaining a composition containing a novel polyglycerin-modified silicone having an alkyl group and a siloxane dendron structure expressed by the mean structural formula $MD_{72}D^{R*11}{}_3D^{R*31}{}_6D^{R*22}{}_3M$ (silicone compound No. 4).

In this formula, $R^{*22}$ and $R^{*31}$ are the same as described above, and $R^{*11}=-C_{10}H_{21}$.

This composition was a somewhat brown-tinted grayish white gum-like form.

Production Example 5

Synthesis of Silicone Compound No. 5

96.3 g of a methylhydrogenpolysiloxane expressed by the mean structural formula $MD_{400}D^H{}_{10}M$, 4.0 g of a vinyl tris(trimethylsiloxy)silane expressed by the mean structural formula $CH_2=CH-Si(OSiMe_3)_3$, 7.3 g of a polyglycerin monoallyl ether, 150 g of IPA, and 0.16 g of a 2.3 wt. % sodium acetate/methanol solution were placed in a reaction vessel, and heated to 75° C. while agitating under a nitrogen stream. 0.06 g of an IPA solution having 5 wt. % of chloroplatinic acid was added, and the mixture was reacted for 2 hours at 80° C. Then, 2 g of the reaction liquid was sampled and it was confirmed that the reaction rate had reached 85% through an alkali decomposition gas generation method. 1.2 g of 1-decene and 0.06 g of an IPA solution containing 5 wt. % of chloroplatinic acid were then added, and the mixture was further reacted for 3 hours at 80° C. The reaction liquid was sampled again and confirmed, revealing that the reaction was complete.

Here, the reaction liquid was diluted by adding and blending 105.5 g of a dimethylpolysiloxane (2 cst, 25° C.). This was then heated under reduced pressure so as to distil off low-boiling components other than the diluent, thereby obtaining a mixture comprising a composition containing a novel polyglycerin-modified silicone having an alkyl group and a siloxane dendron structure expressed by the mean structural formula $MD_{400}D^{R*11}{}_2D^{R*31}{}_3D^{R*22}{}_5M$ (silicone compound No. 5) and a dimethylpolysiloxane (2 cst, 25° C.; diluent). Moreover, the silicone composition:diluent ratio was 1:1.

In this formula, $R^{*11}$, $R^{*22}$ and $R^{*31}$ are the same as described above.

This mixture was a uniform milky white color, and was a gum-like form despite being diluted to a concentration of 50%.

Production Example 6

Synthesis of Silicone Compound No. 6

158.4 g of a methylhydrogenpolysiloxane expressed by the mean structural formula $MD_{360}D^H{}_{18}M$, 28.5 g of a vinyl tris(trimethylsiloxy)silane expressed by the mean structural formula $CH_2=CH-Si(OSiMe_3)_3$, 13.1 g of a polyglycerin monoallyl ether, 200 g of IPA, and 0.20 g of a 2.3 wt. % sodium acetate/methanol solution were placed in a reaction vessel, and heated to 70° C. while agitating under a nitrogen stream. 0.15 g of an IPA solution having 5 wt. % of chloroplatinic acid was added, and the mixture was reacted for 4 hours at 80° C. Then, 2 g of the reaction liquid was sampled and it was confirmed that the reaction was complete through an alkali decomposition gas generation method.

Here, the reaction liquid was diluted by adding and blending 190.0 g of a dimethylpolysiloxane (2 cst, 25° C.). This was then heated under reduced pressure so as to distil off low-boiling components other than the diluent, thereby obtaining a mixture comprising a composition containing a novel polyglycerin-modified silicone having a siloxane dendron structure expressed by the mean structural formula $MD_{360}D^{R*31}{}_{13}D^{R*22}{}_5M$ (silicone compound No. 6) and a dimethylpolysiloxane (2 cst, 25° C.; diluent). Moreover, the silicone composition:diluent ratio was 1:1.

In this formula, $R^{*22}$ and $R^{*31}$ are the same as described above.

This mixture was a uniform milky white color, and was a gum-like form despite being diluted to a concentration of 50%.

Production Example 7

Synthesis of Silicone Compound No. 7

165.6 g of a methylhydrogenpolysiloxane expressed by the mean structural formula $MD_{360}D^H{}_{18}M$, 13.8 g of a vinyl tris(trimethylsiloxy)silane expressed by the mean structural formula $CH_2=CH-Si(OSiMe_3)_3$, 13.7 g of a polyglycerin monoallyl ether, 200 g of IPA, and 0.20 g of a 2.3 wt. % sodium acetate/methanol solution were placed in a reaction vessel, and heated to 70° C. while agitating under a nitrogen stream. 0.06 g of an IPA solution having 5 wt. % of chloroplatinic acid was added, and the mixture was reacted for 1 hour at 80° C. Then, 2 g of the reaction liquid was sampled and it was confirmed that the reaction rate had reached 65% through an alkali decomposition gas generation method. 7.0 g of 1-decene and 0.06 g of an IPA solution containing 5 wt. % of chloroplatinic acid were then added, and the mixture was further reacted for 3 hours at 80° C. The reaction liquid was sampled again and confirmed, revealing that the reaction was complete.

Here, the reaction liquid was diluted by adding and blending 190.0 g of a dimethylpolysiloxane (2 cst, 25° C.). This was then heated under reduced pressure so as to distil off low-boiling components other than the diluent, thereby obtaining a mixture comprising a composition containing a novel polyglycerin-modified silicone having an alkyl group and a siloxane dendron structure expressed by the mean structural formula $MD_{360}D^{R*11}{}_7D^{R*31}{}_6D^{R*22}{}_5M$ (silicone compound No. 7) and a dimethylpolysiloxane (2 cst, 25° C.; diluent). Moreover, the silicone composition:diluent ratio was 1:1.

In this formula, $R^{*22}$ and $R^{*31}$ are the same as described above, and $R^{*11}=-C_{10}H_{21}$.

This mixture was a somewhat brown-tinted uniform milky white color, and was a gum-like form despite being diluted to a concentration of 50%.

Production Example 8

Synthesis of Silicone Compound No. 8

151.3 g of a methylhydrogenpolysiloxane expressed by the mean structural formula $MD_{150}D^H{}_{10}M$, 26.7 g of a vinyl tris(trimethylsiloxy)silane expressed by the mean structural formula $CH_2=CH-Si(OSiMe_3)_3$, 11.8 g of a polyglycerin monoallyl ether, 10.4 g of diglycerin monoallyl ether, and 200 g of IPA were placed in a reaction vessel, and heated to 60° C. while agitating under a nitrogen stream. 0.125 g of an IPA solution of a platinum-1,3-divinyl-1,1,3,3-tetramethyl-disiloxane complex (Pt concentration: 4.5 wt. %) was added and the mixture was reacted for 5.5 hours at 80° C. Then, 2 g of the reaction liquid was sampled and it was confirmed that the reaction was complete through an alkali decomposition gas generation method. The reaction liquid was heated under reduced pressure so as to distil off low-boiling components, thereby obtaining a composition containing a novel polyglycerin-modified silicone having a siloxane dendron structure expressed by the mean structural formula $MD_{150}D^{R*31}{}_5D^{R*22}{}_2D^{R*23}{}_3M$ (silicone compound No. 8).

In this formula, $R^{*22}$ and $R^{*31}$ are the same as described above.

$R^{*23}=-C_3H_6O-X$, and X is the diglycerin moiety.

This composition was a uniform milky white, extremely viscous liquid.

Production Example 9

Synthesis of Silicone Compound No. 9

105.5 g of a methylhydrogenpolysiloxane expressed by the mean structural formula $MD_{72}D^H{}_{12}M$, 64.0 g of a vinyl tris(trimethylsiloxy)silane expressed by the mean structural formula $CH_2=CH-Si(OSiMe_3)_3$, 30.6 g of a polyglyceryl eugenol, and 190 g of IPA were placed in a reaction vessel, and heated to 60° C. while agitating under a nitrogen stream. 0.117 g of an IPA solution of a platinum-1,3-divinyl-1,1,3,3-tetramethyldisiloxane complex (Pt concentration: 4.5 wt. %) was added and the mixture was reacted for 9 hours at 80° C. Then, 2 g of the reaction liquid was sampled and it was confirmed that the reaction was complete through an alkali decomposition gas generation method. The reaction liquid was heated under reduced pressure so as to distil off low-boiling components, thereby obtaining a composition containing a novel polyglycerin-modified silicone having a siloxane dendron structure expressed by the mean structural formula $MD_{72}D^{R*31}{}_9D^{R*24}{}_3M$ (silicone compound No. 9). This composition was a semi-transparent pale yellow raw rubber.

In this formula, $R^{*31}$ is the same as described above.

Moreover, the polyglyceryl eugenol was synthesized by ring-opening polymerizing 4 molar equivalents of glycidol with 1 mole of eugenol, and had a structure in which an average of 4 moles of glycerin were added. The polyglycerin portion can contain not only a straight chain structure, but also a branched structure.

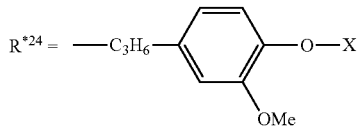

X is a tetraglycerin moiety

Production Example 10

Synthesis of Silicone Compound No. 10

112.8 g of a methylhydrogenpolysiloxane expressed by the mean structural formula $MD_{72}D^H{}_{12}M$, 45.4 g of a vinyl tris(trimethylsiloxy)silane expressed by the mean structural formula $CH_2=CH-Si(OSiMe_3)_3$, 32.5 g of a polyglyceryl eugenol, and 195 g of IPA were placed in a reaction vessel, and heated to 60° C. while agitating under a nitrogen stream. 0.067 g of an IPA solution of a platinum-1,3-divinyl-1,1,3,3-tetramethyldisiloxane complex (Pt concentration: 4.5 wt. %) was added and the mixture was reacted for 1 hour at 80° C. Then, 2 g of the reaction liquid was sampled and it was confirmed that the reaction rate had reached 80% through an alkali decomposition gas generation method. 9.9 g of 1-decene and 0.050 g of the platinum catalyst were added and reacted for 6 hours at 80° C., after which the reaction liquid was again sampled and it was confirmed that the reaction was complete. The reaction liquid was heated under reduced pressure so as to distil off low-boiling components, thereby obtaining a composition containing a novel polyglycerin-modified silicone having an alkyl group and a siloxane dendron structure expressed by the mean structural formula $MD_{72}D^{R*11}{}_3D^{R*31}{}_6D^{R*24}{}_3M$ (silicone compound No. 10).

In this formula, $R^{*31}$ and $R^{*24}$ are the same as described above, and $R^{*11}$=—$C_{10}H_{21}$.

This composition was a semi-transparent tan color raw rubber.

Production Example 11

Synthesis of Silicone Compound No. 11

155.3 g of a methylhydrogenpolysiloxane expressed by the mean structural formula $MD_{360}D^H{}_{18}M$, 28.0 g of a vinyl tris(trimethylsiloxy)silane expressed by the mean structural formula $CH_2$=CH—$Si(OSiMe_3)_3$, 16.7 g of a polyglyceryl eugenol, 200 g of IPA, and 0.20 g of a 2.3 wt. % sodium acetate/methanol solution were placed in a reaction vessel, and heated to 70° C. while agitating under a nitrogen stream. 0.12 g of an IPA solution having 5 wt. % of chloroplatinic acid was added, and the mixture was reacted for 6 hours at 80° C. Then, 2 g of the reaction liquid was sampled and it was confirmed that the reaction was complete through an alkali decomposition gas generation method.

Here, the reaction liquid was diluted by adding and blending 190.0 g of a dimethylpolysiloxane (2 cst, 25° C.). This was then heated under reduced pressure so as to distil off low-boiling components other than the diluent, thereby obtaining a mixture comprising a composition containing a novel polyglycerin-modified silicone having a siloxane dendron structure expressed by the mean structural formula $MD_{360}D^{R*31}{}_{13}D^{R*24}{}_5M$ (silicone compound No. 11) and a dimethylpolysiloxane (2 cst, 25° C.; diluent). Moreover, the silicone composition:diluent ratio was 1:1. In this formula, $R^{*24}$ and $R^{*31}$ are the same as described above.

This mixture was semi-transparent and pale yellow-white in color, and was a raw rubber despite being diluted to a concentration of 50%.

Production Example 12

Synthesis of Silicone Compound No. 12

162.3 g of a methylhydrogenpolysiloxane expressed by the mean structural formula $MD_{360}D^H{}_{18}M$, 13.5 g of a vinyl tris(trimethylsiloxy)silane expressed by the mean structural formula $CH_2$=CH—$Si(OSiMe_3)_3$, 17.4 g of a polyglyceryl eugenol, 200 g of IPA, and 0.20 g of a 2.3 wt. % sodium acetate/methanol solution were placed in a reaction vessel, and heated to 70° C. while agitating under a nitrogen stream. 0.06 g of an IPA solution having 5 wt. % of chloroplatinic acid was added, and the mixture was reacted for 1 hour at 80° C. Then, 2 g of the reaction liquid was sampled and it was confirmed that the reaction rate had reached 65% through an alkali decomposition gas generation method. 6.8 g of 1-decene and 0.06 g of an IPA solution containing 5 wt. % of chloroplatinic acid were then added, and the mixture was further reacted for 4 hours at 80° C. The reaction liquid was sampled again and confirmed, revealing that the reaction was complete.

Here, the reaction liquid was diluted by adding and blending 190.0 g of a dimethylpolysiloxane (2 cst, 25° C.). This was then heated under reduced pressure so as to distil off low-boiling components other than the diluent, thereby obtaining a mixture comprising a composition containing a novel polyglycerin-modified silicone having an alkyl group and a siloxane dendron structure expressed by the mean structural formula $MD_{360}D^{R*11}{}_7D^{R*31}{}_6D^{R*24}{}_5M$ (silicone compound No. 12) and a dimethylpolysiloxane (2 cst, 25° C.; diluent). Moreover, the silicone composition:diluent ratio was 1:1.

In this formula, $R^{*24}$ and $R^{*31}$ are the same as described above, and $R^{*11}$=—$C_{10}H_{21}$.

This mixture was semi-transparent and off-white in color, and was a raw rubber despite being diluted to a concentration of 50%.

Comparative Production Example 1

Comparative Silicone Compound RE1

89.9 g of a methylhydrogenpolysiloxane expressed by the mean structural formula $MD_{63}D^H{}_{22}M$, 36.4 g of an allyl polyether expressed by the mean structural formula $CH_2$=CH—$CH_2$—$O(C_2H_4O)_{10}H$, 73.7 g of 1-hexadecene, and 60 g of toluene were placed in a reaction vessel, and heated to 40° C. while agitating under a nitrogen stream. 0.06 g of an IPA solution of a platinum-1,3-divinyl-1,1,3,3-tetramethyldisiloxane complex (Pt concentration: 4.5 wt. %) was added and the mixture was reacted for 2.5 hours at 80 to 110° C. Then, 2 g of the reaction liquid was sampled and it was confirmed that the reaction was complete through an alkali decomposition gas generation method. The reaction liquid was heated under reduced pressure so as to distil off low-boiling components, thereby obtaining a composition containing an alkyl/polyether-co-modified silicone expressed by the mean structural formula $MD_{63}D^{R*12}{}_{18}D^{R*25}{}_4M$ (silicone compound RE1).

In this formula, $R^{*12}$=—$C_{16}H_{33}$.
$R^{*25}$=—$C_3H_6O(C_2H_4O)_{10}H$

This composition was a semi-transparent tan colored uniform liquid.

Comparative Production Example 2

Comparative Silicone Compound RE2

206.1 g of a methylhydrogenpolysiloxane expressed by the mean structural formula $MD_{400}D^H{}_{10}M$, 105.6 g of an allyl polyether expressed by the mean structural formula $CH_2$=CH—$CH_2$—$O(C_2H_4O)_{19}(C_3H_6O)_{19}H$, 90 g of IPA, 0.12 g of natural vitamin E, and 0.46 g of a 2.0 wt. % sodium acetate/methanol solution were placed in a reaction vessel, and heated to 50° C. while agitating under a nitrogen stream. 0.04 g of an IPA solution containing 5 wt. % of chloroplatinic acid was added, and the mixture was reacted for 5 hours at 90° C. The reaction liquid was sampled, it was confirmed that the concentration of residual Si—H groups was within specification, and the reaction was terminated.

Here, the reaction liquid was diluted by adding and blending 300.0 g of a dimethylpolysiloxane (2 cst, 25° C.). This was then heated under reduced pressure so as to distil off low-boiling components other than the diluent, thereby obtaining a mixture comprising a composition containing a polyether-modified silicone expressed by the mean structural formula $MD_{400}D^{R*26}{}_{10}M$ (silicone compound RE2) and a dimethylpolysiloxane (2 cst, 25° C.; diluent). Moreover, the silicone composition:diluent ratio was 1:1.

In this formula, $R^{*26}$=—$C_3H_6O(C_2H_4O)_{19}(C_3H_6O)_{19}H$.

This mixture was a nearly colorless transparent viscous liquid.

Comparative Production Example 3

Comparative Silicone Compound RE3

212.5 g of a methylhydrogenpolysiloxane expressed by the mean structural formula $MD_{406}D^H{}_4M$, 4.9 g of a glycerin monoallyl ether expressed by the structural formula $CH_2=CH-CH_2-OCH_2CH(OH)CH_2OH$, and 90 g of IPA were placed in a reaction vessel, and heated to 70° C. while agitating under a nitrogen stream. 0.053 g of an IPA solution of a platinum-1,3-divinyl-1,1,3,3-tetramethyldisiloxane complex (Pt concentration: 4.5 wt. %) was added and the mixture was reacted for 3 hours at 80° C. Then, 2 g of the reaction liquid was sampled and it was confirmed that the reaction was complete through an alkali decomposition gas generation method. The reaction liquid was heated under reduced pressure so as to distil off low-boiling components, thereby obtaining a composition containing a glycerin-modified silicone expressed by the mean structural formula $MD_{406}D^{R*21}{}_4M$ (silicone compound RE3).

In this formula, $R^{21}=-C_3H_6OCH_2CH(OH)CH_2OH$

This composition was a light yellowish-brown, semi-transparent uniform viscous liquid.

Comparative Production Example 4

Comparative Silicone Compound RE4

155.9 g of a methylhydrogenpolysiloxane expressed by the mean structural formula $MD_{72}D^H{}_{12}M$, 13.0 g of a glycerin monoallyl ether expressed by the structural formula $CH_2=CH-CH_2-OCH_2CH(OH)CH_2OH$, 41.1 g of 1-decene, and 63 g of IPA were placed in a reaction vessel, and heated to 45° C. while agitating under a nitrogen stream. 0.055 g of an IPA solution of a platinum-1,3-divinyl-1,1,3,3-tetramethyldisiloxane complex (Pt concentration: 4.5 wt. %) was added and the mixture was reacted for 1 hour at 80° C. Then, 2 g of the reaction liquid was sampled and it was confirmed that the reaction was complete through an alkali decomposition gas generation method. The reaction liquid was heated under reduced pressure so as to distil off low-boiling components, thereby obtaining a composition containing an alkyl/glycerin-co-modified silicone expressed by the mean structural formula $MD_{72}D^{R*11}{}_9D^{R*21}{}_3M$ (silicone compound RE4).

In this formula, $R^{*11}=-C_{10}H_{21}$
$R^{*21}=-C_3H_6OCH_2CH(OH)CH_2OH$.

This composition was a semi-transparent tan colored liquid.

Comparative Production Example 5

Comparative Silicone Compound RE5

134.6 g of a methylhydrogenpolysiloxane expressed by the mean structural formula $MD_{72}D^H{}_{12}M$, 36.2 g of 1-decene, 29.9 g of a polyglycerin monoallyl ether, 200 g of IPA, and 0.25 g of a 2.3 wt. % sodium acetate/methanol solution were placed in a reaction vessel, and heated to 55° C. while agitating under a nitrogen stream. 0.160 g of an IPA solution having 5 wt. % of chloroplatinic acid was added, and the mixture was reacted for 7 hours at 80° C. Then, 2 g of the reaction liquid was sampled and it was confirmed that the reaction was complete through an alkali decomposition gas generation method. The reaction liquid was heated under reduced pressure so as to distil off low-boiling components, thereby obtaining a composition containing an alkyl/polyglycerin-co-modified silicone expressed by the mean structural formula $MD_{72}D^{R*11}{}_9D^{*22}{}_3M$ (silicone compound RE5).

In this formula, $R^{*11}$ is the same as described above,
$R^{*22}$ is also the same as described above, and is expressed by $-C_3H_6O-X$, where "X" is the tetraglycerin portion.

This composition had a gum-like form that was off-white throughout and was not uniform but, rather, partial phase separation (of the gum-like tan colored phase) had occurred.

Comparative Production Example 6

Comparative Silicone Compound RE6

111.6 g of a methylhydrogenpolysiloxane expressed by the mean structural formula $MD_{61}D^H{}_{15}M$ was placed in a reaction vessel. Then a mixture comprising 30.9 g of a single-terminal vinyl-modified dimethylpolysiloxane expressed by the structural formula $CH_2=CHSiMe_2(OSiMe_2)_6OSiMe_3$ and 0.10 g of a toluene solution of a platinum-1,3-divinyl-1,1,3,3-tetramethyldisiloxane complex (Pt concentration: 0.5 wt. %) was added dropwise, and the mixture was agitated at room temperature, thereby obtaining a linear siloxane branched-type polysiloxane intermediate.

7.0 g of triglycerin monoallyl ether, 50.4 g of 1-dodecene, 100 g of IPA, and 0.40 g of an IPA solution of a platinum-1,3-divinyl-1,1,3,3-tetramethyldisiloxane complex (Pt concentration: 0.5 wt. %) were placed in another reaction vessel, and while agitating under a nitrogen stream, the mixture was added dropwise to the previously synthesized linear siloxane branched-type polysiloxane in a refluxing solvent. After the adding was completed, heating and agitating was continued for 3 hours. Then, 2 g of the reaction liquid was sampled and it was confirmed that the reaction was complete through an alkali decomposition gas generation method. The reaction liquid was heated under reduced pressure to remove low-boiling components by distillation. The reaction liquid was filtered, thereby obtaining a composition containing an alkyl/linear siloxane/polyglycerin-co-modified silicone expressed by the mean structural formula $MD_{61}D^{R*13}{}_{12}D^{R*41}{}_2D^{R*27}{}_1M$ (silicone compound RE6).

In this formula, $R^{*13}=-C_{12}H_{25}$
$R^{*41}=-C_2H_4SiMe_2(OSiMe_2)_6OSiMe_3$
$R^{*27}=-C_3H_6O-X$, where "X" is the triglycerin portion.

This composition was a semi-transparent nearly colorless uniform liquid.

Comparative Production Example 7

Comparative Silicone Compound RE7

187.0 g of a flaked α-olefin (having 30 or more carbons on average) was placed in a reaction vessel and melted by heating to 80° C. while agitating under a nitrogen stream. 0.8 mg of a solution of a ligand of a platinum-1,3-divinyl-1,1,3,3-tetramethyldisiloxane complex (Pt concentration 22 wt. %) was added, and 13.0 g of a methylhydrogenpolysiloxane expressed by the mean structural formula $MD^H{}_{15}M$ was added dropwise over a period of 30 minutes while agitating. The reaction temperature was controlled to 120° C., and a reaction was continued for 3 hours. The reaction liquid was sampled, it was confirmed that the concentration of residual Si—H groups was within specification, and the reaction was terminated. In this way a composition containing an alkyl-modified silicone wax expressed by the mean structural formula $MD^{R*14}{}_{15}M$ (silicone compound RE7) was obtained.

In the formula, $R^{*14}$ is a long chain alkyl group no shorter than $-C_{30}H_{61}$.

Comparative Production Example 8

Comparative Silicone Compound RE8

(Amino Acid Derivative-Modified Silicone)

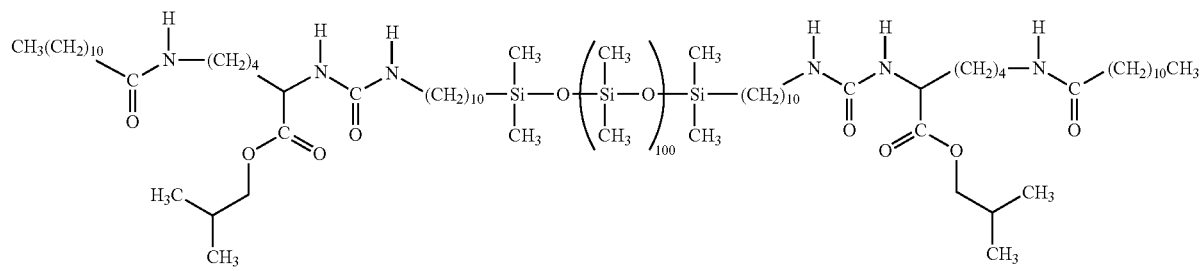

(Produced According to the Methods Described in Patent Document 8 and Production Example 1)

(1) 20.1 g of Nε-lauroyl-L-lysine was suspended in 205 mL of ethanol. The reaction liquid was cooled with ice, injected with dried hydrogen chloride gas until saturated and then agitated for 6 hours. Next, the ethanol was distilled off, 250 mL of diisobutyl ether was added, the reaction liquid was subjected to vacuum filtration, and 300 mL of purified water was then added. A solution obtained by dissolving 55 g of morpholine in 70 mL of purified water was added gradually to this solution while agitating, and a precipitated white powder was filtered off. The obtained white powder was recrystallized using n-hexane, thereby obtaining 20.1 g of an isobutyl ester of Nε-lauroyl-L-lysine.

(2) 150 g of purified water was added to 45.5 g of sodium azide, cooled in iced water, and then agitated so as to obtain a uniform solution. To this, a solution obtained by blending 101.4 g of 10-undecenoyl chloride with 150 mL of acetone was added dropwise in small portions so that the temperature of the solution remained within a range of 10 to 15° C. Once this addition was complete, the solution was agitated for 1 hour at a temperature of approximately 12° C. The solution was then transferred to a separatory funnel and separated into an aqueous layer and an organic layer. The organic layer was added gradually to 500 mL of toluene held at a temperature of 60° C. and then agitated for 3 hours at a temperature of approximately 50 to 60° C. After distilling off the toluene, 73.2 g of 10-undecenoyl isocyanate was obtained by distillation under reduced pressure.

(3) 92.6 g of a methylhydrogenpolysiloxane expressed by the mean structural formula $M^H D_{100} M^H$ and 7.4 g of 10-undecenoyl isocyanate were added to 100 g of toluene and heated to 85° C., after which 0.33 g of a toluene solution of a platinum-1,3-divinyl-1,1,3,3-tetramethyldisiloxane (Pt concentration 0.3 wt. %) was added and agitated for 3 hours. After distilling off the toluene and excess isocyanate compound under reduced pressure, 1000 g of fresh toluene and 10.5 g of an isobutyl ester of Nε-lauroyl-L-lysine were added and agitated for 6 hours at 90° C. After distilling off the toluene, the obtained transparent rubbery solid was dissolved by heating in 1000 g of hexane and then hot filtered. A solid was then obtained by distilling the hexane off from the filtrate. The obtained solid was then finely ground and subjected to vacuum filtration while being thoroughly washed with hexane at 25° C., and 20.3 g of a powdered lysine derivative-modified silicone expressed by the formula below (a modified silicone by a derivative of an isobutyl ester of Nε-lauroyl-L-lysine) was obtained by drying under reduced pressure.

The average composition formulas of Silicone Compound No. 1 to Silicone Compound No. 12 according to the present invention, and Comparative Silicone Compound RE1 to Comparative Silicone Compound RE7 according to the comparative examples, which are synthesized according to the methods described above, are as follows. Moreover, the structure of "Comparative Silicone Compound RE8" is as described in the previous paragraph.

TABLE 1

| Silicone compound | Average composition formula | Properties |
|---|---|---|
| Silicone compound No. 1 | $MD_{400}D^{R*31}{}_5 D^{R*21}{}_5 M$ | Light yellow, semi-transparent uniform viscous liquid |
| Silicone compound No. 2 | $MD_{400}D^{R*11}{}_2 D^{R*31}{}_3 D^{R*21}{}_5 M$ | Light yellowish-brown, semi-transparent uniform liquid |
| Silicone compound No. 3 | $MD_{72}D^{R*31}{}_9 D^{R*22}{}_3 M$ | Milky white uniform gum-like form |
| Silicone compound No. 4 | $MD_{72}D^{R*11}{}_3 D^{R*31}{}_6 D^{R*22}{}_3 M$ | Somewhat brown-tinted grayish white gum |
| Mixture containing silicone compound No. 5 | $MD_{400}D^{R*11}{}_2 D^{R*31}{}_3 D^{R*22}{}_5 M$ *Diluted with dimethylpolysiloxane to a concentration of 50% | Uniform milky white color (gum) |
| Mixture containing silicone compound No. 6 | $MD_{360}D^{R*31}{}_{13} D^{R*22}{}_5 M$ *Diluted with dimethylpolysiloxane to a concentration of 50% | Uniform milky white color (gum) |
| Mixture containing silicone compound No. 7 | $MD_{360}D^{R*11}{}_7 D^{R*31}{}_6 D^{R*22}{}_5 M$ *Diluted with dimethylpolysiloxane to a concentration of 50% | Uniform milky white color (gum) |
| Silicone compound No. 8 | $MD_{150}D^{R*31}{}_5 D^{R*22}{}_2 D^{R*23}{}_3 M$ | Uniform milky white, extremely viscous liquid |

TABLE 1-continued

| Silicone compound | Average composition formula | Properties |
|---|---|---|
| Silicone compound No. 9 | $MD_{72}D^{R*31}{}_9D^{R*24}{}_3M$ | Semi-transparent pale yellow raw rubber |
| Silicone compound No. 10 | $MD_{72}D^{R*11}{}_3D^{R*31}{}_6D^{R*24}{}_3M$ | Semi-transparent tan color raw rubber |
| Mixture containing silicone compound No. 11 | $MD_{360}D^{R*31}{}_{13}D^{R*24}{}_5M$ *Diluted with dimethylpolysiloxane to a concentration of 50% | Semi-transparent, pale yellow-white in color (raw rubber). |
| Mixture containing silicone compound No. 12 | $MD_{360}D^{R*11}{}_7D^{R*31}{}_6D^{R*24}{}_5M$ | Semi-transparent, off-white (raw rubber) |
| Silicone compound No. 14 | $MD_{43}D^{R*31}{}_5D^{R*24}{}_2M$ | Tan, nearly transparent uniform liquid |

Hydrophilic group: $R^{*2}$
$R^{*21}$=—$C_3H_6OCH_2CH(OH)CH_2OH$
$R^{*22}$ is a hydrophilic group expressed by —$C_3H_6O$—X (where "X" is the tetraglycerin portion)
$R^{*23}$=—$C_3H_6O$—X, where "X" is the diglycerin portion.

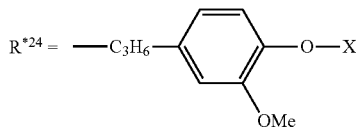

X is a tetraglycerin moiety
$R^{*25}$=—$C_3H_6O(C_2H_4O)_{10}H$
$R^{*26}$=—$C_3H_6O(C_2H_4O)_{19}(C_3H_6O)_{19}H$
$R^{*27}$ is a hydrophilic group expressed by —$C_3H_6O$—X (where "X" is the triglycerin portion)
Group having a siloxane dendron structure: $R^{*3}$
$R^{*31}$=—$C_2H_4Si(OSiMe_3)_3$
Group having a linear polysiloxane structure: $R^{*4}$
$R^{*41}$=—$C_2H_4SiMe_2(OSiMe_2)_6OSiMe_3$

TABLE 2

| | | |
|---|---|---|
| Comparative Silicone compound RE1 | $MD_{63}D^{R*12}{}_{18}D^{R*25}{}_4M$ | Light yellow, transparent uniform liquid |
| Comparative Mixture containing silicone compound RE2 | $MD_{400}D^{R*26}{}_{10}M$ *Diluted with dimethylpolysiloxane to a concentration of 50% | Almost colorless transparent viscous liquid |
| Comparative silicone compound RE3 | $MD_{406}D^{R*21}{}_4M$ | Light yellowish-brown, semi-transparent uniform viscous liquid |
| Comparative silicone compound RE4 | $MD_{72}DR^{*11}{}_9DR^{*21}{}_3M$ | Tan, semi-transparent liquid |
| Comparative silicone compound RE5 | $MD_{72}R^{*11}{}_9D^{R*22}{}_3M$ | Off-white gum form (not uniform but, rather, partially phase separated) |
| Comparative Silicone compound RE6 | $MD_{61}D^{R*13}{}_{12}D^{R*41}{}_2D^{R*27}{}_1M$ | Nearly colorless, semi-transparent uniform liquid |
| Comparative Silicone compound RE7 | $MD^{R*14}{}_{15}M$ | Silicone wax |

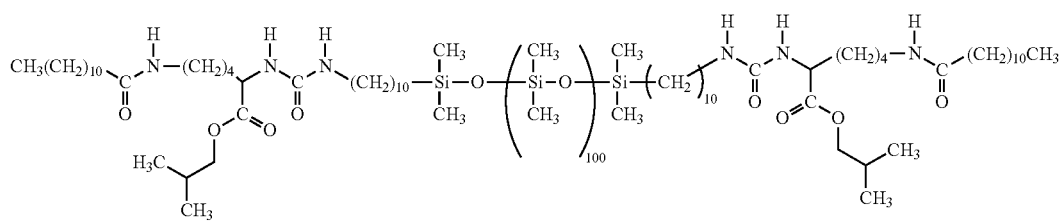

In the tables, the structures and types of the functional groups are as follows.
Long chain alkyl group: $R^{*1}$
$R^{*11}$=—$C_{10}H_{21}$
$R^{*12}$=—$C_{16}H_{33}$
$R^{*13}$=—$C_{12}H_{25}$
$R^{*14}$ is a long chain alkyl group no shorter than —$C_{30}H_{61}$.

Practical Examples 1 to 6 and Comparative Examples 1 to 6

Confirmation of Thickening Effect for Oil Agent Systems

Using the formulations shown in tables 2 to 12, mixtures of oil agent systems and the modified silicone compounds (obtained as compositions and then, depending on the production method, diluted) were prepared according to the procedures described below.

[Preparation and Testing Procedures]

1. An oil agent system and a modified silicone compound described in the production examples above were placed in a vessel and uniformly blended and dispersed by heating to 80° C. (Moreover, in comparative example 3, comparative silicone compounds RE1 and RE4 were used in combination at a blending ratio of 1:1)

2. The mixture was allowed to return to room temperature and allowed to stand for 1 week, after which the appearance and properties of the mixture were recorded.

Evaluation

1. Appearance (miscibility):

○: Uniform appearance maintained.

Δ: Almost uniform, but slight precipitation observed.

x: Non-uniform, separation occurred.

2. Properties (thickening effect): Recorded in order of increasing viscosity as "low viscosity", "viscous", "syrup-like", "gum-like" and "rubber-like". Here, gum-like means having properties close to those of a highly polymerized silicone gum. Moreover, cases in which the mixture became completely solid, such as a wax, were recorded as x.

[Formulations and Evaluation Results]

Formulations and evaluation results relating to thickening/gelling are shown in tables 2 to 12.

Moreover, the "concentrations" shown in the tables denote wt. % of modified silicone compounds.

Moreover, in the tables below, the oil agent types have been abbreviated as described below for reasons of space. In addition, in cases where a mixed oil agent obtained by mixing two or more types of oil agent at specific proportions was used, the oil agent types were demarcated by "/" and the proportions are given in brackets thereafter. For example, an oil agent system obtained by mixing oil agent A and oil agent B at proportions of 70:30 is expressed as "A/B (70:30)".

2 cst: dimethylpolysiloxane (2 cst)
20 cst: dimethylpolysiloxane (20 cst)
SH 556: phenyl trimethicone
SS-3408: caprylyl methicone
CEH: cetyl 2-ethylhexanoate
IOTG: glyceryl tri(2-ethylhexanoate)
IP: isoparaffin
K-230: liquid paraffin

TABLE 3

Practical example 1: Thickening effect of silicone compound No. 5

| oil agent system | Concentration 10 wt. % | | Concentration 20 wt. % | | Concentration 30 wt. % | |
|---|---|---|---|---|---|---|
| | Miscibility | Properties | Miscibility | Properties | Miscibility | Properties |
| 2 cst | ○ | Viscous | ○ | Gum-like | ○ | Gum-like |
| 20 cst | ○ | Syrup-like | ○ | Gum-like | ○ | Rubber-like |
| SH 556 | ○ | Viscous | ○ | Gum-like | ○ | Gum-like |
| SS-3408 | ○ | Viscous | ○ | Gum-like | ○ | Gum-like |
| 2 cst/CEH (50/50) | ○ | Viscous | ○ | Syrup-like | ○ | Gum-like |
| 2 cst/IOTG (50/50) | ○ | Viscous | ○ | Syrup-like | ○ | Gum-like |
| 2 cst/IP (50/50) | ○ | Viscous | ○ | Gum-like | ○ | Gum-like |
| 2 cst/K-230 (50/50) | X | — | ○ | Gum-like | ○ | Rubber-like |

TABLE 4

Practical example 2: Thickening effect of silicone compound No. 6

| oil agent system | Concentration 10 wt. % | | Concentration 20 wt. % | | Concentration 30 wt. % | |
|---|---|---|---|---|---|---|
| | Miscibility | Properties | Miscibility | Properties | Miscibility | Properties |
| 2 cst | ○ | Viscous | ○ | Gum-like | ○ | Gum-like |
| 20 cst | ○ | Syrup-like | ○ | Gum-like | ○ | Rubber-like |
| SH 556 | ○ | Viscous | ○ | Gum-like | ○ | Gum-like |
| SS-3408 | ○ | Viscous | ○ | Gum-like | ○ | Gum-like |
| 2 cst/CEH (50/50) | ○ | Viscous | ○ | Syrup-like | ○ | Gum-like |
| 2 cst/IOTG (50/50) | ○ | Viscous | ○ | Syrup-like | ○ | Gum-like |
| 2 cst/IP (50/50) | ○ | Viscous | ○ | Gum-like | ○ | Gum-like |
| 2 cst/K-230 (50/50) | ○ | Syrup-like | ○ | Gum-like | ○ | Rubber-like |

TABLE 5

Practical example 3: Thickening effect of silicone compound No. 7

| oil agent system | Concentration 10 wt. % | | Concentration 20 wt. % | | Concentration 30 wt. % | |
|---|---|---|---|---|---|---|
| | Miscibility | Properties | Miscibility | Properties | Miscibility | Properties |
| 2 cst | ○ | Viscous | ○ | Gum-like | ○ | Gum-like |
| 20 cst | ○ | Syrup-like | ○ | Gum-like | ○ | Rubber-like |
| SH 556 | ○ | Viscous | ○ | Gum-like | ○ | Gum-like |
| SS-3408 | ○ | Syrup-like | ○ | Gum-like | ○ | Gum-like |
| 2 cst/CEH (50/50) | ○ | Syrup-like | ○ | Gum-like | ○ | Gum-like |
| 2 cst/IOTG (50/50) | ○ | Syrup-like | ○ | Gum-like | ○ | Rubber-like |
| 2 cst/IP (50/50) | ○ | Viscous | ○ | Gum-like | ○ | Gum-like |
| 2 cst/K-230 (50/50) | ○ | Syrup-like | ○ | Gum-like | ○ | Rubber-like |

TABLE 6

Practical example 4: Thickening effect of silicone compound No. 11

| oil agent system | Concentration 10 wt. % | | Concentration 20 wt. % | | Concentration 30 wt. % | |
|---|---|---|---|---|---|---|
| | Miscibility | Properties | Miscibility | Properties | Miscibility | Properties |
| 2 cst | ○ | Syrup-like | ○ | Gum-like | ○ | Rubber-like |
| 20 cst | ○ | Gum-like | ○ | Rubber-like | ○ | Rubber-like |
| SH 556 | ○ | Viscous | ○ | Gum-like | ○ | Rubber-like |
| SS-3408 | ○ | Viscous | ○ | Gum-like | ○ | Rubber-like |
| 2 cst/CEH (50/50) | ○ | Syrup-like | ○ | Gum-like | ○ | Rubber-like |
| 2 cst/IOTG (50/50) | ○ | Syrup-like | ○ | Gum-like | ○ | Rubber-like |
| 2 cst/IP (50/50) | ○ | Syrup-like | ○ | Gum-like | ○ | Rubber-like |
| 2 cst/K-230 (50/50) | ○ | Gum-like | ○ | Rubber-like | ○ | Rubber-like |

TABLE 7

Practical example 5: Thickening effect of silicone compound No. 12

| oil agent system | Concentration 10 wt. % | | Concentration 20 wt. % | | Concentration 30 wt. % | |
|---|---|---|---|---|---|---|
| | Miscibility | Properties | Miscibility | Properties | Miscibility | Properties |
| 2 cst | ○ | Syrup-like | ○ | Gum-like | ○ | Rubber-like |
| 20 cst | ○ | Gum-like | ○ | Rubber-like | ○ | Rubber-like |
| SH 556 | ○ | Syrup-like | ○ | Gum-like | ○ | Rubber-like |
| SS-3408 | ○ | Syrup-like | ○ | Gum-like | ○ | Rubber-like |
| 2 cst/CEH (50/50) | ○ | Syrup-like | ○ | Gum-like | ○ | Rubber-like |
| 2 cst/IOTG (50/50) | ○ | Gum-like | ○ | Gum-like | ○ | Rubber-like |
| 2 cst/IP (50/50) | ○ | Syrup-like | ○ | Gum-like | ○ | Rubber-like |
| 2 cst/K-230 (50/50) | ○ | Gum-like | ○ | Rubber-like | ○ | Rubber-like |

TABLE 8

Practical example 6: Thickening effect of silicone compound No. 10

| oil agent system | Concentration 10 wt. % | | Concentration 20 wt. % | | Concentration 30 wt. % | |
|---|---|---|---|---|---|---|
| | Miscibility | Properties | Miscibility | Properties | Miscibility | Properties |
| 2 cst | ○ | Low viscosity | ○ | Low viscosity | ○ | Viscous |
| 20 cst | ○ | Low viscosity | ○ | Viscous | ○ | Viscous |
| SH 556 | Δ | Low viscosity | ○ | Low viscosity | ○ | Low viscosity |
| SS-3408 | Δ | Low viscosity | ○ | Low viscosity | ○ | Low viscosity |
| 2 cst/CEH (50/50) | ○ | Low viscosity | ○ | Viscous | ○ | Viscous |
| 2 cst/IOTG (50/50) | ○ | Viscous | ○ | Viscous | ○ | Viscous |
| 2 cst/IP (50/50) | ○ | Low viscosity | ○ | Low viscosity | ○ | Viscous |
| 2 cst/K-230 (50/50) | ○ | Viscous | ○ | Viscous | ○ | Viscous |

TABLE 9

Comparative example 1: Thickening effect of comparative silicone compound RE2

| oil agent system | Concentration 10 wt. % | | Concentration 20 wt. % | | Concentration 30 wt. % | |
|---|---|---|---|---|---|---|
| | Miscibility | Properties | Miscibility | Properties | Miscibility | Properties |
| 2 cst | ○ | Low viscosity | ○ | Viscous | ○ | Viscous |
| 20 cst | X | — | ○ | Syrup-like | ○ | Syrup-like |
| SH 556 | ○ | Low viscosity | Δ | Low viscosity | Δ | Low viscosity |
| SS-3408 | ○ | Low viscosity | ○ | Viscous | ○ | Viscous |
| 2 cst/CEH (50/50) | ○ | Low viscosity | ○ | Low viscosity | ○ | Low viscosity |
| 2 cst/IOTG (50/50) | Δ | Low viscosity | Δ | Low viscosity | Δ | Low viscosity |
| 2 cst/IP (50/50) | ○ | Low viscosity | ○ | Viscous | ○ | Viscous |
| 2 cst/K-230 (50/50) | X | — | ○ | Viscous | ○ | Viscous |

TABLE 10

Comparative example 2: Thickening effect of comparative silicone compound RE6

| oil agent system | Concentration 10 wt. % | | Concentration 20 wt. % | | Concentration 30 wt. % | |
|---|---|---|---|---|---|---|
| | Miscibility | Properties | Miscibility | Properties | Miscibility | Properties |
| 2 cst | ○ | Low viscosity | ○ | Low viscosity | ○ | Low viscosity |
| 20 cst | ○ | Low viscosity | ○ | Low viscosity | ○ | Low viscosity |
| SH 556 | ○ | Low viscosity | ○ | Low viscosity | ○ | Low viscosity |
| SS-3408 | ○ | Low viscosity | ○ | Low viscosity | ○ | Low viscosity |
| 2 cst/CEH (50/50) | ○ | Low viscosity | ○ | Low viscosity | ○ | Low viscosity |
| 2 cst/IOTG (50/50) | ○ | Low viscosity | ○ | Low viscosity | ○ | Low viscosity |
| 2 cst/IP (50/50) | ○ | Low viscosity | ○ | Low viscosity | ○ | Low viscosity |
| 2 cst/K-230 (50/50) | ○ | Low viscosity | ○ | Low viscosity | ○ | Low viscosity |

TABLE 11

Comparative example 3: Thickening effect of comparative silicone compounds RE1/RE4 (used at a blending ratio of 1:1)

| oil agent system | Concentration 10 wt. % | | Concentration 20 wt. % | | Concentration 30 wt. % | |
|---|---|---|---|---|---|---|
| | Miscibility | Properties | Miscibility | Properties | Miscibility | Properties |
| 2 cst | ○ | Low viscosity | ○ | Low viscosity | ○ | Low viscosity |
| 20 cst | ○ | Low viscosity | ○ | Low viscosity | ○ | Low viscosity |
| SH 556 | ○ | Low viscosity | ○ | Low viscosity | ○ | Low viscosity |
| SS-3408 | ○ | Low viscosity | ○ | Low viscosity | ○ | Low viscosity |
| 2 cst/CEH (50/50) | ○ | Low viscosity | ○ | Low viscosity | ○ | Low viscosity |
| 2 cst/IOTG (50/50) | ○ | Low viscosity | ○ | Low viscosity | ○ | Low viscosity |
| 2 cst/IP (50/50) | ○ | Low viscosity | ○ | Low viscosity | ○ | Low viscosity |
| 2 cst/K-230 (50/50) | ○ | Low viscosity | ○ | Low viscosity | ○ | Low viscosity |

TABLE 12

Comparative example 4: Thickening effect of comparative silicone compound RE7

| oil agent system | Concentration 10 wt. % | | Concentration 20 wt. % | | Concentration 30 wt. % | |
|---|---|---|---|---|---|---|
| | Miscibility | Properties | Miscibility | Properties | Miscibility | Properties |
| 2 cst | X | — | X | — | X | — |
| 20 cst | X | — | X | — | X | — |
| SH 556 | ○ | X (solidified) | ○ | X (solidified) | ○ | X (solidified) |
| SS-3408 | ○ | X (solidified) | ○ | X (solidified) | ○ | X (solidified) |
| 2 cst/CEH (50/50) | X | — | X | — | X | — |
| 2 cst/IOTG (50/50) | X | — | X | — | X | — |
| 2 cst/IP (50/50) | ○ | X (solidified) | ○ | X (solidified) | ○ | X (solidified) |
| 2 cst/K-230 (50/50) | ○ | X (solidified) | ○ | X (solidified) | ○ | X (solidified) |

TABLE 13

Comparative example 5: Thickening effect of comparative silicone compound RE8

| oil agent system | Concentration 10 wt. % | | Concentration 20 wt. % | | Concentration 30 wt. % | |
|---|---|---|---|---|---|---|
| | Miscibility | Properties | Miscibility | Properties | Miscibility | Properties |
| 2 cst | ○ | X (solidified) | ○ | X (solidified) | ○ | X (solidified) |
| 20 cst | X | — | X | — | X | — |
| SH 556 | Δ | X (solidified) | Δ | X (solidified) | Δ | X (solidified) |
| SS-3408 | ○ | X (solidified) | ○ | X (solidified) | ○ | X (solidified) |
| 2 cst/CEH (50/50) | ○ | X (solidified) | Δ | X (solidified) | Δ | X (solidified) |
| 2 cst/IOTG (50/50) | ○ | X (solidified) | Δ | X (solidified) | Δ | X (solidified) |
| 2 cst/IP (50/50) | ○ | X (solidified) | ○ | X (solidified) | ○ | X (solidified) |
| 2 cst/K-230 (50/50) | Δ | X (solidified) | Δ | X (solidified) | Δ | X (solidified) |

Practical Examples 7 to 12 and Comparative Examples 6 and 7

Restorative Effect on Cuts on Mixture Surfaces

Modified silicone compounds that were found from the results in tables 3 to 8 to exhibit remarkable liquid oil agent form-controlling performance were tested for a cut restorative effect on the surface of a mixture having an oil agent concentration of 20 wt. %.

Test Procedure

1. Using a spatula, a cut having a length of 1 cm and a depth of 5 mm was made on the surface of the mixtures prepared as described above, and the time until the cut disappeared spontaneously and the surface was restored to a smooth state was observed and recorded.

Evaluation

1. Surface cut restorative effect

⊚⊚: Cut disappeared and surface was restored to a smooth state immediately.
⊚: Cut disappeared and surface was restored to a smooth state within 1 hour.
○: Cut disappeared and surface was restored to a smooth state within 12 hours.
x: Cut showed no signs of disappearing even after 24 hours.

The evaluation results for these practical examples and comparative examples are shown in table 13.

TABLE 14

Cut restorative effect on oil agent/-modified silicone surfaces (practical examples 7 to 11 and comparative examples 6 and 7)

| oil agent system | Practical Example 7 Silicone compound No. 5 | Practical Example 8 Silicone compound No. 6 | Practical Example 9 Silicone compound No. 7 | Practical Example 10 Silicone compound No. 11 |
|---|---|---|---|---|
| 2 cst | ⊚ | ⊚ | ⊚ | ⊚ |
| 20 cst | ⊚ | ⊚ | ⊚ | ○ |
| SH 556 | ⊚ | ⊚ | ⊚ | ⊚ |
| SS-3408 | ⊚ | ⊚ | ⊚ | ⊚ |
| 2 cst/CEH (50/50) | ⊚⊚ | ⊚⊚ | ⊚ | ⊚ |
| 2 cst/IOTG (50/50) | ⊚⊚ | ⊚⊚ | ⊚ | ⊚ |
| 2 cst/IP (50/50) | ⊚ | ⊚ | ⊚ | ⊚ |
| 2 cst/K-230 (50/50) | ⊚ | ⊚ | ⊚ | ○ |

| oil agent system | Practical Example 11 Silicone compound No. 12 | Comparative Example 6 Silicone Compound RE7 | Comparative Example 7 Silicone Compound RE8 |
|---|---|---|---|
| 2 cst | ⊚ | — (Separated) | X |
| 20 cst | ○ | — (Separated) | — (Separated) |
| SH 556 | ⊚ | X | X |
| SS-3408 | ⊚ | X | X |
| 2 cst/CEH (50/50) | ⊚ | — (Separated) | X |
| 2 cst/IOTG (50/50) | ⊚ | — (Separated) | X |
| 2 cst/IP (50/50) | ⊚ | X | X |
| 2 cst/K-230 (50/50) | ○ | X | X |

Practical Examples 12 to 15 and Comparative Examples 8 to 13

Lipsticks

Lipsticks were prepared by heating and blending the compositions (formulations) shown in tables 15 to 17 and then forming by cooling according to the procedure described below. In addition, the obtained lipsticks were evaluated according to the criteria given below using the testing procedures described below.

Preparation Procedure

A. Components 1 to 15 were heated to 50° C., mixed and uniformly melted.

B. Component 16 was added to A and uniformly blended/dispersed therewith.

C. This mixture was poured into a mold and then solidified by cooling so as to produce a rouge.

Test Procedure 1. 0.05 g of the obtained lipstick was evenly applied to a 1 cm×3 cm section of cleansed skin (back of hand). Moreover, because rouge tends to enter wrinkles of the lips and spread out from there, the back of the hand was used as the test surface instead of the lips because many wrinkles and sensory nerves are concentrated on the back of the hand and visual observation thereof is easy.

2. The following five criteria were evaluated 10 minutes (initial stage), 4 hours, 7 hours, and 9 hours after application.

"resistance to color migration", "resistance to color rub-off", and "tendency not to spread": judged visually "natural feeling on the skin with no discomfort": judged according to skin sensation at the applied part "finish": judged visually and in terms of overall satisfaction with the cosmetic effect Evaluation 1. Resistance to color migration: a white ceramic cup was pushed gently onto the applied surface, and the color migration when the cup was removed was judged.

⊚: No color migration whatsoever.
○: Slight color migration, albeit inconspicuous.
Δ: Some color migration noticeable.
x: Conspicuous color migration.

2. Resistance to color rub-off: changes in the applied color (fading, dullness and the like) were observed visually. 4, 7 and 9 hours after application, lipstick was applied in the same way as the initial application at a different site (back of the hand) close to the applied surface, and the change in color was judged by comparing with the freshly applied surface.

⊚: no change in color.
○: slight change in color, albeit inconspicuous.
Δ: Some color rub-off observed.
x: noticeable dulling of color.

3. Tendency not to spread: A film initially measuring 1 cm×3 cm was applied and the amount of expansion and spreading into surrounding areas over time was visually observed.

⊚: No spread of color or oil

○: Slight, insignificant spread of color or oil
Δ: Some spreading of color or oil
x: noticeable spreading of color and oil 4. Natural feeling on the skin with no discomfort: judged comprehensively according to the skin sensation at the applied part and the tactile sensation when the applied surface was touched with a finger.
⊚: Natural feeling on the skin with no discomfort, smooth tactile sensation, no stickiness.
○: Slight discomfort in feeling on the skin or slight stickiness.
Δ: Somewhat unnatural feeling on the skin or unsatisfactory smoothness in feeling to touch.
x: Tight or irritated skin or stickiness with lack of smooth tactile sensation.

5. Finish: judged visually and in terms of overall satisfaction with the cosmetic effect.
⊚: Very satisfied. ○: Satisfied. Δ: Acceptable. x: Not satisfied.

[Lipstick Formulations and Evaluation Results]
See tables 23 to 25 below. (All units are wt. %)

In addition, FA 4002 ID in the tables is a 40 wt. % isododecane solution of an (acrylates/poly(trimethylsiloxy methacrylate)) copolymer, and DC 593 is a dimethylpolysiloxane (100 cst) solution containing 33 wt. % of trimethylsiloxy silicic acid.

TABLE 15

Lipstick formulations, evaluation results (1): practical examples

| No. | Component | Practical Example 12 | Practical Example 13 | Practical Example 14 |
|---|---|---|---|---|
| 1 | Polyethylene wax | 15.0 | 15.0 | 15.0 |
| 2 | Hydrogenated polyisobutene | 25.0 | 25.0 | 25.0 |
| 3 | FA 4002 ID | 15.0 | 15.0 | 15.0 |
| 4 | DC 593 | 5.0 | 5.0 | 5.0 |
| 5 | Isododecane | 20.0 | 20.0 | 20.0 |
| 6 | Composition of production example 5 (containing silicone compound No. 5) | 10.0 | — | — |
| 7 | Composition of production example 7 (containing silicone compound No. 7) | — | 10.0 | — |
| 8 | Composition of production example 12 (containing silicone compound No. 12) | — | — | 10.0 |
| 16 | Coloring pigment | 10.0 | 10.0 | 10.0 |
| | Total | 100.0 | 100.0 | 100.0 |
| Evaluation | Resistance to color migration Initial/4 hours/ 7 hours/9 hours | ⊚/⊚/⊚/⊚ | ⊚/⊚/⊚/⊚ | ⊚/⊚/⊚/⊚ |
| | Resistance to color rub-off Initial/4 hours/ 7 hours/9 hours | —/⊚/⊚/⊚ | —/⊚/⊚/⊚ | —/⊚/⊚/⊚ |
| | Tendency not to spread Initial/4 hours/ 7 hours/9 hours | ⊚/⊚/⊚/⊚ | ⊚/⊚/⊚/⊚ | ⊚/⊚/⊚/⊚ |
| | Natural feeling on the skin with no discomfort Initial/4 hours/ 7 hours/9 hours | ⊚/⊚/⊚/⊚ | ⊚/⊚/⊚/⊚ | ⊚/⊚/⊚/⊚ |
| | Finish Initial/4 hours/ 7 hours/9 hours | ⊚/⊚/⊚/⊚ | ⊚/⊚/⊚/⊚ | ⊚/⊚/⊚/⊚ |

TABLE 16

Lipstick formulations, evaluation results (2): comparative examples

| No. | Component | Comparative Example 8 | Comparative Example 9 | Comparative Example 10 |
|---|---|---|---|---|
| 1 | Polyethylene wax | 15.0 | 15.0 | 15.0 |
| 2 | Hydrogenated polyisobutene | 25.0 | 25.0 | 25.0 |
| 3 | FA 4002 ID | 15.0 | 15.0 | 15.0 |
| 4 | DC 593 | 5.0 | 5.0 | 5.0 |
| 5 | Isododecane | 20.0 | 20.0 | 20.0 |

TABLE 16-continued

Lipstick formulations, evaluation results (2): comparative examples

| No. | Component | Comparative Example 8 | Comparative Example 9 | Comparative Example 10 |
|---|---|---|---|---|
| 9 | Composition of comparative production example 4 (containing silicone compound RE4) | 10.0 | — | — |
| 10 | Composition of comparative production example 5 (containing silicone compound RE5) | — | 10.0 | — |
| 11 | Composition of comparative production example 6 (containing silicone compound RE6) | — | — | 10.0 |
| 16 | Coloring pigment | 10.0 | 10.0 | 10.0 |
| | Total | 100.0 | 100.0 | 100.0 |
| Evaluation | Resistance to color migration Initial/4 hours/7 hours/9 hours | X/X/X/X | ○/Δ/Δ/Δ | Δ/Δ/X/X |
| | Resistance to color rub-off Initial/4 hours/7 hours/9 hours | —/Δ/X/X | —/○/Δ/ΔX | —/○/○Δ |
| | Tendency not to spread Initial/4 hours/7 hours/9 hours | ○/○/Δ Δ | ○/○/○/Δ | ○/○/Δ/Δ |
| | Natural feeling on the skin with no discomfort Initial/4 hours/7 hours/9 hours | X/X/X/X | Δ/Δ/X X | Δ/Δ/X X |
| | Finish Initial/4 hours/7 hours/9 hours | X/X/X/X | ○~Δ/Δ/Δ/X | X/X/X/X |

TABLE 17

Lipstick formulations, evaluation results (3): comparative examples and practical examples

| No. | Component | Comparative Example 11 | Comparative Example 12 | Comparative Example 13 | Practical Example 15 |
|---|---|---|---|---|---|
| 1 | Polyethylene wax | 15.0 | 15.0 | 15.0 | 15.0 |
| 2 | Hydrogenated polyisobutene | 25.0 | 25.0 | 25.0 | 25.0 |
| 3 | FA 4002 ID | 15.0 | 15.0 | 15.0 | 15.0 |
| 4 | DC 593 | 5.0 | 5.0 | 5.0 | 5.0 |
| 5 | Isododecane | 20.0 | 20.0 | 20.0 | 20.0 |
| 12 | Composition of comparative production example 7 (containing silicone compound RE7) | 10.0 | — | — | — |
| 13 | Composition of comparative production example 8 (containing silicone compound RE8) | — | 10.0 | — | — |
| 14 | Composition of production example 2 (containing silicone compound No. 2) | — | — | 10.0 | — |
| 15 | Composition of production example 10 (containing silicone compound No. 10) | — | — | — | 10.0 |

TABLE 17-continued

Lipstick formulations, evaluation results (3): comparative examples and practical examples

| No. | Component | Comparative Example 11 | Comparative Example 12 | Comparative Example 13 | Practical Example 15 |
|---|---|---|---|---|---|
| 16 | Coloring pigment | 10.0 | 10.0 | 10.0 | 10.0 |
| | Total | 100.0 | 100.0 | 100.0 | 100.0 |
| Evaluation | Resistance to color migration Initial/4 hours/ 7 hours/9 hours | Δ/X/X/X | O/O/O/O | Δ/X/X/X | O/O/O/Δ |
| | Resistance to color rub-off Initial/4 hours/ 7 hours/9 hours | —/O/O/O | —/O/O/O | —/O/Δ/Δ~X | —/◉/◉/O |
| | Tendency not to spread Initial/4 hours/ 7 hours/9 hours | O/O/Δ/Δ | X/X/X/X | O/O/Δ/Δ | O/O/O/Δ |
| | Natural feeling on the skin with no discomfort Initial/4 hours/ 7 hours/9 hours | Δ/Δ/X/X | Δ/Δ/Δ/Δ | Δ/Δ/X/X | O/O/O/O |
| | Finish Initial/4 hours/ 7 hours/9 hours | Δ/Δ/X/X | Δ/Δ/Δ/Δ | Δ/Δ/X/X | O/O/O/Δ |

Practical Examples 16 to 18 and Comparative Example 14

Gel Compositions

Gel compositions were prepared by blending the compositions shown in table 18 according to the procedure described below using a homo-disper mixer. In the table, the numbers denote the number of parts (by weight) added. In addition, the obtained gel compositions were evaluated according to the criteria given below using the testing procedures described below.

Preparation Procedure

A. Components 1 to 6 were placed in a vessel, heated to 60° C., mixed, and uniformly melted.

B. This mixture was allowed to return to room temperature, and component 7 was added to A and uniformly blended/dispersed therewith.

C. While agitating B at 1,200 rpm in a homo-disper mixer, component 8 was gradually added dropwise thereto, and when the mixture thickened/gelled, the addition of water was stopped.

D. The preparation was completed by agitating in this condition for a further 1 minute. The amount of water added (wt. %) until the mixture gelled was recorded.

Note: Because the amount of water required until the mixture gelled differed according to the structure and the like of the silicone compound used, the total amount of the gel compositions differed according to the formulation.

Test Procedure

1. The properties of the obtained gel compositions (presence/absence of gelling) were judged visually and by tactile sensation.

2. 5 minutes after spreading 0.10 g of a gel composition on the back of the hand, the tactile sensation and the feeling on the skin were judged. Furthermore, the appearance of the applied part was judged as good or bad.

Evaluation

1. Presence/absence of gelling (gel properties)

◉: Complete gelling.

O: Syrup-like to soft gel.

2. Tactile sensation and feeling on the skin

O: Natural feeling on the skin, light touch, no unpleasant stickiness.

x: Persistent greasiness or stickiness.

3. Appearance of applied part

◉: Natural matte appearance.

x: Conspicuous oily glare.

TABLE 18

Gel composition formulations and evaluation results (practical examples/comparative examples)

| No. | Component | Practical Example 16 | Practical Example 17 | Practical Example 18 | Comparative Example 14 |
|---|---|---|---|---|---|
| 1 | D5 | 43.2 | 43.2 | 43.2 | 43.2 |
| 2 | 6 cst | 3.4 | 3.4 | 3.4 | 3.4 |
| 3 | Composition of production example 5 | 40.7 | — | — | — |

TABLE 18-continued

Gel composition formulations and evaluation results
(practical examples/comparative examples)

| No. | Component | Practical Example 16 | Practical Example 17 | Practical Example 18 | Comparative Example 14 |
|---|---|---|---|---|---|
| | (containing silicone compound No. 5) | | | | |
| 4 | Composition of production example 8 (containing silicone compound No. 8) | — | 40.7 | — | — |
| 5 | Composition of production example 12 (containing silicone compound No. 12) | — | — | 40.7 | — |
| 6 | Composition of comparative production example 2 (containing silicone compound RE2) | — | — | — | 40.7 |
| 7 | Ethanol | 12.7 | 12.7 | 12.7 | 12.7 |
| | Sub-total | 100.0 | 100.0 | 100.0 | 100.0 |
| 8 | Ion exchange water | 8.5 | 8.5 | 6.5 | 2.5 |
| | Total | 108.5 | 108.5 | 106.5 | 102.5 |
| | Presence/absence of gelling | ⊚ | ○ | ⊚ | ⊚ |
| | Tactile sensation and feeling on the skin | ○ | ○ | ○ | X |
| | Appearance of applied part | ⊚ | ⊚ | ⊚ | X |

Practical Examples 19 to 26

Gel Compositions

Gel compositions were prepared by blending the compositions shown in tables 18 to 19 according to the procedure described below using a homo-disper mixer. In the table, the numbers denote the number of parts (by weight) added. In addition, the obtained gel compositions were evaluated according to the criteria given below using the testing procedures described below.

Preparation Procedure

A. Components 1 to 4 were placed in a vessel, heated to 60° C., mixed, and uniformly melted.

B. This mixture was allowed to return to room temperature, and component 5 was added to A and uniformly blended/dispersed therewith.

C. While agitating B at 2,500 rpm in a homo-disper mixer, component 6 was gradually added dropwise thereto, and when the mixture thickened/gelled, the addition of water was stopped.

D. Agitation was continued in this state for a further 1 minute.

E. While agitating at 500 rpm, components 7 to 10 were added gradually to D. When all of components 7 to 10 had been added, these were blended by agitating for 5 minutes at 2,500 rpm until all the components had been homogenized.

Test Procedure 1. 0.15 g of the obtained gel composition was spread on the back of the hand, and the feeling to touch and sensation during use in the period between application and immediately following application were evaluated. Furthermore, the appearance of the applied part (skin impression) was evaluated.

2. 20 minutes after application, the "appearance of the applied part (skin impression)", "moisturizing feel", "powderiness of applied surface", "wrinkle-concealing effect" and "degree of cosmetic satisfaction (overall evaluation)" were evaluated.

Evaluation

1. Feeling to touch and sensation during use:
⊚: Excellent rich, smooth feeling to touch, and pleasant sensation during use.
○: Rich, smooth feeling to touch, and no problems in terms of sensation during use.
Δ: Somewhat unsatisfactory in terms of smoothness and sensation during use.

2. Appearance of applied part and feeling on the skin:
⊚: Matte appearance with no oiliness, natural impression in terms of appearance and feeling on the skin.
○: Matte appearance with no oiliness, but slightly unpleasant feeling on the skin.

3. Moisturizing feel:
⊚: Suitable and pleasant moist feel on the skin surface.
○: Able to maintain moisture on the skin surface.
Δ The skin felt dry 4. Powderiness of applied surface:
⊚: No feeling of powder rolling or dry feeling whatsoever.
○: Slight feeling of powder rolling.
x: Strong feeling of powder rolling and dry feeling.

5. Wrinkle-concealing effect:
⊚: No unevenness of application, good adhesive sensation, no conspicuous wrinkles whatsoever on the surface of the skin.
○: No unevenness of application, almost no conspicuous wrinkles whatsoever on the surface of the skin.
Δ: Powder embedded in wrinkles on the surface of the skin, conspicuous wrinkles in some parts.

6. Overall satisfaction with cosmetic effect:
⊚: Very satisfied. ○: Satisfied. Δ: Acceptable.

In the table, EP-9215 denotes an organopolysiloxane elastomer spherical powder, Benton 38 denotes hectorite treated with distearyldimethyl ammonium chloride, and Aerosil 200 denotes silica (silicic anhydride).

TABLE 19

Gel composition formulations and evaluation results (1): practical examples

| No. | Component | Practical Example 17 | Practical Example 18 | Practical Example 19 | Practical Example 20 |
|---|---|---|---|---|---|
| 1 | D5 | 43.2 | 43.2 | 43.2 | 43.2 |
| 2 | 6 cst | 3.4 | 3.4 | 3.4 | 3.4 |
| 3 | Composition of production example 5 (containing silicone compound No. 5) | 40.7 | 40.7 | 40.7 | 40.7 |
| 5 | Ethanol | 12.7 | 12.7 | 12.7 | 12.7 |
|  | Sub-total | 100.0 | 100.0 | 100.0 | 100.0 |
| 6 | Ion exchange water | 8.5 | 8.5 | 8.5 | 8.5 |
| 7 | EP-9215 | 42.8 | — | — | — |
| 8 | Benton 38 | — | 4.3 | — | — |
| 9 | Aerosil 200 | — | — | 0.4 | — |
| 10 | Nylon powder | — | — | — | 20.0 |
|  | Total | 151.3 | 112.8 | 108.9 | 128.5 |
|  | Appearance of applied part | ◎ | ◎ | ◎ | ◎ |
|  | Feeling to touch and sensation during use | ◎ | ○ | ○ | ○ |
|  | Moisturizing feel | ◎ | ◎ | ◎ | ◎ |
|  | No powdery feel | ◎ | ◎ | ○ | ◎ |
|  | Wrinkle-concealing effect | ◎ | ○ | ◎ | ◎ |
|  | Degree of cosmetic satisfaction | ◎ | ◎~○ | ◎~○ | ◎ |

TABLE 20

Gel composition formulations and evaluation results (2): practical examples

| No. | Component | Practical Example 21 | Practical Example 22 | Practical Example 23 | Practical Example 24 |
|---|---|---|---|---|---|
| 1 | D5 | 43.2 | 43.2 | 43.2 | 43.2 |
| 2 | 6 cst | 3.4 | 3.4 | 3.4 | 3.4 |
| 4 | Composition of production example 12 (containing silicone compound No. 12) | 40.7 | 40.7 | 40.7 | 40.7 |
| 5 | Ethanol | 12.7 | 12.7 | 12.7 | 12.7 |
|  | Sub-total | 100.0 | 100.0 | 100.0 | 100.0 |
| 6 | Ion exchange water | 6.5 | 6.5 | 6.5 | 6.5 |
| 7 | EP-9215 | 42.8 | — | — | — |
| 8 | Benton 38 | — | 4.3 | — | — |
| 9 | Aerosil 200 | — | — | 0.4 | — |
| 10 | Nylon powder | — | — | — | 20.0 |
|  | Total | 149.3 | 110.8 | 106.9 | 126.5 |
|  | Appearance of applied part | ◎ | ◎ | ◎ | ◎ |
|  | Feeling to touch and sensation during use | ◎ | ○ | ○ | ◎ |
|  | Moisturizing feel | ◎ | ◎ | ◎ | ◎ |
|  | No powdery feel | ◎ | ◎ | ◎ | ◎ |
|  | Wrinkle-concealing effect | ◎ | ○ | ◎ | ◎ |
|  | Degree of cosmetic satisfaction | ◎ | ◎~○ | ◎~○ | ◎ |

From the results shown above, it was understood that the gel compositions of practical examples 17 to 24 had excellent performance and degree of cosmetic satisfaction and had high value as gel cosmetic compositions.

Practical Examples 25 to 38

Gel Compositions

Gel compositions were prepared by blending the compositions shown in tables 21 to 24 according to the procedure described below using a homo-disper mixer. (In the tables, the numbers denote the number of parts (by weight) added)

Preparation Procedure

A. Components 1 to 6 were placed in a vessel, heated to 60° C., mixed, and uniformly melted.

B. This mixture was allowed to return to room temperature, and component 7 was added to A and uniformly blended/dispersed therewith.

C. Components 8 to 11 were placed in a separate vessel, mixed by agitating, and melted.

D. While agitating B at 2,500 rpm in a homo-disper mixer, C was gradually added thereto, and when the mixture thickened/gelled, the addition of C was stopped.

E. Agitation was continued in this state for a further 2 minutes.

F. While agitating at 500 rpm, components 12 to 15 were added gradually to E. When all of components 12 to 15 had been added, these were blended by agitating for 5 minutes at 2,500 rpm until all the components had been homogenized.

In the tables, D5 denotes decamethyl cyclopentasiloxane, SS-3408 denotes caprylyl methicone, and PEG denotes polyethylene glycol.

TABLE 21

Gel composition formulations (3): practical examples

| No. | Component | Practical Example 25 | Practical Example 26 | Practical Example 27 | Practical Example 28 |
|---|---|---|---|---|---|
| 1 | D5 | 18.0 | 18.0 | 18.0 | 18.0 |
| 2 | SS-3408 | 20.0 | 20.0 | 20.0 | 20.0 |
| 3 | Octyl methoxy cinnamate | 4.0 | 4.0 | 4.0 | — |
| 4 | Sucrose oleate ester | — | — | — | 2.0 |
| 5 | Decaglycerol oleate ester | — | — | — | 2.0 |
| 6 | Composition of production example 5 (containing silicone compound No. 5) | 48.0 | 48.0 | 48.0 | 48.0 |
| 7 | Ethanol | 10.0 | 10.0 | 10.0 | 10.0 |
|   | Sub-total | 100.0 | 100.0 | 100.0 | 100.0 |
| 8 | Ion exchange water | 9.4 | 9.4 | 8.5 | 8.9 |
| 9 | Sodium L-glutamate | 0.1 | — | — | 0.1 |
| 10 | Sodium citrate | — | 0.1 | — | — |
| 11 | PEG (Mw 6000) | — | — | 1.0 | — |
| 12 | EP-9215 | 42.8 | 42.8 | 42.8 | 42.8 |
|   | Total | 152.3 | 152.3 | 152.3 | 151.8 |

TABLE 22

Gel composition formulations (4): practical examples

| No. | Component | Practical Example 29 | Practical Example 30 | Practical Example 31 | Practical Example 32 |
|---|---|---|---|---|---|
| 1 | D5 | 18.0 | 18.0 | 18.0 | 18.0 |
| 2 | SS-3408 | 20.0 | 20.0 | 20.0 | 20.0 |
| 3 | Octyl methoxy cinnamate | — | — | 4.0 | 4.0 |
| 4 | Sucrose oleate ester | 2.0 | 2.0 | — | — |
| 5 | Decaglycerol oleate ester | 2.0 | 2.0 | — | — |
| 6 | Composition of production example 5 | 48.0 | 48.0 | 48.0 | 48.0 |

TABLE 22-continued

Gel composition formulations (4): practical examples

| No. | Component | Practical Example 29 | Practical Example 30 | Practical Example 31 | Practical Example 32 |
|---|---|---|---|---|---|
|  | (containing silicone compound No. 5) |  |  |  |  |
| 7 | Ethanol | 10.0 | 10.0 | 10.0 | 10.0 |
|  | Sub-total | 100.0 | 100.0 | 100.0 | 100.0 |
| 8 | Ion exchange water | 8.9 | 8.0 | 9.4 | 9.4 |
| 9 | Sodium L-glutamate | — | — | 0.1 | — |
| 10 | Sodium citrate | 0.1 | — | — | 0.1 |
| 11 | PEG (Mw 6000) | — | 1.0 | — | — |
| 12 | EP-9215 | 42.8 | 42.8 | — | — |
| 13 | Benton 38 | — | — | 4.0 | 4.0 |
|  | Total | 151.8 | 151.8 | 113.5 | 113.5 |

TABLE 23

Gel composition formulations (5): practical examples

| No. | Component | Practical Example 33 | Practical Example 34 | Practical Example 35 | Practical Example 36 |
|---|---|---|---|---|---|
| 1 | D5 | 18.0 | 18.0 | 18.0 | 18.0 |
| 2 | SS-3408 | 20.0 | 20.0 | 20.0 | 20.0 |
| 3 | Octyl methoxy cinnamate | 4.0 | 4.0 | 4.0 | — |
| 4 | Sucrose oleate ester | — | — | — | 2.0 |
| 5 | Decaglycerol oleate ester | — | — | — | 2.0 |
| 6 | Composition of production example 5 (containing silicone compound No. 5) | 48.0 | 48.0 | 48.0 | 48.0 |
| 7 | Ethanol | 10.0 | 10.0 | 10.0 | 10.0 |
|  | Sub-total | 100.0 | 100.0 | 100.0 | 100.0 |
| 8 | Ion exchange water | 8.5 | 9.4 | 8.5 | 8.9 |
| 9 | Sodium L-glutamate | — | — | — | 0.1 |
| 10 | Sodium citrate | — | 0.1 | — | — |
| 11 | PEG (Mw 6000) | 1.0 | — | 1.0 | — |
| 13 | Benton 38 | 4.0 | — | — | — |
| 14 | Aerosil 200 | — | 0.4 | 0.4 | 0.4 |
|  | Total | 113.5 | 109.9 | 109.9 | 109.4 |

TABLE 24

Gel composition formulations (6): practical examples

| No. | Component | Practical Example 37 | Practical Example 38 |
|---|---|---|---|
| 1 | D5 | 18.0 | 18.0 |
| 2 | SS-3408 | 20.0 | 20.0 |
| 3 | Octyl methoxy cinnamate | 4.0 | — |
| 4 | Sucrose oleate ester | — | 2.0 |
| 5 | Decaglycerol oleate ester | — | 2.0 |
| 6 | Composition of production example 5 (containing silicone compound No. 5) | 48.0 | 48.0 |
| 7 | Ethanol | 10.0 | 10.0 |
|  | Sub-total | 100.0 | 100.0 |
| 8 | Ion exchange water | 9.4 | 8.9 |
| 9 | Sodium L-glutamate | — | 0.1 |
| 10 | Sodium citrate | 0.1 | — |
| 15 | Nylon powder | 20.0 | 20.0 |
|  | Total | 129.5 | 129.0 |

Evaluation Results

The gel compositions obtained in practical examples 25 to 38 were in the form of uniform gels and were stable, with no changes in terms of appearance or form, even after being stored for 1 month at room temperature. Therefore, it was understood that these gel compositions had high value as gel cosmetic compositions.

Practical Examples 39 to 54

Emulsion Cosmetic Compositions

Emulsion cosmetic compositions were prepared by blending the compositions shown in tables 25 and 26 according to the procedure described below using a homo-disper mixer.

Preparation Procedure

A. Components 1 to 4 were placed in a vessel, and agitation at 2,500 rpm using a homo-disper mixer was started at room temperature.

B. While agitating, component 5 or a mixture of components 5 and 6 was added over a period of 10 minutes.

C. Matter adhered to the walls of the vessel was removed using a spatula, agitation and mixing was carried out again for a period of 5 minutes so that all the components were uniformly mixed.

TABLE 25

Emulsion cosmetic composition formulations
(1): practical examples

| No. | Component | Practical Example 39 | Practical Example 40 | Practical Example 41 | Practical Example 42 |
|---|---|---|---|---|---|
| 1 | Gel composition of practical example 17 | 35.0 | — | — | — |
| 2 | Gel composition of practical example 18 | — | 35.0 | — | — |
| 3 | Gel composition of practical example 19 | — | — | 35.0 | — |
| 4 | Gel composition of practical example 20 | — | — | — | 35.0 |
| 5 | Ion exchange water | 65.0 | 65.0 | 65.0 | 65.0 |
| | Total | 100.0 | 100.0 | 100.0 | 100.0 |

TABLE 26

Emulsion cosmetic composition formulations
(2): practical examples

| No. | Component | Practical Example 43 | Practical Example 44 | Practical Example 45 | Practical Example 46 |
|---|---|---|---|---|---|
| 1 | Gel composition of practical example 21 | 35.0 | — | — | — |
| 2 | Gel composition of practical example 22 | — | 35.0 | — | — |
| 3 | Gel composition of practical example 23 | — | — | 35.0 | — |
| 4 | Gel composition of practical example 24 | — | — | — | 35.0 |
| 5 | Ion exchange water | 55.0 | 55.0 | 55.0 | 55.0 |
| 6 | 1,3-butylene glycol | 10.0 | 10.0 | 10.0 | 10.0 |
| | Total | 100.0 | 100.0 | 100.0 | 100.0 |

Evaluation Results

The emulsion cosmetic compositions obtained in practical examples 39 to 42 had uniform cream-like to milk-like appearances, were stable, and underwent no changes even when stored for 1 month at room temperature.

The emulsion cosmetic compositions obtained in practical examples 43 to 46 had uniform paste-like to cream-like appearances, were stable, and underwent no changes even when stored for 1 month at room temperature.

Next, production examples of silicone compound Nos. 13 and 14, which are used in other embodiments of the present invention, will be given.

Production Example 13

Synthesis of Silicone Compound No. 13

Step 1:

94.6 g of a methylhydrogenpolysiloxane expressed by the average composition formula $MD_{330}D^H{}_{80}M$ and 10.4 g of a vinyl tris(trimethylsiloxy)silane expressed by the average composition formula $CH_2=CH-Si(OSiMe_3)_3$ were placed in a reaction vessel. Then, 0.25 g of an IPA solution of a platinum-1,3-divinyl-1,1,3,3-tetramethyldisiloxane complex (Pt concentration: 0.4 wt. %) was added at 35° C. while agitating under a nitrogen stream. After the temperature rise caused by generated heat leveled off, 10.4 g of the vinyl tris(trimethylsiloxy)silane (second adding) was added and the mixture was reacted in the same way. After the temperature rise caused by generated heat leveled off, 10.4 g of the vinyl tris(trimethylsiloxy)silane (third adding) was added and the mixture was reacted in the same way. Then, 2 g of the reaction liquid was sampled and it was confirmed that the reaction rate was not in error through an alkali decomposition gas generation method.

Step 2:

35.3 g of an allyl polyether expressed by the average composition formula $CH_2=CH-CH_2-O(C_2H_4O)_{19}(C_3H_6O)_{19}H$, 0.02 g of natural vitamin E, and 60 g of IPA were added to the reaction liquid. Then, 0.25 g of the platinum catalyst solution described above was added. After the temperature rise caused by generated heat leveled off, the mixture was reacted for two hours at from 65 to 80° C. and, thereafter, it was confirmed that the reaction rate was not in error through the same method described above.

Step 3:

13.0 g of 1-hexadecene was added to the reaction liquid that had a temperature of about 65° C. After the temperature rise caused by generated heat leveled off, 13.0 g of the 1-hexadecene (second adding) was added and the mixture was reacted in the same way. After the temperature rise caused by generated heat leveled off, 13.0 g of the 1-hexadecene (third adding) and 0.25 g of the platinum catalyst solution were added, and the mixture was reacted for three hours at from 65 to 80° C. Then, 2 g of the reaction liquid was sampled and it was confirmed that the reaction was complete through an alkali decomposition gas generation method.

Step 4:

200 g of a caprylyl methicone diluent (SS-3408) was added and dissolved and, thereafter, the mixture was heated under reduced pressure to remove the IPA and low-boiling components by distillation. The mixture was then filtered. Thus, a mixed liquid of a novel polyether-modified silicone having a long chain alkyl group and a siloxane dendron structure expressed by the average composition formula $MD_{330}D^{R*12}{}_{45}D^{R*31}{}_{30}D^{R*26}{}_{5}M$ and caprylyl methicone, at a weight ratio of 50:50, was obtained.

In this formula, $R^{*12}=-C_{16}H_{33}$
$R^{*31}=-C_2H_4Si(OSiMe_3)_3$
$R^{*26}=-C_3H_6O(C_2H_4O)_{19}(C_3H_6O)_{19}H$ This product was a gray-brown color uniform viscous liquid having semi-transparency.

Production Example 14

Synthesis of Silicone Compound No. 14

Step 1:

110.3 g of a methylhydrogenpolysiloxane expressed by the average composition formula $MD_{330}D^H{}_{80}M$ and 12.1 g of a vinyl tris(trimethylsiloxy)silane expressed by the average composition formula $CH_2=CH-Si(OSiMe_3)_3$ were placed in a reaction vessel. Then, 0.25 g of an IPA solution of a platinum-1,3-divinyl-1,1,3,3-tetramethyldisiloxane complex (Pt concentration: 0.4 wt. %) was added at 35° C. while agitating under a nitrogen stream. After the temperature rise caused by generated heat leveled off, 12.1 g of the vinyl tris(trimethylsiloxy)silane (second addition) was added and the mixture was reacted in the same way. After the temperature rise caused by generated heat leveled off, 12.1 g of the vinyl tris(trimethylsiloxy)silane (third addition) was added and the mixture was reacted in the same way. Then, 2 g of the reaction liquid was sampled and it was confirmed that the reaction rate was not in error through an alkali decomposition gas generation method.

Step 2:

8.0 g of a polyglycerin monoallyl polyether, 0.02 g of natural vitamin E, and 60 g of IPA were added to the reaction liquid. Then, 0.25 g of the platinum catalyst solution described above was added. After the temperature rise caused by generated heat leveled off, the mixture was reacted for two hours at from 65 to 80° C. and, thereafter, it was confirmed that the reaction rate was not in error through the same method described above.

Step 3:

15.1 g of 1-hexadecene was added to the reaction liquid that had a temperature of about 65° C. After the temperature rise caused by generated heat leveled off, 15.1 g of the 1-hexadecene (second addition) was added and the mixture was reacted in the same way. After the temperature rise caused by generated heat leveled off, 15.2 g of the 1-hexadecene (third addition) and 0.25 g of the platinum catalyst solution were added, and the mixture was reacted for three hours at from 65 to 80° C. Then, 2 g of the reaction liquid was sampled and it was confirmed that the reaction was complete through an alkali decomposition gas generation method.

Step 4:

200 g of a caprylyl methicone diluent (SS-3408) was added and dissolved and, thereafter, the mixture was heated under reduced pressure to remove the IPA and low-boiling components by distillation. The mixture was then filtered. Thus, a mixed liquid of a novel polyglycerin-modified silicone having a long chain alkyl group and a siloxane dendron structure expressed by the average composition formula $MD_{330}D^{R*12}_{45}D^{R*31}_{30}D^{R*22}_{5}M$ and caprylyl methicone, at a weight ratio of 50:50, was obtained.

In this formula, $R^{*12}=-C_{16}H_{33}$
$R^{*31}=-C_2H_4Si(OSiMe_3)_3$
$R^{*22}$ is expressed by $-C_3H_6O-X$, where "X" is the tetraglycerin portion.

This product had a milky white uniform gum-like form.

Moreover, the polyglycerin monoallyl ether was synthesized by ring-opening polymerizing 3 molar equivalents of glycidol with 1 mole of a glycerin monoallyl ether, and had a structure in which an average of 4 moles of glycerin were added. Moreover, the glycerin monoallyl ether has two hydroxyl groups that can both react with the glycidol and the polyglycerin portion therefore includes not only a straight chain structure, but also a branched structure.

Preparation and Evaluation of Water-In-Oil Emulsion Transparent Soft Gel Anti-Perspirants Practical Examples 47 to 48 and Comparative Examples 15 to 16

Water-in-oil emulsion transparent soft gel anti-perspirants were prepared as an example of the topical composition according to the present invention. The results of evaluations of the properties thereof are described in practical examples 47 to 48 and comparative examples 15 to 16.

The water-in-oil emulsion transparent soft gel anti-perspirants were prepared by mixing and emulsifying the components shown in the formulations (compositions) in table 27 according to the following procedure. Here, the co-modified organopolysiloxane (silicone compound) according to the present invention functions both as a thickening/gelling agent and as an emulsifier having a surface active effect.

Preparation Procedure

1. Oil phase components were measured out into a 200 mL container according to the amounts shown in Table 27.

2. These were heated to 60° C. and the silicone compound was dispersed/dissolved in the oil agent by occasional shaking.

(Oil Phase A)

3. Saw teeth of a homo-disper were immersed in the oil phase A and the container was fixed. Then, the mixture was agitated. While cooling, agitation was continued until the entire mixture became a uniform solution.

4. Specified amounts of the aqueous phase components were placed in another cup (with the exception of ion exchange water No. 14, shown last), and mixed and dissolved using a spatula. (aqueous phase B)

5. Two or three drops of each of these two phases were sampled, and refractive indices (RI) of each at 25° C. were measured.

6. The up to 1.0 parts of ion exchange water (No. 14) shown last was added in small portions so that the RI value of the aqueous phase was within 0.0001 units and matched the RI of the oil phase. This process was repeated until the desired matching of the RI values was achieved.

7. Using a homo-disper at a rotation speed of 3,000 rpm, the aqueous phase B was added gradually over a period of about 10 minutes to the oil phase A at room temperature while agitating. During this process, it was observed whether or not the contents of the container had formed a gel composition.

8. Agitation was halted after agitating for two more minutes, oil component and aqueous component adhered to the inner wall of the container was scraped off by using a spatula and mixed with the produced W/O emulsion composition.

9. The mixture was agitated for 3 minutes at a speed of 3,000 rpm using the homo-disper. Thus the preparation procedure was completed.

The properties of the obtained water-in-oil emulsion transparent soft gel anti-perspirant were tested according to the following method, and the results of functional evaluations thereof are shown in Table 27.

Test Procedure

1. In preparation procedure 7, it was judged visually and by touch whether or not a gel composition had been produced during the period in which the aqueous phase B was added, up to the point at which this addition was complete.

2. The appearance (transparency) and form of the obtained anti-perspirant was observed visually.

3. Furthermore, the refractive index (RI) and viscosity at 25° C. were measured.

4. The obtained anti-perspirant was applied to the skin in order to evaluate tactile sensation and non-whitening performance. Tactile sensation on the skin was measured via subjective comparison and non-whitening was also judged via subjective comparison.

5. Two 35 mL glass bottles were prepared in which 25 g of the anti-perspirant was placed. The bottles were capped, and one was placed in a 50° C. constant temperature bath and the other in a −5° C. constant temperature bath. After two weeks, the bottles were removed from the baths and returned to room temperature, after which the anti-perspirants were examined for changes in appearance and form.

Evaluation

Each criterion was evaluated based on the following guidelines.

"Gel formation": Judged visually and by touch whether or not gelling had occurred (whether or not a gel composition had been produced) during the preparation process.

"Appearance": Transparency of the anti-perspirant was judged visually through a 100 mL glass bottle.

"Form": Judged by touch whether or not the form of the anti-perspirant was a gel.

"RI": The refractive index at 25.0° C. of the obtained anti-perspirant was measured using an RX-7000α digital refractometer (manufactured by ATAGO Co., Ltd.).

"Viscosity": The viscosity at 25.0° C. was measured using an E type viscometer (VISCONIC EMD, manufactured by Tokimec. Inc) and a medium cone rotor (3°×R14). Moreover, the rotation speed of the rotor was 0.5 rpm.

"Tactile sensation": A rating of "superior" or "inferior" was given in terms of the feeling to touch (lack of stickiness) after a single application of 0.2 g of the anti-perspirant to the forearm.

◯: No stickiness, not noticeable
x: Stickiness was noticeable

Non-whitening performance: The presence of whiteness was determined visually after a single application of 0.2 g of the anti-perspirant to the forearm and 15 minutes of drying.

◯: No whiteness was observed
Δ: Some whiteness was observed
x: Applied area appeared white Stability: After a storage stability test, the appearance and form of the anti-perspirant were visually confirmed.

◯: Semi-transparent to transparent, no changes in appearance or soft gel form observed.
Δ: The soft gel form was maintained, but transparency was slightly reduced.
x: Appearance became opaque or non-uniform. Alternatively, a soft gel form did not occur.

TABLE 27

Water-in-oil emulsion transparent soft gel anti-perspirant formulations and evaluation results (1)

| No. | Component | Practical Example 47 | Practical Example 48 | Comparative Example 15 | Comparative Example 16 |
|---|---|---|---|---|---|
| — | Portion A: Oil phase | — | — | — | — |
| 1 | Dimethylpolysiloxane (2 cst) | 13.0 | 12.5 | 9.0 | 12.5 |
| 2 | SS-3408 | — | — | 3.5 | 3.5 |
| 3 | Dimethylpolysiloxane (20 cst) | 4.0 | 3.0 | 3.0 | 3.0 |
| 4 | Dimethylpolysiloxane (50 cst) | — | 1.0 | 1.0 | 1.0 |
| 5 | Isopropyl palmitate | 1.0 | 1.0 | 1.0 | 1.0 |
| 6 | Silicone compound No. 14 (Modified silicone: SS-3408 = 50:50 mixture) | 6.0 | 7.0 | — | — |
| 7 | silicone compound RE2 (Modified silicone:2 cst = 50:50 mixture) | — | — | 7.0 | — |
| 8 | Silicone compound RE6 | — | — | — | 3.5 |
| — | Portion B: Aqueous phase | — | — | — | — |
| 9 | Ion exchange water | 14.5 | 13.2 | 13.2 | 13.2 |
| 10 | Propylene glycol | 10.0 | 10.0 | 10.0 | 10.0 |
| 11 | POE (20) sorbitan monooleate | 0.66 | 0.66 | 0.66 | 0.66 |
| 12 | 50% aluminum chlorohydrate aqueous solution | 40.0 | 40.0 | 40.0 | 40.0 |
| 13 | 70% sorbitol aqueous solution | 13.6 | 13.4 | 13.4 | 13.4 |
| 14 | Ion exchange water (for balancing with the RI of Portion A) | 0.15 | 0.05 | 2.75 | 0.00 |
| | Total | ~103 | ~102 | ~105 | ~102 |
| Measurement | RI of portion A (at 25° C.) | 1.4018 | 1.4021 | 1.4012 | 1.4028 |
| | RI of portion B (at 25° C.) | 1.4018 | 1.4021 | 1.4012 | 1.4028 |
| | Final RI (at 25° C.) | 1.4020 | 1.4025 | 1.4028 | 1.4035 |
| Evaluation | Gel composition produced | ◯ | ◯ | ◯ | X |
| | Appearance of anti-perspirant | Transparent to semi-transparent | Transparent to semi-transparent | Transparent to semi-transparent | Transparent to semi-transparent |
| | Form of anti-perspirant | Soft gel | Soft gel | Soft gel | Liquid |
| | Viscosity of anti-perspirant (25° C.) | 106,000 | 153,000 | 50,300 | 3,300 |

TABLE 27-continued

Water-in-oil emulsion transparent soft gel anti-perspirant formulations and evaluation results (1)

| No. | Component | Practical Example 47 | Practical Example 48 | Comparative Example 15 | Comparative Example 16 |
|---|---|---|---|---|---|
| | Tactile sensation | ○ | ○ | ○ | ○ |
| | Non-whitening performance | ○ | ○ | ○ | Δ |
| | Stability of anti-perspirant (50° C., 2 W) | ○ | ○ | Δ | X |
| | Stability of anti-perspirant (−5° C., 2 W) | ○ | ○ | Δ | X |

Hereinafter, formulation examples of the cosmetic composition and the preparation for external use according to the present invention are described, but it is understood that the cosmetic composition and the preparation for external use according to the present invention are not limited to the types and compositions recited in these formulation examples. Note that in the formulation examples, all cosmetic raw materials that are described with a product number are products commercially available from Dow Corning Toray Co., Ltd.

Formulation Example 1

Rouge

| | Components | (wt. %) |
|---|---|---|
| 1. | Polyethylene wax (melting point 88° C.) | 2.0 |
| 2. | Polyethylene wax (melting point 107° C.) | 2.0 |
| 3. | Polyethylene-polypropylene copolymer | 2.0 |
| 4. | Microcrystalline wax | 2.0 |
| 5. | Candelilla wax | 3.0 |
| 6. | Carnauba wax | 3.0 |
| 7. | Ceresin | 3.0 |
| 8. | Isotridecyl isononanoate | 9.0 |
| 9. | 2-octyldodecanol | 10.0 |
| 10. | Neopentylglycol dicaprate | 10.0 |
| 11. | Diisostearyl malate | 10.0 |
| 12. | Polyglyceryl diisostearate | 10.0 |
| 13. | Castor oil | 10.0 |
| 14. | SH 556 *1) | 2.0 |
| 15. | DC 5200 Formulation Aid *2) | 5.0 |
| 16. | Composition of production example 7 (composition containing silicone compound No. 7) | 5.0 |
| 17. | Red No. 104 (1) aluminum lake | 1.0 |
| 18. | Red No. 201 | 1.0 |
| 19. | Red No. 202 | 1.0 |
| 20. | Yellow No. 4, aluminum lake | 1.0 |
| 21. | Blue No. 1, aluminum lake | 1.0 |
| 22. | Titanated mica | 1.0 |
| 23. | Titanium oxide-encapsulated silica | 2.0 |
| 24. | Titanium oxide-encapsulated nylon | 2.0 |
| 25. | Zirconium oxide-containing silica | 2.0 |

*1): Phenyl trimethicone
*2): Alkyl-modified silicone

Manufacturing Method

A: Components 1 to 16 are heated and dissolved. Then, components 17 to 25 are added and mixed uniformly.
B: A rouge is obtained by charging this mixture in a container.

Effects

The visual color of the rouge is bright and highly saturated. The color when actually applied to the lips is a bright fresh color similar to the visual color of the rouge itself. The rouge can be applied naturally with no discomfort and it is possible to obtain a uniform finish with no application unevenness. The rouge has good moisture resistance, water repellency, and anti-perspirant properties, has excellent cosmetic retainability and hardly suffers from dulling of color.

Formulation 2

Lipstick

| | Components | wt. % |
|---|---|---|
| 1. | Polyethylene-polypropylene copolymer | 5.0 |
| 2. | Candelilla wax | 5.0 |
| 3. | Carnauba wax | 5.0 |
| 4. | Vaseline | 10.0 |
| 5. | Cetyl 2-ethylhexanoate | 10.0 |
| 6. | Diglycerin diisostearate | 14.5 |
| 7. | Macadamia nut oil | 7.0 |
| 8. | Inulin stearate (Rheopearl ISK2; manufactured by Chiba Flour Milling Co., Ltd.) | 23.0 |
| 9. | Composition of production example 5 (composition containing silicone compound No. 5) | 2.0 |
| 10. | Red No. 201 | 1.0 |
| 11. | Red No. 202 | 3.0 |
| 12. | Yellow No. 4, aluminum lake | 3.0 |
| 13. | Titanium oxide | 1.0 |
| 14. | Black iron oxide | 0.5 |
| 15. | Iron oxide titanated mica | 10.0 |
| 16. | Preservative | q.s. |
| 17. | Perfume | q.s. |

Manufacturing Method

A: Components 1 to 9 are heated and dissolved. Then, components 10 to 16 are added and mixed uniformly.
B: Component 17 is added to A, and a container is filled with the mixture. Thus, a lipstick is obtained.

Effects

A natural feeling of application with no stickiness can be obtained, and the gloss on the lips is good. The lipstick has suitable sealing properties, moisture retention, and can protect the lips from drying and the like. The lipstick has good moisture resistance, water repellency, anti-perspirant properties, and has good cosmetic retainability.

Formulation Example 3

Rouge

| | Components | wt. % |
|---|---|---|
| 1. | Ceresin | 6.0 |
| 2. | Paraffin wax | 6.0 |
| 3. | Candelilla wax | 4.0 |
| 4. | 1-isostearoyl-3-myristoylglycerol | 22.5 |
| 5. | 2-ethylhexanoic acid triglyceride | 11.0 |
| 6. | Isopropyl palmitate | 22.5 |
| 7. | Jojoba oil | 10.0 |
| 8. | SH 3775 M *3) | 4.0 |
| 9. | Composition of production example 12 (composition containing silicone compound No. 12) | 4.0 |
| 10. | Titanium oxide | 3.0 |
| 11. | Red No. 201 | 3.0 |
| 12. | Red No. 202 | 2.0 |
| 13. | Yellow No. 4, aluminum lake | 2.0 |
| 14. | Antioxidant | q.s. |
| 15. | Perfume | q.s. |

*3): Polyether-modified silicone

Manufacturing Method

A: Components 1 to 9 are heated and dissolved. Then, components 10 to 14 are added and mixed uniformly.

B: Component 15 is added to A, and a container is filled with the mixture. Thus, a rouge is obtained.

Effects

The rouge can be applied naturally with no discomfort and it is possible to obtain a uniform finish with no application unevenness. The rouge hardly suffers from color migration, color rub-off, spreading, and the like, and has excellent cosmetic retainability. The rouge has suitable sealing properties and moisture retention, and can protect the lips from drying and the like.

Formulation Example 4

Rouge

| | Components | wt. % |
|---|---|---|
| 1. | Microcrystalline wax | 10.0 |
| 2. | Paraffin wax | 15.0 |
| 3. | Carnauba wax | 5.0 |
| 4. | Vaseline | 5.0 |
| 5. | Diisostearyl malate | 7.0 |
| 6. | Glyceryl triisostearate | 11.5 |
| 7. | Propylene glycol dicaprate | 7.0 |
| 8. | Inulin stearate (Rheopearl ISK2; manufactured by Chiba Flour Milling Co., Ltd.) | 2.0 |
| 9. | Composition of production example 10 (composition containing silicone compound No. 10) | 3.0 |
| 10. | Decamethyl cyclopentasiloxane | 10.0 |
| 11. | FA 4001 CM *4) | 3.0 |
| 12. | DC 593 *5) | 2.0 |
| 13. | Red No. 201 | 1.0 |
| 14. | Red No. 202 | 1.0 |
| 15. | Yellow No. 4 | 2.0 |
| 16. | Titanium oxide | 4.0 |
| 17. | Black iron oxide | 0.5 |
| 18. | Iron oxide titanated mica | 3.0 |
| 19. | Titanated mica | 2.0 |
| 20. | Purified water | 5.0 |
| 21. | 1,3-butylene glycol | 1.0 |
| 22. | Preservative | q.s. |
| 23. | Perfume | q.s. |

*4): Decamethyl cyclopentasiloxane solution of (acrylates/polytrimethylsiloxy methacrylate) copolymer (active component: 30 wt. %)
*5): Dimethylpolysiloxane (100 cst) solution containing 33 wt. % of trimethylsiloxysilicic acid Manufacturing Method A: Components 1 to 12 are heated and dissolved. Then, components 13 to 19 are added and mixed uniformly.

B: Components 20 to 22 are mixed uniformly and, thereafter, A is added and the mixture is mixed.

C: Component 23 is added to B, and a container is filled with the mixture. Thus, a rouge is obtained.

Effects

The rouge spreads smoothly and easily when applied to the lips. In addition, the rouge has a sensation during use that is free of stickiness and has excellent gloss on the lips. The rouge has good moisture resistance, water repellency and anti-perspirant properties, hardly suffers from color migration, color rub-off, spreading and the like, and has excellent cosmetic retainability.

Formulation Example 5

Oil-Based Solid Eye Shadow

| | Components | wt. % |
|---|---|---|
| 1. | Diisostearyl malate | 6.0 |
| 2. | Isotridecyl isononanoate | 10.0 |
| 3. | Liquid paraffin | 10.0 |
| 4. | Dimethylpolysiloxane (6 cst) | 8.0 |
| 5. | SS-3408 *6) | 10.0 |
| 6. | Silicic anhydride (Aerosil 200) | 1.2 |
| 7. | Composition of production example 12 (composition containing silicone compound No. 12) | 10.0 |
| 8. | Ceresin | 6.0 |
| 9. | Polyethylene wax | 6.0 |
| 10. | Blue No. 1 | 0.8 |
| 11. | Titanium oxide | 1.0 |
| 12. | Silicone treated titanium oxide-coated mica | 1.0 |
| 13. | titanium oxide/silica/titanium oxide-coated mica | 3.0 |
| 14. | Silicone treated mica | 10.0 |
| 15. | Poly(methyl methacrylate) | 5.0 |
| 16. | Silicone treated sericite | 12.0 |

*6): Caprylyl methicone

Manufacturing Method

A: Components 1 to 5 are mixed and heated to 90° C. Thereafter, component 6 is added and dispersed uniformly.

B: Components 7 to 9 are added to A and melted.

C: Components 10 to 16 are added to B and uniformly mixed.

D: The mixture is charged in a mold and cooled so as to obtain an oil-based solid eye shadow.

Effects

Sensation during use and finish of the oil-based solid eye shadow are superior. The oil-based solid eye shadow has good adhesive properties while producing a natural feeling of application with no discomfort. The oil-based solid eye shadow has good moisture resistance, water repellency, and anti-perspirant properties, hardly suffers from spreading and the like, and has excellent cosmetic retainability. In addition, the solid eye shadow hardly cracks.

Formulation Example 6

Eye Liner

| | Components | wt. % |
|---|---|---|
| 1. | Decamethyl cyclopentasiloxane | 17.0 |
| 2. | Isoparaffin | 10.0 |
| 3. | Dimethylpolysiloxane (2 cst) | 5.0 |
| 4. | SH 556 *7) | 5.0 |
| 5. | Glyceryl tri(2-ethylhexanoate) | 2.0 |
| 6. | Composition of Production Example 6 (composition containing siloxane compound No. 6) | 3.5 |
| 7. | FA 4001 CM *8) | 7.5 |
| 8. | DC 593 *9) | 7.5 |
| 9. | Ethanol | 1.0 |
| 10. | Dioctadecyldimethyl ammonium chloride-modified montmorillonite | 2.0 |
| 11. | Silicone treated black iron oxide | 10.0 |
| 12. | 1,3-butylene glycol | 5.0 |
| 13. | sodium dehydroacetate | q.s. |
| 14. | Preservative | q.s. |
| 15. | Purified water | 24.5 |

*7): Phenyl trimethicone
*8): Decamethyl cyclopentasiloxane solution of (acrylates/polytrimethylsiloxy methacrylate) copolymer (active component: 30 wt. %)
*9): Dimethylpolysiloxane (100 cst) solution containing 33 wt. % of trimethylsiloxy silicic acid Manufacturing Method
A: Components 1 to 10 are mixed, and component 11 is then added and dispersed uniformly therein. (Gel cosmetic composition)
B: Separately, components 12 to 15 are mixed.
C: B is gradually added to A in small amounts and emulsified so as to obtain an eye liner.
(Alternative Production Method)
A: Components 1 to 8 are heated to 60° C., mixed and uniformly melted.
B: This mixture was allowed to return to room temperature, and component 9 was added to A and uniformly blended/dispersed therewith.
C: While agitating and mixing B, an amount of component 15 equivalent to 1.5 wt. % of the overall composition is gradually added dropwise to B so as to transform the mixture into a gel. (Gel composition)
D: Component 10 is added to C and mixed/dispersed uniformly therein. (Gel cosmetic composition)
E: Component 11 is added to D and mixed/dispersed uniformly therein.
F: A mixture of components 12 to 14 and the remainder of component 15 (an amount equivalent to 23.0 wt. %) is prepared separately.
G: While stirring E, F is gradually added thereto, agitated, and mixed until the entire mixture is uniform, thereby obtaining an eye liner.
Effects The eye liner has a suitable viscosity for a product, is easy to use, spreads lightly, and can be easily applied. When applying the eye liner, there is a cool, refreshing feeling and it is possible to achieve a natural sensation during use with no stickiness. The eye liner has excellent moisture resistance, anti-perspirant properties, and therefore extremely good cosmetic retainability, and has good stability over time and in terms of product temperature.

Formulation Example 7

Foundation

| | Components | wt. % |
|---|---|---|
| 1. | Decamethyl cyclopentasiloxane | 27.0 |
| 2. | SH 556 *10) | 3.0 |
| 3. | Glyceryl trioctanoate | 10.0 |
| 4. | Composition of Production Example 11 (composition containing siloxane compound No. 11) | 4.0 |
| 5. | Benton 27 *11) | 0.5 |
| 6. | Hydrophobization-treated mixed powder *12) | 18.0 |
| 7. | Red iron oxide | 1.2 |
| 8. | Yellow iron oxide | 2.6 |
| 9. | Ultramarine blue | 0.1 |
| 10. | Black iron oxide | 0.1 |
| 11. | 1,3-butylene glycol | 7.0 |
| 12. | Sodium chloride | 0.5 |
| 13. | Preservative | q.s. |
| 14. | Perfume | q.s. |
| 15. | Purified water | 26.0 |

*10): Phenyl trimethicone
*11): Benzyldimethylstearylammonium chloride-treated hectorite (manufactured by Nationalred Co.)
*12): Product obtained by heat treating a mixed powder having the composition shown below with an amount of a dimethyl methylhydrogen polysiloxane equivalent to 1 wt. %.
a. Fine particulate titanium oxide 8.0
b. Fine particulate zinc oxide 4.0
c. Talc 3.0
d. Mica 3.0

Manufacturing Method
A: Components 1 to 6 are mixed, then components 7 to 10 are dispersed uniformly therein. (Gel cosmetic composition)
B: Components 11 to 13 and 15 are mixed and added to A, and the mixture is emulsified.
C: Component 14 is added to B so as to obtain a foundation.
Effects The foundation has no stickiness, spreads lightly, has excellent adhesion and has a natural sensation during use. In addition, the foundation has a glossy finish and has extremely excellent cosmetic retainability. The foundation has good stability over time and in terms of product temperature.

Formulation Example 8

Foundation

| | Components | wt. % |
|---|---|---|
| 1. | Dimethylpolysiloxane (2 cst) | 10.0 |
| 2. | Isododecane | 21.6 |
| 3. | Isostearyl diglyceryl succinate | 0.6 |
| 4. | SS-2910 *13) | 1.2 |
| 5. | Composition of Production Example 10 (composition containing siloxane compound No. 10) | 0.6 |
| 6. | BY 25-320 *14) | 1.5 |
| 7. | FZ-2250 *15) | 1.5 |
| 8. | FA 4002 ID *16) | 2.0 |
| 9. | DC 593 *17) | 2.0 |
| 10. | Covered iron oxide | 3.5 |
| 11. | Covered titanium dioxide | 6.8 |
| 12. | Nylon 12 | 8.0 |
| 13. | Ion exchange water | 40.0 |

-continued

| | Components | wt. % |
|---|---|---|
| 14. | Magnesium sulfate | 0.7 |
| 15. | Preservative | q.s. |

*13): Polyether-modified silicone
*14): Isoparaffin solution (20 wt. %) of dimethylpolysiloxane gum
*15): Isoparaffin solution (35 wt. %) of polyether-silicone block copolymer
*16): Isododecane solution of (acrylates/polytrimethylsiloxy methacrylate) copolymer (active component: 40 wt. %)
*17): Dimethylpolysiloxane (100 cst) solution containing 33 wt. % of trimethylsiloxysilicic acid Manufacturing Method
A: Components 1 to 9 are mixed and then components 10 to 12 are dispersed uniformly therein.
B: Components 13 to 15 are mixed and, thereafter, A is added and the mixture is emulsified. Thus, a foundation is obtained.

Effects
With the foundation, a cosmetic film that imparts a feeling of smoothness and substance can be obtained regardless of the foundation being spread lightly and easily. A sensation of dryness or tightness or stretching is, for the most part, not felt after application, adhesion to the skin is excellent, and cosmetic retainability is superior. The foundation has good stability over time and in terms of product temperature.

Formulation Example 9

Gel Cosmetic Composition

| | Components | wt. % |
|---|---|---|
| 1. | Decamethyl cyclopentasiloxane | 12.0 |
| 2. | SS-3408 *18) | 13.0 |
| 3. | Sucrose oleate ester | 1.3 |
| 4. | Decaglycerol oleate ester | 1.3 |
| 5. | Composition of Production Example 6 (composition containing siloxane compound No. 6) | 16.0 |
| 6. | Composition of Production Example 3 (composition containing siloxane compound No. 3) | 12.0 |
| 7. | SS-2910 *19) | 4.0 |
| 8. | Ethanol | 8.0 |
| 9. | Purified water | 5.9 |
| 10. | Sodium L-glutamate | 0.1 |
| 11. | EP-9215 *20) | 26.4 |

*18): Caprylyl methicone
*19): Polyether-modified silicone
*20): Silicone elastomer spherical powder Manufacturing Method
A: Components 1 to 7 are heated to 60° C., mixed, and uniformly melted.
B: This mixture was allowed to return to room temperature and component 8 was added to A and uniformly blended/dispersed therewith.
C: While agitating and mixing B, a solution obtained by dissolving component 10 in component 9 is gradually added dropwise to B so as to transform the mixture into a gel. (Gel composition)
D: Component 11 is gradually added to C and uniformly blended/dispersed therewith so as to obtain a gel cosmetic composition.

Effects
The gel cosmetic composition has a rich, smooth feeling to touch and has a pleasant, refreshing sensation during use with no oiliness. The gel cosmetic composition produces almost no feeling of dryness or of stretched skin following application, and imparts the skin with a moisturizing feel. The gel cosmetic composition produces a matte appearance with no oiliness, natural impression in terms of appearance, and feeling on the skin. The gel cosmetic composition has no unevenness of application, a good adhesive sensation, and leaves no conspicuous wrinkles on the surface of the skin. The gel cosmetic composition has good stability over time and in terms of product temperature.

Formulation Example 10

Cream-Like Emulsion Cosmetic Composition

| | Components | wt. % |
|---|---|---|
| 1. | Dimethylpolysiloxane (6 cst) | 10.0 |
| 2. | SS-3408 *21) | 10.0 |
| 3. | Cetyl 2-ethylhexanoate | 10.0 |
| 4. | Composition of Production Example 11 (composition containing siloxane compound No. 11) | 4.0 |
| 5. | Dipropylene glycol | 6.0 |
| 6. | Purified water | 58.0 |
| 7. | Sodium L-glutamate | 2.0 |

*21): Caprylyl methicone

Manufacturing Method
A: Components 5 to 7 are heated to 70° C., mixed, and uniformly melted.
B: Components 1 to 4 are heated to 60° C., mixed, and uniformly melted.
C: A and B are allowed to return to room temperature, emulsification is carried out by slowly adding A while agitating B in a homo-disper mixer so as to obtain a cream-like emulsion cosmetic composition.

Effects
The cosmetic composition spreads lightly when applied and achieves a smooth, moist sensation during use with no stickiness. Following application, the cosmetic composition produces a natural feeling on the skin and excellent durability in terms of moisturizing feel, and because skin dryness is suppressed, an effect of preserving skin springiness can be expected. Stability over time of the product is also excellent.

Formulation Example 11

Paste-Like Emulsion Cosmetic Composition

| | Components | wt. % |
|---|---|---|
| 1. | Dimethylpolysiloxane (6 cst) | 20.0 |
| 2. | SS-3408 *22) | 20.0 |
| 3. | Glyceryl tri(2-ethylhexanoate) | 20.0 |
| 4. | Octyl methoxy cinnamate | 8.0 |
| 5. | Composition of Production Example 7 (composition containing siloxane compound No. 7) | 4.0 |
| 6. | Trimethylsiloxysilicate | 1.0 |
| 7. | Low density polyethylene powder | 1.0 |
| 8. | Spherical polyethylene | 1.0 |
| 9. | Polystyrene powder | 1.0 |
| 10. | Polymethyl silsesquioxane powder | 3.0 |
| 11. | Ethanol | 2.0 |
| 12. | Dipropylene glycol | 6.0 |
| 13. | Purified water | 12.0 |

-continued

| | Components | wt. % |
|---|---|---|
| 14. | Sodium L-glutamate | 1.0 |
| 15. | Paraben | q.s. |

*22): Caprylyl methicone

Manufacturing Method

A: Components 1 to 6, 11 and 15 are mixed and uniformly melted.
B: While agitating A in a homo-disper mixer, components 7 to 10 are added and uniformly dispersed therein.
C: Components 12 to 14 are heated to 60° C., mixed, and uniformly melted.
D: B and C are allowed to return to room temperature. Emulsification is carried out by slowly adding C while agitating B in a homo-disper mixer so as to obtain a paste-like emulsion cosmetic composition.

Effects

The cosmetic composition spreads smoothly when applied and produces a natural, plain feeling on the skin with no stickiness. When applied, the cosmetic composition imparts the skin with a smooth feel and maintains a natural moisturizing feel. The cosmetic composition also achieves excellent protection from ultraviolet radiation and gives excellent product stability over time.

Formulation Example 12

Aerosol Anti-Perspirant Composition

| | Components | wt. % |
|---|---|---|
| 1. | Aluminum chlorohydrate | 12.00 |
| 2. | Decamethyl cyclopentasiloxane | 15.67 |
| 3. | Isopropyl myristate | 5.00 |
| 4. | Silicone compound No. 14 | 1.00 |
| 5. | Quaternium-18 hectorite | 1.00 |
| 6. | Propylene carbonate | 0.33 |
| 7. | Lectin | 5.00 |
| 8. | 1,1-difluoroethane (propellant) | 60.00 |

Manufacturing Method

A: Components 2 to 4 (oil phase portion) are mixed and formed into a uniform liquid.
B: Components 5 to 6 (powder suspending agent and clay activator) are mixed with the oil phase portion and uniformly dispersed.
C: The dispersion liquid of B is allowed to stand and thicken for 15 to 20 minutes.
D: While agitating C, component 1 and component 7 are added thereto.
E: This mixture is then homogenized using a mixing agitator having a strong shearing force, such as a homogenizer, so as to obtain a soft gel composition.
F: E is then transferred to an epoxy-phenol-treated aerosol can and a propellant is charged therein, thereby obtaining an aerosol anti-perspirant composition.

Effects

The aerosol anti-perspirant composition has good powder adhesion, is free of stickiness after application, and provides an appropriate dry sensation. Moreover, a smooth, natural feeling on the skin can be obtained.

Formulation Example 13

Gel Anti-Perspirant Stick

| | Components | wt. % |
|---|---|---|
| 1. | Aluminum-zirconium-tetrachlorohydrate-glycine | 24.0 |
| 2. | Dimethylpolysiloxane (2 cst) | 12.3 |
| 3. | SS-3408 *23) | 12.0 |
| 4. | Silicone compound No. 14 | 2.0 |
| 5. | XX 3006 Alkyl Sugar Siloxane *24) | 1.0 |
| 6. | Stearyl alcohol | 14.0 |
| 7. | Isopropyl myristate | 1.0 |
| 8. | Castor oil wax | 4.0 |
| 9. | Polydecene | 13.0 |
| 10. | DC 9041 Silicone Elastomer Blend *25) | 12.5 |
| 11. | Talc | 3.2 |
| 12. | Fragrance | 1.0 |

Manufacturing method
*23): Caprylyl methicone
*24): Sugar/long chain alkyl-co-modified silicone
*25) Product obtained by diluting crosslinking organopolysiloxane (dimethicone crosspolymer) with dimethylsiloxane (5 cst) (elastomer component: 16%)

Manufacturing Method

A: Components 2 to 8 are dissolved by heating and agitating at 80° C.
B: While maintaining at 80° C. and agitating vigorously, components 9 to 11 are added gradually to A and uniformly dispersed therein.
C: While maintaining at 65° C., component 1 is added gradually to B and uniformly dispersed therein through vigorous agitation.
D: While agitating, component 12 is added to C.
E: D is charged in a container and gelled by cooling.

Effects

The anti-perspirant stick has a moist, smooth feeling to touch, imparts a suitable moisturizing feel despite having low stickiness, and is excellent in terms of uniformity of appearance. The anti-perspirant stick softens the skin, and is therefore easy to rub into the skin during application. Moreover, the durability of the anti-perspirant effects is excellent.

Formulation Example 14

Oil-Based Gel Type Cleansing Agent

| | Components | wt. % |
|---|---|---|
| 1. | Liquid paraffin | 6.0 |
| 2. | Dimethylpolysiloxane | 6.0 |
| 3. | Glycerol tri(2-ethylhexanoate) | 50.0 |
| 4. | POE octyl dodecyl alcohol ether | 10.0 |
| 5. | Silicone compound No. 14 | 0.5 |
| 6. | Vitamin A palmitate | 2.0 |
| 7. | Resorcin derivative | 0.5 |
| 8. | Lavender oil | 0.001 |
| 9. | Sorbitol | 10.0 |
| 10. | Polyethylene glycol (PEG 400) | 5.0 |
| 11. | Acylmethyltaurine | 5.0 |
| 12. | Purified water | bal. |

Manufacturing Method

A: Components 1 to 7 are melted by being agitated, heated to 70° C., and then cooled to form an oil phase.

B: Separately, components 9 to 12 are mixed and dissolved to form an aqueous phase.
C: While agitating B in a homomixer, emulsification is carried out by slowly adding A, thereby obtaining an oil-based gel.

Effects

Because the oil-based gel is in the form of a gel and has good compatibility with skin, it is possible to ensure removal of make up stains and the like while allowing essential oil components to remain in the skin. It is possible to prevent skin dryness following application. Product stability over time is good.

Formulation Example 15

Gel Anti-Perspirant Stick

| | Components | wt. % |
|---|---|---|
| 1. | Octyldodecanol | 25.0 |
| 2. | 12-hydroxystearic acid | 7.0 |
| 3. | N-lauryl-glutamic acid-di-n-butylamide | 0.5 |
| 4. | Unilin 425 *26) | 0.5 |
| 5. | Unithox 450 *27) | 1.0 |
| 6. | Unithox 480 *27) | 1.0 |
| 7. | Dodecamethyl cyclohexasiloxane | 46.3 |
| 8. | Silicone compound No. 14 | 2.0 |
| 9. | Al/Zr trichlorohydrex glycinate | 25.0 |
| 10. | EDTA-2Na | 0.2 |
| 11. | Perfume | 1.0 |

*26) $C_{20}$-$C_{40}$ alcohol (manufactured by Baker Petrolite)
*27) EO adduct of $C_{20}$-$C_{40}$ alcohol (manufactured by Baker Petrolite)

Manufacturing Method
A: Components 1 to 8 are dissolved by heating and agitating at 90° C.
B: While maintaining at 80° C. and agitating, components 9 to 10 are added gradually to A and uniformly dispersed therein.
C: Component 11 is added to B, mixed well, and this mixture is then charged in a container and gelled by cooling.

Effects

The anti-perspirant stick has good compatibility with skin, softens skin, and can be easily pushed into the skin during application. The anti-perspirant stick can be applied lightly and smoothly, and an applied film thereof has suitable sealing properties and a suitable dry feeling to touch on skin. The anti-perspirant stick has good durability in terms of anti-perspirant effects and has good product stability over time.

Formulation Example 16

Gel Deodorant Stick

| | Components | wt. % |
|---|---|---|
| 1. | Octyl methoxy cinnamate | 25.0 |
| 2. | Isohexadecane | 40.0 |
| 3. | Dodecamethyl cyclohexasiloxane | 25.0 |
| 4. | 12-hydroxystearic acid | 7.0 |
| 5. | Silicone compound No. 14 | 1.0 |
| 6. | Perfume M' *28) | 2.0 |

*28) See the blended perfume composition example shown in table 28 below.

Manufacturing Method
A: Components 1 to 5 are dissolved by heating and agitating at 80° C.
B: While maintaining at 65 to 70° C. and agitating, component 6 is added to A and uniformly dispersed therein.
C: B is charged in a container and gelled by cooling.

Effects

During and following application, a suitable dry feeling to touch on skin is achieved and there is little feeling of residuality. The deodorant stick has good durability in terms of anti-perspirant effects, offers good protection from ultraviolet radiation, and has good product stability over time.

TABLE 28

Perfume composition example: Perfume M'

| Component | Content (%) |
|---|---|
| Aldehyde C-10 | 0.1 |
| Aldehyde C-11 Undecylenic | 0.1 |
| Aldehyde C-12 lauric | 0.1 |
| Aldehyde C-12 methyl nonyl acetaldehyde | 0.1 |
| Aldehyde C-14 peach | 0.1 |
| Ambrettolide | 0.2 |
| Ambroxane | 0.1 |
| Apricot base | 0.5 |
| Black pepper oil | 0.3 |
| Bacdanol | 1.0 |
| Benzoin siam resinoid | 0.3 |
| Benzyl acetate | 1.0 |
| Cyclogalbanate | 0.2 |
| Cyclohexyl salicylate | 5.0 |
| Cassis base 345 B | 0.1 |
| Cashmeran | 0.1 |
| Cetylia Base B | 1.0 |
| Citronellol | 2.5 |
| Coumarin | 1.0 |
| Damascenone | 0.1 |
| Dihydromyrcenol | 1.0 |
| Dipropylene glycol | 5.5 |
| Ethyl acetoacetate | 1.0 |
| Ethyl linalool | 2.0 |
| Ethyl vanillin | 0.1 |
| Eugenol | 1.0 |
| Evernyl | 0.1 |
| Florosa | 0.3 |
| Galaxolide 50 benzyl benzoate | 6.0 |
| γ-decalactone | 0.1 |
| Geraniol | 2.0 |
| Geranium oil | 0.3 |
| Grapefruit oil | 1.0 |
| Guava base | 3.0 |
| Heliotropine | 3.0 |
| Helional | 1.0 |
| Cis-3-hexenol | 0.1 |
| cis-3-hexenyl acetate | 0.1 |
| Hexyl cinnamic aldehyde | 0.5 |
| Indole pure | 0.1 |
| Ionone beta | 5.0 |
| Iris concrete | 0.1 |
| Iso E Super | 5.0 |
| Methyl ionone gamma | 4.0 |
| Jasmine base | 0.3 |
| Cis-jasmine | 0.2 |
| Karanal | 0.1 |
| Ligustral | 0.2 |
| Lilial | 7.0 |
| Linalol | 2.5 |
| Linalyl acetate | 1.5 |
| Lyral | 4.0 |
| Methyl dihydrojasmonate | 4.0 |
| Methyl octyne carbonate replacer | 0.1 |

TABLE 28-continued

Perfume composition example: Perfume M'

| Component | Content (%) |
|---|---|
| Musk T | 2.0 |
| Pentalide | 1.0 |
| Phenylethyl alcohol | 3.0 |
| Pineapple base | 2.0 |
| p-t-butyl-cyclohexyl acetate | 1.0 |
| Raspberry ketone | 0.2 |
| Rose oxide L | 0.1 |
| Rose phenone | 0.5 |
| Rose oil | 0.3 |
| Styralyl acetate | 0.2 |
| Terpineol | 2.0 |
| Tetrahydro muguol | 7.0 |
| Tonalide | 3.0 |
| Vanillin | 0.1 |
| Vertofix | 1.0 |
| Vetiver oil | 0.3 |
| Ylang ylang oil | 0.2 |
| Total | 100.0 |

Formulation Example 17

Gel Cream

| | Components | wt. % |
|---|---|---|
| 1. | Dimethylpolysiloxane (6 cst) | 8.0 |
| 2 | Decamethyl cyclopentasiloxane | 24.0 |
| 3. | Silicone compound No. 6 | 10.0 |
| 4. | Silicone rubber powder *29) | 6.0 |
| 5. | Hydrophobized silica *30) | 2.0 |
| 6. | Glucomannan | 0.2 |
| 7. | Pullulan | 0.2 |
| 8. | Agar powder (Japanese Pharmacopoeia) | 0.1 |
| 9. | Purified water | 49.5 |

*29): Crosslinked elastic polydimethyl siloxane
*30): Dimethylsilylated silicic anhydride Manufacturing Method A: Components 1 to 3 were heated, agitated at 70° C., and dissolved.

B: Components 4 to 5 are added to A, agitated vigorously, and uniformly dispersed therein.

C: Separately, components 6 to 9 are mixed to form a solution. The solution was heated to 70° C.

D: Emulsification is achieved by adding C in small amounts while holding the temperature of B at 70° C. and agitating uniformly in a homo-disper. Then, while agitating, the mixture is cooled to 30° C. so as to obtain a gel cream.

Effects

The gel cream is smooth, can easily be applied to the skin, and produces a moist, cool feeling with no stickiness when applied. The gel cream suppresses dry skin by exhibiting an excellent moisturizing effect, and can be expected to restore skin springiness following application. The gel cream produces a matte feel and achieves the effect of rendering small wrinkles and pores inconspicuous.

Formulation Example 18

Gel Lip Cream

| | Components | wt. % |
|---|---|---|
| 1. | Dimethylpolysiloxane (6 cst) | 20.0 |
| 2. | Dimethylpolysiloxane (2 cst) | 18.0 |
| 3. | SS-3408 *31) | 18.3 |
| 4. | DC 2503 Cosmetic Wax *32) | 19.0 |
| 5. | Silicone compound No. 14 | 1.0 |
| 6. | Hydrophobized silica (trimethylsilylated silicic anhydride) | 1.5 |
| 7. | Silicone rubber powder (crosslinked elastic polydimethyl siloxane) | 6.0 |
| 8. | Glucomannan | 0.5 |
| 9. | Pullulan | 1.0 |
| 10. | Glycerin | 2.7 |
| 11. | Ion exchange water | 10.0 |
| 12. | Paramethoxy octyl cinnamate | 2.0 |
| 13. | Menthol | q.s. |
| 14. | Camphor | q.s. |

*31): Caprylyl methicone
*32): Stearyl dimethicone

Manufacturing Method

A: Components 1 to 5 were heated and agitated at 70° C. and dissolved.

B: Components 6 to 7 are added to A, and mixed well and uniformly dispersed therein using a homo-disper.

C: Components 12 to 14 are added and dissolved while agitating B.

D: Separately, components 8 to 11 are mixed to form a solution. The solution was heated to 70° C.

E: Emulsification is achieved by adding D in small amounts while holding the temperature of C at 70° C. and agitating uniformly in a homo-disper. Then, while agitating, the mixture is cooled to 30° C. so as to obtain a gel lip cream.

Effects

The gel lip cream can be applied lightly and smoothly, and can impart the lips with a cool, moisturizing feeling. The film formed by applying the gel lip cream exhibits suitable sealing properties and moisturizing properties and can suppress drying of the lips. As a result, the gel lip cream can be expected to maintain springiness in the lips.

Formulation Example 19

Mascara

| | Components | wt. % |
|---|---|---|
| 1. | FA 4002 ID *33) | 19.0 |
| 2. | Palmitic acid/dextrin ethylhexanoate | 8.0 |
| 3. | Polyethylene wax | 3.5 |
| 4. | Beeswax | 6.5 |
| 5. | Lecithin | 0.5 |
| 6. | SS-3408 *34) | 21.0 |
| 7. | C11-12 Liquid isoparaffin | 19.0 |
| 8. | Silicone compound No. 14 | 4.0 |
| 9. | Iron oxide | 5.0 |
| 10. | Aerosil RY200 *35) | 3.5 |
| 11. | Talc | 10.0 |

*33): Isododecane solution of (acrylates/polytrimethylsiloxy methacrylate) copolymer (active component: 40%)
*34): Caprylyl methicone
*35): Aerosil RY200 (manufactured by Nippon Aerosil Co., Ltd.): Hydrophobized silica Manufacturing Method
A: Components 1 to 8 are mixed thoroughly and dissolved. As necessary, the mixture is heated to 40° C.
B: Components 9 to 11 are added to A and dispersed using a roller.

Effects

The product has suitable viscosity and is therefore easy to use. The mascara spreads easily, is free of stickiness and oiliness, has moisture resistance, water repellency, antiperspirant properties, and has excellent cosmetic retainability. The mascara also has superior stability and does not vary with temperature or time.

Formulation Example 20

Gel Aftershave Cream

|  | Components | wt. % |
|---|---|---|
| 1. | SS-3408 *36) | 35.0 |
| 2. | SS-2910 *37) | 2.9 |
| 3. | Silicone compound No. 7 | 5.0 |
| 4. | Polyethyleneglycol (molecular weight: 400) | 5.0 |
| 5. | Sodium L-glutamate | 2.0 |
| 6. | Allantoin | 0.1 |
| 7. | Aloe extract | 0.1 |
| 8. | Preservative | 0.1 |
| 9. | Antioxidant | 0.1 |
| 10. | Perfume | 0.7 |
| 11. | Purified water | 49.0 |

*36): Caprylyl methicone
*37): Polyether-modified Silicone

Manufacturing Method
A: Components 1 to 4 and component 10 are heated and mixed.
B: Components 5 to 9 and component 11 are heated and mixed.
C: B is added in small amounts to A and emulsified so as to obtain a gel aftershave cream.

Effects

The gel aftershave cream does not drip when applied due to having suitable viscosity, imparts a smooth feel with no stickiness, and is easy to use. The aftershave cream spreads lightly when applied and can impart a moist, cool feel. With the aftershave cream, irritation of the skin is minimal and, after application, a lasting moisturizing, but clean feel can be imparted. Additionally, the stability of the product is very excellent.

Formulation Example 21

Solid Foundation

|  | Components | wt. % |
|---|---|---|
| [Pigment portion] (38.2 wt. %) | | |
| 1. | Treated spherical titanium oxide (average primary particle size: 0.4 μm) *38) | 18.0 |
| 2. | Treated iron oxide (mixture of black iron oxide, red iron oxide, and yellow iron oxide) *38) | 1.7 |
| 3. | Treated talc *38) | 6.0 |
| 4. | Treated mica *38) | 2.0 |
| 5. | Nε-lauroyl-L-lysine | 3.5 |
| 6. | Polyalkyl-methyl silsesquioxane (average primary particle size: 4 μm) | 5.0 |
| 7. | Octyl silylated fine particulate titanium oxide (average primary particle size: 10 nm) | 2.0 |
| [Liquid portion] Volatile Silicone (25 wt. %) | | |
| 8. | Decamethyl cyclopentasiloxane | 15.0 |
| 9. | Methyl trimethicone Polyol (6.5 wt. %) | 10.0 |
| 10. | 1,3-butylene glycol | 5.0 |
| 11. | Maltitol | 1.0 |
| 12. | Raffinose | 0.5 |
| Surfactant (2 wt. %) | | |
| 13. | Silicone compound No. 14 | 0.3 |
| 14. | Sorbitan isostearate | 1.7 |
| Solid or paste-like oil agent (5 wt. %) | | |
| 15. | Paraffin | 5.0 |
| Purified water (12.7 wt. %) | | |
| 16. | Purified water | 12.7 |
| Oil agent (9.5 wt. %) | | |
| 17. | Dimethylpolysiloxane (6 cst) | 3.0 |
| 18. | Methylphenylpolysiloxane | 2.0 |
| 19. | Paramethoxy octyl cinnamate | 2.0 |
| 20. | Propylene glycol dicaprylate | 2.0 |
| 21. | Dipentaerythrityl hexahydroxystearate | 0.5 |
| Bioactive component | | |
| 22. | Cranberry extract | 1.0 |
| Preservative | | |
| 23. | Paraben | 0.1 |

*38): Nε-lauroyl-L-lysine 5 wt. % treated pigment

Manufacturing Method
A: The oil-based liquid portion (components 8 to 9, components 13 to 15, components 17 to 21, and component 23) is uniformly mixed and dissolved at 80° C.
B: The pre-mixed and crushed pigment portion (components 1 to 7) is added thereto and uniformly dispersed at 80° C.
C: Then, the water-based liquid portion (components 10 to 12, component 16, and component 22) that was uniformly pre-mixed and dissolved at 80° C. is added to the mixture, emulsified, and dispersed.
D: The obtained emulsion is degassed, pressed into a cosmetic receptacle, and set in a hermetic container. Thus, a solid foundation is obtained.

Effects

When applied, the solid foundation does not impart a feeling of dryness to the skin and has excellent compatibility with the skin. The solid foundation has reduced oiliness and feels good when applied. Moreover cosmetic retainability is good. The stability of the product is good and hardly suffers from separation or agglomeration, and the foundation hardly cracks.

Formulation Example 22

Gel Daytime Use Skin-Lightening Cream

|  | Components | wt. % |
|---|---|---|
| 1. | SS-2910 *39) | 1.0 |
| 2 | Silicone compound No. 6 | 2.0 |
| 3. | SH 556 *40) | 5.0 |

127 -continued

| | Components | wt. % |
|---|---|---|
| 4. | SS-3408 *41) | 6.0 |
| 5. | Dimethylpolysiloxane (2 cst) | 6.0 |
| 6. | Glycerin | 5.0 |
| 7. | Dipropylene glycol | 10.0 |
| 8. | Methyl paraoxy benzoic acid | 0.2 |
| 9. | Sodium ascorbyl sulfate | 0.1 |
| 10. | Sodium ascorbyl phosphate | 0.1 |
| 11. | γ-aminobutyric acid | 0.1 |
| 12. | Appleseed extract (anti-oxidizing agent) | 0.1 |
| 13. | Sodium chloride | 0.9 |
| 14. | Perfume | 0.1 |
| 15. | Purified water | 63.4 |

*39): Polyether-modified Silicone
*40): Phenyl trimethicone
*41): Caprylyl methicone Manufacturing Method A: Components 1 to 5 are heated and dissolved at 60° C.
B: Components 6 to 15 are heated and dissolved at 60° C.
C: A is added to B while agitating and emulsifying/mixing is performed. D: Next, the mixture is cooled to 30° C. while agitating, and a container is filled with the mixture. Thus, a daytime use skin-lightening cream is obtained.

Effects

The daytime use skin-lightening cream is free of discomfort such as a feeling of dryness when applying, spreads lightly, and provides an excellent moisturizing sensation during use. The moisturizing effect thereof is lasting and the skin does not become dry and coarse. The daytime use skin-lightening cream is easy to use as a cosmetic base. Additionally, stability of the product is excellent with regard to temperature and passage of time.

Formulation Example 23

Polyol/O-Type Nonaqueous Gel Emulsion Topical Composition for Skin

| | Components | wt. % |
|---|---|---|
| 1. | Dimethylpolysiloxane (20 cst) | 5.0 |
| 2. | Dimethylpolysiloxane (2 cst) | 15.0 |
| 3. | Liquid paraffin | 10.0 |
| 4. | Cetyl 2-ethylhexanoate | 5.0 |
| 5. | Silicone compound No. 7 | 3.0 |
| 6. | Vitamin E | 0.1 |
| 7. | Ascorbyl phosphate Mg | 0.2 |
| 8. | Sodium chloride | 1.0 |
| 9. | Glycerin | 25.0 |
| 10. | 1,3-butylene glycol | 10.7 |
| 11. | Dipropylene glycol | 25.0 |

Manufacturing Method

A: Components 1 to 6 were heated and agitated at 50° C. and dissolved.

B: Separately, components 7 to 11 were dissolved by agitating and mixing at 50° C.

C: Emulsification is achieved by adding B in small amounts while holding the temperature of A at 50° C. and agitating uniformly.

Then, while agitating, the mixture is cooled to 30° C. so as to obtain a polyol/O-type nonaqueous gel emulsion topical composition for skin.

Effects

Because a stable gel emulsion of the nonaqueous system can be obtained, stability of the ascorbic acid derivative can be advantageously maintained and, as a result, it is expected that the benefits inherent in vitamin C (a bioactive substance) will be displayed mildly and for an extended period of time on or within the skin.

Formulation Example 24

Polyol/O-Type Nonaqueous Gel Emulsion Topical Composition for Skin

| | Components | wt. % |
|---|---|---|
| 1. | Dimethylpolysiloxane (20 cst) | 5.0 |
| 2. | Dimethylpolysiloxane (2 cst) | 15.0 |
| 3. | Liquid paraffin | 10.0 |
| 4. | Cetyl 2-ethylhexanoate | 5.0 |
| 5. | Silicone compound No. 7 | 3.0 |
| 6. | Trisodium ascorbyl palmitate phosphate | 0.2 |
| 7. | Vitamin E | 0.1 |
| 8. | Sodium chloride | 1.0 |
| 9. | Glycerin | 25.0 |
| 10. | 1,3-butylene glycol | 10.7 |
| 11. | Dipropylene glycol | 25.0 |

Manufacturing Method

A: Components 1 to 7 were heated, agitated at 50° C., and dissolved.

B: Separately, components 8 to 11 were dissolved by agitating and mixing at 50° C.

C: B is added in small amounts while holding the temperature of A at 50° C. and mixing uniformly.

Then, while agitating, the mixture is cooled to 30° C. so as to obtain a polyol/O-type nonaqueous gel emulsion topical composition for skin.

Effects

Because a stable gel emulsion of the nonaqueous system can be obtained, stability of the trisodium ascorbyl palmitate phosphate can be advantageously maintained and, as a result, it is expected that effective transdermal absorption of the topical composition will be obtained due to the properties particular to the substance, and that the benefits inherent in vitamin C (a bioactive substance) will be displayed mildly and for an extended period of time on or within the skin.

The invention claimed is:

1. A thickening agent or gelling agent for an oil-based raw material, the thickening agent or gelling agent comprising (A) a co-modified organopolysiloxane which has a hydrophilic group and a group having a siloxane dendron structure and which is expressed by general formula (1) below:

General Formula (1):

$$R^1_a L^1_b Q_c SiO_{(4-a-b-c)/2} \quad (1)$$

wherein, $R^1$ is a monovalent organic group with the exception of groups corresponding to $L^1$ or Q, or a hydrogen atom;

$L^1$ is a silylalkyl group having a siloxane dendron structure expressed by the following general formula (2) when i=1:

General Formula (2):

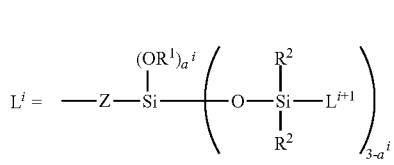
(2)

wherein, $R^1$ is synonymous with the groups described above, $R^2$ is an alkyl group having from 1 to 6 carbons or a phenyl group, and Z is a divalent organic group; i represents a generation of the silylalkyl group represented by $L^i$, and is an integer of 1 to c' when c' is a number of generations that is a number of repetitions of the silylalkyl group; the number of generations c' is an integer from 1 to 10, and $L^{i+1}$ is the silylalkyl group when i is less than c' and is a methyl group or a phenyl group when i=c'; $a^{i}$ is a number in a range of 0 to 3;

wherein the hydrophilic group Q is a hydrophilic group derived from a polyglycerin expressed by structural formula (4-1-1) below:

$$—R^{3'}—O—X^1{}_m—R^4 \qquad (4\text{-}1\text{-}1)$$

wherein $R^{3'}$ is a divalent organic group and $X^1$ are each independently at least one hydrophilic unit selected from the hydrophilic units expressed by general formulae (3-2-1) to (3-4-1) below, and m is a number in a range of 3 to 5; and $R^4$ is a hydrogen atom or a group selected from the group consisting of glycidyl groups, acyl groups, and alkyl groups having from 1 to 20 carbons,

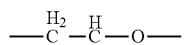
(3-2-1)

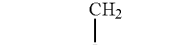
(3-3-1)

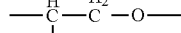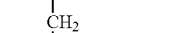
(3-4-1)

wherein, a, b, and c are in ranges so that $1.0 \le a \le 2.5$, $0.001 \le b \le 1.5$, and $0.001 \le c \le 1.5$;

wherein the component (A) is a co-modified organopolysiloxane expressed by structural formula (1-1-1) or structural formula (1-1-2) below:

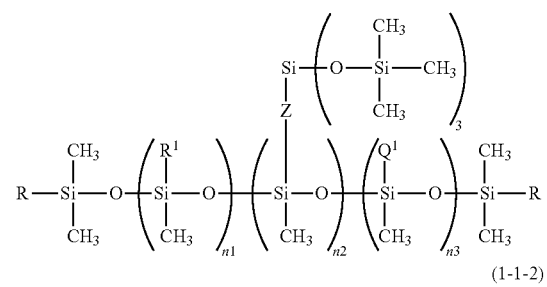
(1-1-1)

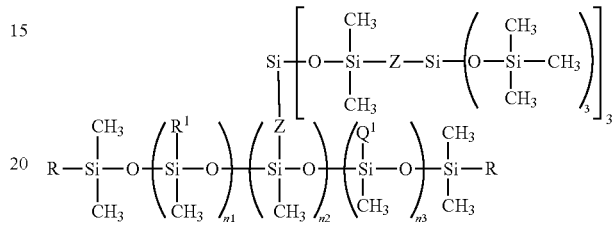
(1-1-2)

wherein Z and $R^1$ are groups that are synonymous with those described above; R is a group selected from $R^1$, the $L^1$, and $Q^1$, described hereinafter; n1, n2, and n3 are numbers that fall within the numerical ranges $200 \le n1 \le 1000$, $1 \le n2 \le 50$, and $0 \le n3 \le 20$, and when n3=0, at least one R is $Q^1$; and $Q^1$ are each independently a hydrophilic group derived from a polyglycerin expressed by structural formula (4-1-1) below:

$$—R^{3'}—O—X^1{}_m—R^4 \qquad (4\text{-}1\text{-}1)$$

and has a branch unit selected from groups expressed by structural formulae (3-5) to (3-7) below:

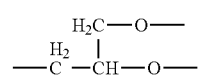
(3-5)

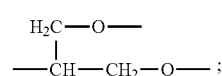
(3-7)

wherein $R^{3'}$ in structural formula (4-1-1) is a divalent organic group;

wherein $X^1$ in structural formula (4-1-1) are each independently at least one hydrophilic unit selected from the hydrophilic units expressed by general formulae (3-2-1) to (3-4-1) above, and m is a number in a range of 3 to 5; and wherein $R^4$ in structural formula (4-1-1) is a hydrogen atom or a group selected from the group consisting of glycidyl groups, acyl groups, and alkyl groups having from 1 to 20 carbons.

2. The thickening agent or gelling agent for an oil-based raw material according to claim 1, wherein the hydrophilic group Q is a hydrophilic group derived from a tetraglycerin.

3. The thickening agent or gelling agent for an oil-based raw material according to claim 1, further comprising (B) a powder or colorant.

4. The thickening agent or gelling agent for an oil-based raw material according to claim 1, further comprising (C) at least one component selected from a silicone-based surfactant with the exception of compounds corresponding to component (A), a crosslinking organopolysiloxane, a silicone resin, an acryl silicone dendrimer copolymer, a polyamide-modified silicone, and an alkyl-modified silicone resin wax.

5. The thickening agent or gelling agent for an oil-based raw material according to claim 1, wherein the oil-based raw material is (D1) at least one type of oil agent selected from a solid oil, a paste-form oil, a silicone oil, a hydrocarbon oil, and an ester oil.

6. The thickening agent or gelling agent for an oil-based raw material according to claim 3, wherein the component (B) is (B1) at least one type of powder or colorant selected from a silicone resin powder, a silicone rubber powder, an organic resin powder with the exception of silicone resin powders, an organo-modified clay mineral, titanium oxide, zinc oxide, a titanated mica, a metal soap, an inorganic body pigment, and an inorganic coloration pigment.

7. A gel composition comprising from 30 to 80 mass % of (D) an oil-based raw material, from 10 to 70 mass % of the thickening agent or gelling agent for an oil-based raw material described in claim 1, from 0 to 20 mass % of (E) at least one type of compound selected from a lower monohydric alcohol and an organic polyhydric alcohol-based compound, and from 0 to 20 mass % of water.

8. The gel composition according to claim 7, further comprising (F) a UV absorber.

9. The gel composition according to claim 7, further comprising (G) at least one type of compound selected from a sucrose fatty acid ester and a polyglycerol fatty acid ester.

10. The gel composition according to claim 7, further comprising (H) an organic film-forming agent.

11. The gel composition according to claim 7, further comprising (J) at least one type of compound selected from the group comprising an amino acid and/or a salt thereof, an inorganic salt, an organic acid and/or a salt thereof, and a water-soluble polymer.

12. A method for producing a cosmetic composition by blending from 0.1 to 4,000 parts by weight of water with 100 parts by weight of the gel composition described in claim 7.

13. A cosmetic composition obtained by blending from 0.1 to 4,000 parts by weight of water with 100 parts by weight of the gel composition described in claim 7.

14. A gel cosmetic composition comprising from 30 to 80 mass % of (D) an oil-based raw material, from 20 to 60 mass % of the thickening agent or gelling agent for an oil-based raw material described in claim 3, and from 0 to 20 mass % of water.

15. A method of adjusting the transparency of an emulsion composition comprising the thickening agent or gelling agent for an oil-based raw material described in claim 1, the method comprising independently mixing a water phase and an oil phase that contains the component (A) and (D) oil-based raw material, and then emulsifying after adjusting so that a difference in refractive index between the two phases at 25° C. is 0.0020 units or lower.

* * * * *